United States Patent
Smith et al.

(10) Patent No.: US 12,295,707 B2
(45) Date of Patent: May 13, 2025

(54) APPARATUSES, SYSTEMS, AND METHODS FOR CAPTURING A VIDEO OF A HUMAN PATIENT SUITABLE FOR MONITORING A CARDIAC, RESPIRATORY OR CARDIORESPIRATORY CONDITION

(71) Applicant: JRAS MEDICAL INC., St. John's (CA)

(72) Inventors: Andrew M. L. Smith, St. John's (CA); Andrew J. Smith, Vancouver (CA)

(73) Assignee: JRAS MEDICAL INC.

( * ) Notice: Subject to any disclaimer, the term of this patent is extended or adjusted under 35 U.S.C. 154(b) by 0 days.

(21) Appl. No.: 18/566,192

(22) PCT Filed: Aug. 2, 2022

(86) PCT No.: PCT/CA2022/051177
§ 371 (c)(1),
(2) Date: Dec. 1, 2023

(87) PCT Pub. No.: WO2023/010208
PCT Pub. Date: Feb. 9, 2023

(65) Prior Publication Data
US 2024/0260840 A1    Aug. 8, 2024

Related U.S. Application Data

(60) Provisional application No. 63/228,071, filed on Jul. 31, 2021.

(51) Int. Cl.
*A61B 5/0205* (2006.01)
*A61B 5/00* (2006.01)
*A61B 5/021* (2006.01)

(52) U.S. Cl.
CPC .......... *A61B 5/0205* (2013.01); *A61B 5/0077* (2013.01); *A61B 5/6825* (2013.01);
(Continued)

(58) Field of Classification Search
CPC ... A61B 5/0205; A61B 5/0077; A61B 5/6825; A61B 5/6887; A61B 5/02141; A61B 2562/0219
See application file for complete search history.

(56) References Cited

U.S. PATENT DOCUMENTS 7,769,420 B2    8/2010 Silver et al.
11,234,643 B2   2/2022 Nahmias et al.
(Continued)

FOREIGN PATENT DOCUMENTS

CA    3038097 A1    9/2020
CN    205597908 U   9/2016
(Continued)

OTHER PUBLICATIONS

Abnousi, F. et al., A novel noninvasive method for remote heart failure monitoring: the EuleriAn video Magnification apPLications In heart Failure and studY (AMPLIFY), npj Dig. Med. 80, 1-6 (2019).
(Continued)

Primary Examiner — Lynsey C Eiseman
Assistant Examiner — Skylar Lindsey Christianson
(74) Attorney, Agent, or Firm — Aird & McBurney LP

(57) ABSTRACT

An apparatus for capturing a video of a human patient suitable for monitoring a cardiac, respiratory or cardiorespiratory condition includes: an electronic imager. The imager is positionable with respect to a neck of the patient to be able to capture electronic video of the neck of the patient. The apparatus also includes a locator object external to the body of the patient, the locator object structured to be repeatedly stably positionable on the body of the patient with respect to an anatomic location on a torso of the patient, the locator object being connected to the imager. The apparatus also includes a reference element, the reference element being
(Continued)

positionable with respect to the neck of the patient by positioning of the locator object.

20 Claims, 25 Drawing Sheets

(52) U.S. Cl.
CPC ........ *A61B 5/6887* (2013.01); *A61B 5/02141* (2013.01); *A61B 2562/0219* (2013.01)

(56) References Cited

U.S. PATENT DOCUMENTS

| | | |
|---|---|---|
| 2006/0224053 A1 | 10/2006 | Black et al. |
| 2007/0093702 A1 | 4/2007 | Yu et al. |
| 2008/0294070 A1 | 11/2008 | Knori |
| 2010/0094141 A1 | 4/2010 | Puswella |
| 2013/0150735 A1 | 6/2013 | Cheng |
| 2014/0330335 A1 | 11/2014 | Errico et al. |
| 2017/0027457 A1* | 2/2017 | Wagle ...................... A61B 5/33 |
| 2017/0164904 A1 | 6/2017 | Kirenko |
| 2017/0164907 A1 | 6/2017 | Kirenko |
| 2017/0172434 A1 | 6/2017 | Amelard et al. |
| 2017/0296119 A1* | 10/2017 | DeBusschere ..... A61B 5/02028 |
| 2018/0177464 A1 | 6/2018 | Debusschere |
| 2020/0008684 A1 | 1/2020 | Feinberg |
| 2020/0121262 A1 | 4/2020 | De Haan |
| 2020/0221956 A1* | 7/2020 | Tzvieli ................... G01J 5/0025 |
| 2020/0383578 A1 | 12/2020 | Smith et al. |
| 2021/0113099 A1* | 4/2021 | Rogers ................. A61B 5/4803 |
| 2022/0039665 A1 | 2/2022 | Smith et al. |

FOREIGN PATENT DOCUMENTS

| | | |
|---|---|---|
| CN | 206556660 U | 10/2017 |
| EP | 1534386 A1 | 6/2005 |
| GB | 2408935 A | 6/2005 |
| WO | 03101534 A1 | 12/2003 |
| WO | 2010009141 A1 | 1/2010 |
| WO | 2018161159 A1 | 9/2018 |
| WO | 2020051676 A1 | 3/2020 |

OTHER PUBLICATIONS

Amelard, R. et al., Ph.D. Thesis, University of Waterloo, 2017, "Widefield Computational Biophotonic Imaging for Spatiotemporal Cardiovascular Hemodynamic Monitoring", Thesis/Dissertation, 123 pages.

García-López, I. et al., "Extracting the Jugular Venous Pulse from Anterior Neck Contact Photoplethysmography", Nat. Sci. Rep. 10, 3466 (2020). 12 pages.

Lam Po Tang, E. J. et al., "Non-contact Quantification of Jugular Venous Pulse Waveforms from Skin Displacements", Nat. Sci. Rep. 8, 17236 (2018), 12 pages.

Amelard R, Hughson RL, Greaves DK, Pfisterer KJ, Leung J, Clausi DA, Wong A., "Non-contact hemodynamic imaging reveals the jugular venous pulse waveform", Sci Rep. Jan. 9, 2017;7:40150. doi: 10.1038/srep40150. PMID: 28065933; PMCID: PMC5220303, 10 pages.

International Search Report PCT/CA2022/051177 dated Nov. 18, 2022, 3 pages.

* cited by examiner

APPARATUSES, SYSTEMS, AND METHODS FOR CAPTURING A VIDEO OF A HUMAN PATIENT SUITABLE FOR MONITORING A CARDIAC, RESPIRATORY OR CARDIORESPIRATORY CONDITION

CROSS-REFERENCE TO RELATED APPLICATIONS

This application claims priority to and the benefit of U.S. Provisional Application No. 63/228,071, filed Jul. 31, 2021 and entitled "Apparatus and Method for Capturing a Video of a Human Patient Suitable for Monitoring a Cardiac, Respiratory, or Cardiorespiratory Condition," the entire disclosure of which is hereby incorporated herein by reference.

TECHNICAL FIELD

The present technology relates to apparatuses and methods for monitoring a cardiac, respiratory or cardiorespiratory condition in the patient and can include, in some embodiments, systems and devices for capturing image data of a patient for monitoring the jugular venous pressure height.

BACKGROUND

Jugular venous pressure (JVP) or JVP height is a clinical sign evaluated for various applications, including assessment of heart failure (HF) and assessment of volumetric load on the heart.

The internal jugular vein (IJV) descends from the angle of the mandible to the middle of the clavicle at the posterior border of the sternocleidomastoideole. It transmits blood from the brain, skull, face, and neck to the superior venacava and ultimately to the right atrium of the heart. By observing the blood column engorging the IJV when the body, head and neck are at a specific angle to the horizontal, an assessment of the jugular venous pressure (JVP) and the right atrial pressure can be made. Evaluation of the JVP is a standard procedure in a clinical setting carried out by a physician as part of the physical examination of a patient. During examination, the vertical distance between the sternal angle and a top of the pulsation point of the IJV is measured. In some instances, a hepatojugular reflux test may be performed, e.g., by pressing the right upper quadrant of the abdomen, atop the liver, to cause more blood to rush into the right atrium and the JVP to increase. The hepatojugular reflux can be used to validate the point of jugular distension (e.g., by noting the upward movement of the IJV in response).

To measure the distance between the sternal angle and the top of the pulsation point of the IJV, a horizontal line is made from the highest IJV pulsation point to intersect a vertical line, which is erected perpendicular to the ground through the sternal angle of Louis. Typically, these "lines" are made usually of readily available straight objects, such as rulers. The distance between the sternal angle and the intersection of the two lines is measured along the vertical line. The sum of this measured distance plus 5 cm, which is obligatorily added owing to the fixed relationship between the outer surface of the patient's body and the midpoint of the right atrium (if measured when the patient is at a 30-degree angle), represents the patient's mean JVP. For example, FIG. 1 shows a diagram 10 of a patient lying on a bed at a reclination angle A (e.g., about 30 degrees). The vertical distance between the sternal angle ($H_{SA}$) and the height of the blood column in the IJV ($H_{IJV}$)+5 cm is the JVP ($H_{JVP}$ in FIG. 1).

The normal mean jugular venous pressure, determined as described above (i.e., 5 cm+ the vertical height in cm above the sternal angle), is 6 to 8 cm $H_2O$. Deviations from this normal range can reflect, for example, hypovolemia (i.e., where the mean venous pressure is less than, for example, about 5 cm $H_2O$) or hypervolemia (i.e., where the mean venous pressure is greater than, for example, about 8 cm $H_2O$). An elevated JVP assessed by a trained physician can suggest early volume overload, predict clinical deterioration and assist with therapeutic decisions in HF.

Currently, the JVP, as described above, can only be determined in the clinical setting. Practically speaking, this limits the periodicity within which the JVP of an outpatient can be measured, as such a patient is not normally going to return to the clinical setting on a frequent basis. Besides the inconvenience of so doing, typically the patients who would need to have more frequent JVP monitoring are elderly and have age-related or other mobility issues. Nonetheless, for some such patients, it may be more favorable to have their JVP monitored more frequently than their periodic visits to a clinical setting occur.

It is thus desirable to have systems, devices, and methods that can be used (at least) outside of the clinical setting to gather information allowing for the determination of a person's JVP.

SUMMARY

Systems, devices, and methods described herein enable monitoring of various conditions of a patient, including, for example, the JVP. In some embodiments, such monitoring can be performed outside of a clinical setting, while in other embodiments, such monitoring can be performed in a hospital or clinical setting, or in other suitable settings.

In some embodiments, an apparatus for monitoring a cardiac, respiratory, or cardiorespiratory condition of a patient can include an electronic imager or imaging device. The imager is positionable with respect to a neck of the patient to be able to capture electronic video of the neck of the patient. The apparatus also includes a locator object external to the body of the patient, the locator object structured to be repeatedly stably positionable on the body of the patient with respect to an anatomic location on a torso of the patient. The locator object is connected to the imager. The apparatus also includes a reference element, the reference element being positionable with respect to the neck of the patient by positioning of the locator object.

In some embodiments, a method for monitoring a cardiac, respiratory, or cardiorespiratory condition can include: an electronic imager or imaging device, the imager being positionable with respect to a neck of the patient to be able to capture the electronic video of the neck of the patient: a locator object external to the body of the patient, the locator object being structured to be repeatedly stably positionable on the body of the patient with respect to an anatomic location on a torso of the patient, the locator object being connected to the imager; and a reference element, the reference element being positionable with respect to the neck of the patient by positioning of the locator object, includes: positioning the apparatus with respect to the patient such that the imager is positionable with respect to the neck of the patient to be able to capture the electronic video of the neck of the patient. The method also includes positioning the locator object in a stable position on the body of the patient with respect to the anatomic location on the torso of the patient, thereby causing at least one of the reference elements and the imager to be positioned with respect to the neck of the patient such that the neck of the patient and at least part of the reference element are simultaneously able to be captured in the electronic video by the imager without movement of the imager. The method also includes causing the electronic video to be captured by the imager.

While the systems, devices, and methods described herein are largely described with reference to monitoring the JVP of a patient, it should be understood that such systems, devices and methods are not limited to monitoring (including determining) JVP but can also be used for measuring other physiological conditions of a patient, including, for example, heart rate, respiratory rate, blood pressure trends, oxygen saturation or carotid (arterial) pulsations. Other embodiments of the present technology are suitable for monitoring respiratory effort (e.g., normal and/or distressed). In some embodiments, systems, devices, and methods described herein may be used in monitoring patients with the following conditions: congestive heart failure (CHF), chronic obstructive pulmonary disease (COPD), combinations of both CHF and COPD, asthma, dialysis (e.g., peritoneal and hemodialysis). Further, some embodiments of the present technology may be used in monitoring patients with the following conditions: pericardial tamponade, conditions resulting in elevated intracardiac pressures, scenarios in which excess circulating blood volume is an issue (e.g., sceptic shock after volume resuscitation with IV fluid.), etc.

In some implementations, embodiments described herein include: (i) an electronic imager, (ii) a locator object external to the body of the patient, and (iii) a reference element. The general purpose of the electronic imager is to capture images appropriate to the monitoring of the condition to be monitored (e.g., images of the neck). The general purpose of the locator object is to assist in correctly positioning the frame of the camera such that within the frame of the camera is (are) the subject(s) appropriate to the monitoring of the condition to be monitored to be captured by the imager (e.g., the neck of the patient). The general purpose of the reference element is to provide a reference having known characteristics (e.g., size, shape, distance, etc.) to enable one or more mathematical calculations relevant to the condition to be monitored to be carried out. As a person or ordinary skill in the art would understand, each of the aforementioned elements may have purposes other than the general purposes provided above.

In some embodiments, when monitoring the JVP, the apparatus is used and functions in the following manner. The patient (or a person assisting them) prepares for the monitoring session by configuring a location where the monitoring session is to occur (e.g., if the location has not remained in the proper configuration from previous time that the monitoring had occurred). For example, the patient (or a person assisting them) can place a 30-degree wedge pillow on a flat location such as a bed. The patient (or the person assisting them) then places an apparatus of the present technology near to the patient's upper torso (e.g., near the patient's shoulder) on a flat surface. Once the apparatus is powered on, the patient (or the person assisting them) then takes the locator object and places the locator object on a particular anatomic location on the patient's torso (e.g., the patient's suprasternal notch). In some embodiments, the locator object may have been customized to that patient (e.g., calibrated to the patient), such as, for example, by a clinician previously.

In some embodiments, the locator object, the reference element, and the electronic imager are mechanically linked together, coupled to each other, or integrated into a single assembly, for example on a moveable arm of the apparatus. Moving the locator object to its correct or desired position, also causes the reference element and the electronic imager to move into their correct or desired positions. In its correct or desired position, the electronic imager can be positioned with respect to the neck of the patient such that the electronic imager can capture video of the neck of the patient in an area where the distention of the jugular vein is visible. In its correct position, the reference element can be positioned with respect to the neck of the patient such that (i) the reference element is also within the frame of the electronic imager, (ii) can be captured on video, and (iii) mathematical calculations can be made from a captured video to calculate the JVP of the patient.

One advantage of the embodiments presented herein is that the apparatus does not need to be exactly positioned in the same location each time a monitoring session occurs. The use of the locator object and its connection to the other components of the apparatus means that the videos captured by the electronic imager during each monitoring session may be used to calculate the JVP notwithstanding the fact that the apparatus itself may not be in the same position as in previous monitoring sessions. This is the case as the reference element provides a known reference to enable such calculations.

Other advantages of the embodiments described herein are that a clinician need not be present during the monitoring session and/or the monitoring session need not occur in a clinical setting. The design of the apparatus ensures that each of the components are correctly positioned. The captured video from a session may be processed via computer or manually by a human, e.g., to determine the JVP. This processing need not occur at the location where the monitoring session takes place (e.g., at a patient's residence). The captured video may be sent by any conventional methods and/or devices to a location where it may be processed and the JVP determined. In view of this, monitoring sessions may occur with a much greater frequency than would be the case if the patient were required to travel to a clinical setting for each monitoring session.

The electronic imager can generally be any imager capable of taking electronic images whose size, shape and principle of operation are otherwise compatible with the remainder of the apparatus (as is described below). For example, in some embodiments, a conventional smart phone camera device (or a similar device or a device which operates on the same principles) can be used. In the context of a device being used to monitor a patient's JVP, the electronic imager is positionable with respect to a neck of the patient to be able to capture electronic video of the neck of the patient (to be able to capture distention of the patient's IJV). An example of such positioning was described above.

The locator object may be structured to be repeatedly and stably positionable on the body of the patient with respect to an anatomic location on a torso of the patient. In many instances, this is accomplished by having at least a portion of the locator object being sized and shaped to be able to register with the size and shape of a particular anatomic location of a patient's body. Examples of such anatomic locations are the patient's sternum, sternal angle, manubrium, clavicular heads, and suprasternal notch (or commonly referred to as the sternal notch). So, for example, in the case where the anatomic location is the patient's suprasternal notch, the locator object may have a spherical portion dimensioned to snugly fit within the notch. In some embodiments, the locator object has an interchangeable patient-contacting element, thus allowing the locator object to be customized to the patient (e.g., to accommodate a change in size, a change in anatomic location, etc. between patients) to aid in repeatably and stably positioning the locator object on the patient's torso. In addition, or in the alterative, in some embodiments the locator object has at least one adjustable patient-contacting element. Where present, an adjustable patient-contacting element also may assist in repeatably and stably positioning the locator object on the patient's torso. In other embodiments, in addition or in the alternative to the foregoing, the entire locator object may be an interchangeable element, for example, to serve a similar purpose.

In some embodiments, the locator object is connected to the imager. It can be the connection of the locator object to the imager that (at least in part) causes the imager to have the correct elements to be imaged within its frame so that those elements may be captured on video. Such elements may be, for example, a particular part(s) or portion(s) of the patient's body (e.g., their neck) as well as a part(s) or portion(s) or the entirety of the reference element (e.g., depending on the design and/or construction of the reference element). Such elements may also include, for example, a part(s) or portion(s) or the entirety of the locator object itself, on the design, use, operation, etc. of the apparatus. For example, in some embodiments, the locator object may be used in combination with the reference element in mathematical calculations.

In the context of the present embodiments, the locator object may be connected to the imager in any number of ways that are not otherwise incompatible with the other structure of the device and the device's functions. For example, in various embodiments, the connection between the locator object and the imager may be one of mechanical, electronic, electromechanical, magnetic, via adhesive, etc. As an example, in some embodiments, the connection between the two may be a simple mechanical connection, such that physically moving the locator object moves the imager. In such a case, for example, the apparatus is structured such that when the locator object is physically moved to and then stably appropriately positioned on the anatomic location on the patient's torso, the imager appropriately simultaneously moves with the locator object and then comes to rest in an appropriate position to capture the video it needs to capture when the locator object is finally itself appropriately positioned. Again, as examples, in such cases, in some embodiments, the two are simply fixedly connectedly to one another: whereas in other embodiments, the two may be connected to each other via more complex moveable mechanical linkages.

In some embodiments, in addition or as an alternative to the mechanical connection, the locator object and the imager may be electronically connected to one another (for example, directly or indirectly, via a computer processor). For example, the locator object can transmit an electronic signal which would allow for its position in space to be located or determined, and the imager can be moved by an appropriate motor(s) to the appropriate position. Such an electronic signal can be transmitted via wire or wirelessly transmitted. In another example, the patient can, e.g., via a patient-actuated switch (e.g., on the locator object), cause a signal to be sent that the locator object is correctly positioned, and the imager (e.g., in combination with a processor of a compute device) can use machine vision and artificial intelligence to position itself. In some embodiments, an imaging device such as a camera can be mounted on a wall with high resolution and a wide field of view. The wide field of view can capture the neck of a patient. A patient or user can place a locator object and/or reference object in the patient's sternal notch and press a button that activates the imaging device. The imaging device does not need to move, given its wide field of view, and can estimate the JVP as it is imaging the reference object.

In some embodiments, the connection between the locator object and the imager includes a member fixedly attached to the locator object. This member may be alignable with respect to a landmark of the torso of the patient during positioning of the locator object with respect to the anatomic location on the torso of the patient. In this manner, the member can assist in correctly positioning the locator object. For example, the member may be straight or have a straight portion, and during the correct positioning of the locator object the member or its straight portion can be aligned so as to be centrally longitudinally positioned along the sternum of the patient. Such an arrangement is shown and further described with reference to FIG. 12.

In some embodiments, the reference element is positionable with respect to the neck of the patient by positioning of the locator object. In some embodiments, the reference element is of a known size and shape. Knowing these characteristics allows for processing (e.g., mathematical and/or geometric calculations) to be performed on the captured images (e.g., automatically by a processor of a compute device). For example, when it is the JVP of the patient that is being monitored, the reference element is structured to allow for the determination of the JVP from video captured by the imager in accordance with the present technology.

In some embodiments, the reference element is a physical object, or a portion of a physical object. For example, in an embodiment where the JVP of the patient is being monitored, the reference element may be three parallel rods of known dimensions and spacing.

In different embodiments, the relationship of the reference element to the locator object can vary. In some embodiments, the reference element is separate from the locator object (but may be connected to a different part of the apparatus to which the locator object itself is connected). In some embodiments, the reference element is physically connected to the locator object. In some embodiments, the reference element is the locator object. In some embodiments, the reference element extends from the locator object. In some embodiments, the reference element is otherwise mechanically linked to the locator object. For ease of use, in some embodiments, the reference element is correctly positioned once the locator object is correctly positioned with respect to the anatomic location on the torso of the patient. In other embodiments, it may be that the reference element needs positioning after the locator object is positioned.

In some embodiments, the reference element need not be a physical object. For example, the reference element can be structured electromagnetic radiation, e.g., that is projected onto a neck of the patient. In an embodiment where the JVP of the patient is being monitored, the reference element may be three parallel lines of visible light projected onto an appropriate area on the neck of the patient. As was described above, the relationship of the reference element and the locator object varies in different embodiments. For example, in some embodiments the reference element may be projected from the locator objector itself, whereas in other embodiments the reference element may be projected from another part of the apparatus or even a separate coordinated device. In another embodiment, the reference element may be projected from a device mechanically linked to the locator object.

In some embodiments, the reference element may have markings that can facilitate mathematical calculations to be performed. For example, in some embodiments, the markings on the reference element may be one or more scales of measurement (e.g., centimeters). In some embodiments the markings may include numbers. In some embodiments, the markings may be or may include different patterns, colors, or other differentiations in structured electromagnetic radiation.

In most embodiments, when it is the JVP of the patient that is being monitored, the locator object is connected to the imager such that, when the locator object is positioned on the body of the patient with respect to the anatomic location on the torso of the patient, both the neck of the patient and at least part of the reference element are simultaneously able to be captured in the video by the imager without movement of the imager. In some such embodiments, this may make the determination of JVP simpler as there is no movement of the imager to take into account in such determination. In some embodiments, the imager may move during video capture (e.g., to sweep along a slight arc), and be able to carry out the necessary determination of JVP, either by taking such movement into account in those determinations or by ignoring such movement. In some embodiments, precise determinations are not necessary, e.g., approximations or simplifications can be sufficient for estimating JVP.

In some embodiments, the imager may capture more of the reference element in the video, and in such cases, the greater capture of the reference element can enable more accurate determinations of JVP.

In some embodiments, the locator object is connected to the imager such that, when the locator object is positioned on the body of the patient with respect to the anatomic location on the torso of the patient, both the neck of the patient and an entirety of the reference element are simultaneously able to be captured in the video by the imager without movement of the imager. In some embodiments, it may be the case that the entirety of the reference element need not be in the captured video in order to carry out the necessary determination of JVP. In other embodiments, it may be the case that the entirety of the reference element needs to be in the captured video to facilitate the determination of JVP.

It can be appreciated that systems, devices, and methods described herein are not limited to an apparatus having a single imager, a single locator object and/or a single reference element. In some embodiments, apparatuses of the present technology may have multiple imagers, multiple locator objects and/or multiple reference elements.

As described above, e.g., with reference to FIG. 1, the neck of a patient contains the IJV and the external jugular vein (EJV) of the patient. When the JVP of the patient that is being monitored, the locator object can be connected to the imager such that, when the locator object is positioned on the body of the patient with respect to the anatomic location on the torso of the patient, both (i) an area of the skin of the neck overlying at least one of the IJV and the EJV of the patient, and (ii) the at least part of the reference element (e.g., sufficient for determining the position of the IJV and/or EJV relative to the reference element for determining the JVP), are simultaneously able to be captured in the video by the imager without movement of the imager.

In some embodiments, the locator object has a sensor for sensing at least one physiological parameter of the patient. In the context of the present technology, a sensor may be one or more of any number of types and kinds of sensors. Some non-limiting examples include a contact sensor, an electrocardiogram (ECG) electrode, a pulse oximeter (PPG), a temperature sensor, an electrodermal activity sensor, etc. For example, a contact sensor may be used to send a signal that the locator object has been positioned on the patient's body. In some embodiments, a contact sensor may be present along with an accelerometer whose signal can be used to determine whether the locator object is moving (and thus not yet stably positioned on the body of the patient, notwithstanding the fact that the contact sensor is sending a signal). In some embodiments, the apparatus can have or be operatively coupled to a processor programmed to automatically start capturing video based on having received the appropriate signals from the contact sensor and/or the accelerometer. Thus, in some embodiments, the sensor is in electronic communication with the imager. In another example, the accelerometer can be used to determine the angle of the patient with respect to a horizontal reference axis.

In some embodiments, the sensor is synchronizable with data from the imager. Thus, in some embodiments, the captured video and the data from the sensor are coordinated. In a non-limiting example, when the sensor is an ECG electrode or a pulse oximeter, the imager may collect data in synchroneity with the signals from the sensor.

In some embodiments, the time at which the sensor data is recorded and the time at which image (e.g., video) data from the imager is recorded are both known or determinable by the apparatus in absolute and/or relative time. For example, in some embodiments, the clock of a sensor can be used to gate the imager (or vice versa). In other embodiments, a processor can generate a clock signal that gates both the imager and the sensor(s). In still other embodiments, both the image data and the sensor data are time-stamped using the same clock signal and the data is temporally aligned in a post-processing step.

In some embodiments, the sampling rate of the sensor (or sensors, if more than one is present) may be a multiple of the sampling rate of the imager. As an example, the ratio of the sensor data sampling rate to the imager data sampling rate in some embodiments is 2:1. Thus, the sensor data would be sampled at $T_1$, $T_2$, $T_3$, $T_4$, $T_5$, etc. whereas the imager data would be sampled only at $T_1$, $T_3$, $T_5$, etc. (with the interval between each $T_n$ and $T_{n+1}$ being a constant). In such an example, the sensor data may be used to assist in interpreting the imager data. In other embodiments, other ratios of different sensor sampling rates can be used, e.g., about 0.5:1, about 1:1, about 2:1, about 3:1, about 4:1, about 5:1, about 10:1, inclusive of all sub-ranges and values therebetween.

In some embodiments, the apparatus has a sensor providing information relevant to the determination of an angle of inclination of the locator object when the locator object is stably positioned on the body of the patient with respect to the anatomic location on the torso of the patient. In some such embodiments, the sensor is at least one of an accelerometer and/or a gyroscope fixed in orientation with respect to the locator object. Further, in some such embodiments, the sensor is located within the locator object itself, and is in electronic communication with a processor of the apparatus (or a remote processor). As described above, when measuring JVP, the patient may be inclined at a specific known angle (e.g., about 10 to about 90 degrees from horizontal, or about 30 to about 60 degrees from horizontal). In some embodiments, this angle is generally maintained consistent each time that the JVP of the patient is monitored, for example, by having the patient lie on a wedge-shaped pillow having a set angle. In other embodiments, the angle need not be consistent, and the JVP is calculated (or estimated) taking into account the then current angle of the patient at the time the data is collected (e.g., using trigonometry and/or data collected by a gyroscope and/or accelerometer). In some embodiments, an angle of the long axis of the neck of the patient to horizontal may also differ from an angle of the patient's body. As such, in some embodiments, the long axis of the neck can be determined, e.g., using a static image of the neck with image processing, and this angle of the neck can be combined with an angle of the body to provide a more accurate estimate of the JVP.

In some embodiments, the apparatus is structured to rest on the torso of the patient when in use and capturing the video. In some such embodiments, for example, when the apparatus is repeatedly and stably positioned on the patient (as described above), the angle of the patient can be calculated or estimated (as the case may be) from the angle of the apparatus (e.g., via from gyroscope and/or accelerometer data). The accelerometer and/or gyroscope can be located in the apparatus (e.g., in any location within the portion that is positioned on the patient's body).

In some embodiments, the apparatus has a portion that is shaped to conform to a portion of the torso of the patient such that the portion of the apparatus rests on the portion of the torso of the patient when the apparatus is in use capturing the video. In some such embodiments, the apparatus being so structured assists in repeatedly and stably positioning the apparatus (as described above), which can improve the reliability of the data.

In some embodiments, the apparatus further comprises an articulated arm having a first end movably connected to a base station and a second end movably connected to the imager.

In some embodiments, the apparatus further comprises at least two electrodes for contacting the skin of the patient in order to generate an electrocardiogram (ECG) signal. In some embodiments, one or more of the electrodes may be in contact with the skin of the patient owing to the positioning of one of the other elements of the apparatus. For example, in some embodiments, an electrode can be positioned on the locator object such that when the locator object is correctly positioned on the patient's body, the electrode is in contact with the person's skin. In some embodiments, one or more of the electrodes are positioned on the apparatus such that they may be contacted by the patient when in use (e.g., capturing image data). For example, in some embodiments, one of the electrodes may be on a handgrip spaced apart from the locator object and the patient's hand can come into contact with the electrode when the patient positions the locator object (e.g., grips the handgrip) for capturing image data.

In some embodiments, the apparatus comprises a microphone. The microphone may, for example, be used to capture the sound of the patient's voice while the patent is speaking. In some embodiments, this may be the case where, for example, the apparatus includes appropriate hardware and software to enable a call with another person (e.g., a clinician) at a distance. In addition, or in the alternative, the apparatus may include appropriate hardware and software to provide computer-controlled voice instructions to the patient and to record or otherwise process information spoken back by the patient. In addition, or in the alternative, the microphone (or one of the microphones if the apparatus has multiple microphones) can be in contact with the skin of and used to capture sounds generated by the patient's body (e.g., heart sounds such as from the cardiac valves opening and closing; respiratory sounds such as from air moving into and out of the lungs; and/or blood flow sounds from blood following in the blood vessels and/or through the valves). The microphone may be in electronic communication with a processor, e.g., in order to store the captured sounds and/or transmit them via a communications link.

In some embodiments, the apparatus comprises a speaker. In some embodiments this may be the case where, for example, the apparatus includes appropriate hardware and software to enable a call with another person (e.g., a clinician) at a distance. In addition, or in the alternative, the apparatus may include appropriate hardware and software to provide computer-controlled voice and/or otherwise audible instructions to the patient. In addition, or in the alternative, the speaker (or speakers, if more than one) can be used to allow the patient to hear their bodily sounds being captured by the microphone.

In some embodiments, the apparatus further comprises a patient-actuated (or user-actuated) sensor element operatively connected to the imager, e.g., to control video capture by the imager. In some embodiments, for example, the patient-actuated sensor element may be a button that the patient pushes to indicate that the patient is ready to begin the monitoring session. In some such embodiments, the button may directly initiate the monitoring session, while in other embodiments the button may indirectly initiate the monitoring session (for example, by initiating a computer process that in due course, e.g., after a predetermined period of time, begins the monitoring session). As a non-limiting example, the patient-actuated sensor element can be located in any suitable location on the apparatus, such as, for example, on the locator object, on the movable portion, or on the base, and be in electronic communication with the imager (either directly, or indirectly via a processor).

In some embodiments, the apparatus further comprises (i) a processor in electronic communication with the imager, (ii) an information storage medium in electronic communication with the processor; and (iii) a wireless transceiver in electronic communication with the processor. In some such embodiments, the apparatus may be able to connect to a network, such as, for example, the Internet, via a wired connection through an Ethernet port and/or via a mobile communication (cellular) network or WI-FI™.

In some embodiments, the apparatus comprises: (i) an electromagnetic radiation source providing electromagnetic radiation in at least the near infrared (NIR) spectrum; and (ii) a filter allowing for the selective passage of electromagnetic radiation in the NIR spectrum to the imager. In some such embodiment, the apparatus being so structured assists in reducing issues associated with ambient lighting. For example, artificial ambient lighting can introduce noise into the signals due to flickering.

In some embodiments, the electronic imager is a first electronic imager; and the apparatus further comprises a second electronic imager fixed in position with respect to the first electronic imager. In some such embodiments, having two imagers that are fixed and at a known distance apart from one another can enable stereo vision or depth sensing, e.g., through a calculation of a disparity map (or difference map). This can enable generation of a 3D model of the structure (e.g., the neck) being imaged.

Further, in some such embodiments, first electronic imager can be an near-infrared (NIR) spectrum imager, and the second electronic imager can be a visible light spectrum imager. In some such embodiments, the NIR spectrum imager captures images in greyscale, whereas the visible light spectrum imager captures images in color. Thus, the two imagers provide different information that can be helpful for image processing, segmentation, and/or feature identification. For example, different images can be generated from the different spectra, which can be useful for evaluating different features in the image data (e.g., where one feature may be better captured via NIR while another feature may be better captured via visible light). The color information in combination with the NIR information can assist with feature identification and/or segmenting different objects (e.g., clothing from skin, or the outline of the body from the backgrounds).

In some embodiments, where the JVP of the patient is being monitored, the reference element has predetermined dimensions that render a height of the column of blood in a jugular vein of the patient with respect to at least one of the patient's sternal angle and a grossly immobile anatomic feature of the patient's torso determinable by a computer processor from the captured electronic video. In some such embodiments, the grossly immobile anatomic feature of the patient's torso is one of a patient's clavicular head, suprasternal notch, and sternum. In some embodiments, the height of the column of blood in the jugular vein of the patient with respect to at least one of the patient's sternal angle and the grossly immobile anatomic feature of the patient's upper body is determinable by a processor from the captured electronic video without having reference to a different image of the neck of the patient and/or without requiring the imager having been fixed in a precise position with respect to the neck of the patient at the time that the electronic video was captured. In one example, determining the height of the JVP can rely on the reference element being of a known size. With the known size, this enables the conversion between pixels (e.g., of the video captured by the imager) and physical distance. A clinician can review the video and determine the location of the pulsation in the IJV. The distance or vertical height can be calculated using the number of pixels and the angle of the patient (e.g., as measured by the apparatus's accelerometer). This can be performed each time an assessment of the JVP is made using the captured video, without reference to another image (e.g., a previously captured image in which all of the distances between the various elements in the image were known).

In some embodiments, the imager is not in direct contact with the patient. In some embodiments, the imager is not held in a fixed position by a mechanical connection to the patient's body.

In another aspect, implementations of the present technology provide a method of capturing an electronic video of a human patient suitable for monitoring a cardiac, respiratory or cardiorespiratory condition, via an apparatus including, (a) an electronic imager, the imager being positionable with respect to a neck of the patient to be able to capture the electronic video of the neck of the patient: (b) a locator object external to the body of the patient, the locator object being structured to be repeatedly stably positionable on the body of the patient with respect to an anatomic location on a torso of the patient, the locator object being connected to the imager; and (c) a reference element, the reference element being positionable with respect to the neck of the patient by positioning of the locator object: the method comprising: (i) positioning the apparatus with respect to the patient such that the imager is positionable with respect to the neck of the patient to be able to capture the electronic video of the neck of the patient: (ii) positioning the locator object in a stable position on the body of the patient with respect to the anatomic location on the torso of the patient, thereby causing at least one of the reference element and the imager to be positioned with respect to the neck of the patient such that the neck of the patient and at least part of the reference element are simultaneously able to be captured in the electronic video by the imager without movement of the imager; and (iii) causing the electronic video to be captured by the imager.

In some implementations, positioning the locator object in a stable position on the body of the patient with respect to the anatomic location on the torso of the patient, causes both of the reference element and the imager to be positioned with respect to the neck of the patient such that the neck of the patient and at least part of the reference element are simultaneously able to be captured in the electronic video by the imager without movement of the imager.

BRIEF DESCRIPTION OF THE DRAWINGS

For a better understanding of the present technology, as well as other aspects and further features thereof, reference is made to the following description, which is to be used in conjunction with the accompanying drawings, where.

DETAILED DESCRIPTION

Systems, devices, and methods described herein enable monitoring of various conditions of a patient, including, for example, the JVP. In some embodiments, systems, devices, and methods can be configured to enable monitoring in settings outside of a physician's office, such as, for example, a patient's home.

Figure 2A:
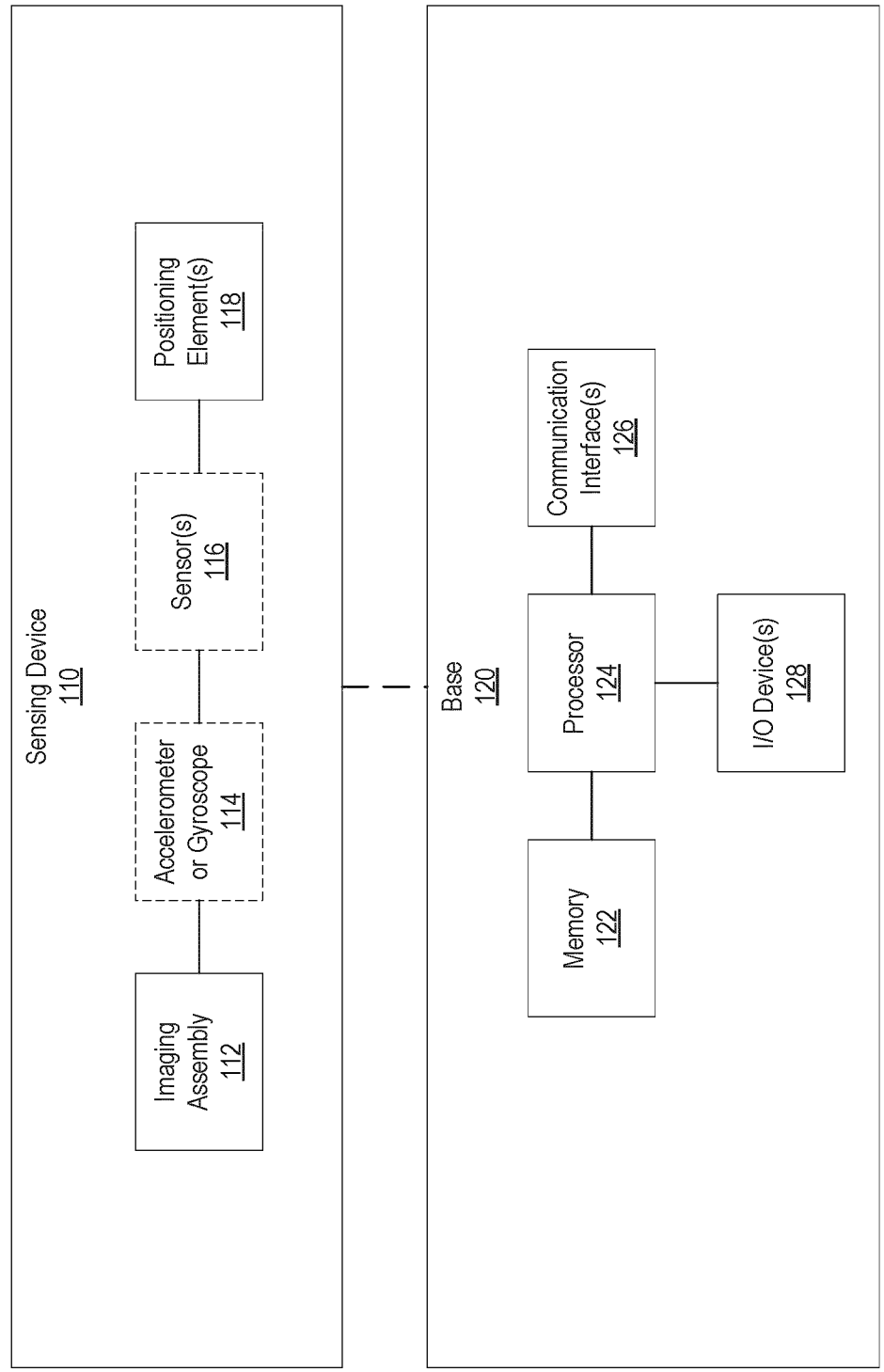
FIG. 2A is a schematic block diagram of a system for measuring a patient's JVP, according to an embodiment.

Referring to the figures, FIG. 2A is schematic block diagram of a system 100 for measuring a patient's JVP and/or other physiological parameters or conditions, according to an embodiment. The system 100 includes a sensing device 110 that may include an imaging assembly 112, and a position element(s) 118, and optionally, an accelerometer or gyroscope 114 and/or one or more additional sensor(s) 116. The system 100 also includes a base 120 that may include a memory 122, a processor 124, a communication interface(s) 126, and an input/output (I/O) devices(s) 128. The sensing device 110 is configured to measure a JVP of a patient. The sensing device 110 may be operatively coupled to the base 120 and configured to measure the JVP based on an activation signal received from the base, and transmit signals corresponding to the measured JVP to the base 120, as described herein.

While described as being configured to measure the JVP of a patient, in some embodiments, the system 100 or any other system or sensing device described herein may be configured to measure or monitor carotid (arterial) pulsation, respiratory effort (normal and/or distressed), or may be use for monitoring patients suffering from CHF, COPD, asthma, dialysis (both peritoneal and hemodialysis), pericardial tamponade, conditions resulting in elevated intracardiac pressures, scenarios in which excess circulating blood volume is an issue (e.g., sceptic shock after volume resuscitation with IV fluid.), or any other disease or condition. All such measurements, determinations, or diagnosis are contemplated and should be considered to be within the scope of the present disclosure.

The sensing device 110 may include a housing (not shown) within which components of the sensing device, for example, the imaging assembly 112, the accelerometer or gyroscope 114, the sensor(s) and/or the positioning element 118 may be disposed, coupled to, integrated with, or monolithically formed therewith. The imaging assembly 112 is configured to capture a single image, a set of images, and/or a video a portion of a body of the patient (e.g., a neck of a patient). For example, the imaging assembly 112 may be used to capture an image, a set of images, or a video of a neck of a patient in an area of the neck where the distention of the IJV is visible to determine the JVP of a patient. In various embodiments, the imaging assembly 112 may include one or more imagers such as, for example, a charged coupled device (CCD) camera configured to capture the image(s) and/or video(s) of the portion of the body of the patient. In some embodiments, the imaging assembly 112 may also include one or more lenses (e.g., concave and/or convex lenses), and/or one or more filters (e.g., optical filters, software filters such as high pass filter(s), low pass filter(s), bandpass filter(s), etc.) to facilitate capture of images (e.g., at different wavelengths), to reduce noise, and/or increase image focus. The imaging assembly 112 may be positionable with respect to the neck of the patient to be able to capture image(s) and/or video of the patient so as to be able to capture distention of the patient's IJV and thereby, the patient's JVP. The imaging assembly 112 generates a signal indicative of the captured images and may communicate the signal to the base 120 (for example, the processor 124 included in the base 120).

In some embodiments, the imaging assembly 112 may also include a light source or an illumination mechanism (e.g., an electromagnetic radiation source such as one or more light emitting diodes (LEDs)) to illuminate the portion of the body (e.g., the neck) of the patient. The light source can be configured to generate sufficient illumination for a camera of the imaging assembly 112 to image the patient's body. In some embodiments, the illumination mechanism can be configured to generate light for capturing one or more images or a video. For example, the illumination mechanism can be configured to illuminate an area for optical imaging.

In some embodiments, the illumination mechanism may be configured to generate a reference element, e.g., to provide a reference having known characteristics (e.g., size, shape, distance, etc.) that may enable to determination of JVP (e.g., via one or more mathematical calculations). For example, the illumination mechanism may be configured to project electromagnetic radiation (e.g., visible light, infrared or ultraviolet (UV) light) in the form of a reference image or reference element, e.g., onto the neck of the patient that is within the field of view of the imager included in the imaging assembly 112. In some embodiments, the reference image may include one or more lines (e.g., three parallel lines, or any other suitable marking) of projected light onto an appropriate area on the neck of the patient. In some embodiments, the reference image may have markings that can facilitate mathematical calculations to be performed. For example, in some embodiments, the markings on the reference element may be one or more scales of measurement (e.g., centimeters). In some embodiments the markings may include numbers. In some embodiments, the markings may be or may include but are not limited to, different patterns, colors, or other differentiations in structured electromagnetic radiation.

In other embodiments, the reference element may be a separate physical element that may be positioned on the neck of the patient by the patient, a caregiver, or a medical practitioner, before imaging the neck of the patient by the imaging assembly 112. In operation, the sensing device 110 may be disposed on the body of the patient such that the imaging assembly 112 is positioned in a desired orientation with respect to the neck of the patient to allow capturing of video of the neck of the patient in an area where the distention of the jugular vein is visible. In its correct position, the reference element is positioned with respect to the neck of the patient such that (i) the reference element is also within the frame of the electronic imager, (ii) can be captured on video being recorded by the imaging assembly 112, and (iii) mathematical calculations can be made from a captured video to calculate the JVP of the patient.

In some embodiments, the imaging assembly 112 may include an illumination mechanism implemented as an electromagnetic radiation source providing electromagnetic radiation in at least the near infrared (NIR) spectrum, and a filter allowing for the selective passage of electromagnetic radiation in the NIR spectrum to the imager included in the imaging assembly 112. In some such embodiment, the apparatus being so structured assists in reducing issues associated with ambient lighting. For example, artificial ambient lighting can introduce noise into the signals due to flickering. Having a dedicated light source in the NIR spectrum, and a filter only allowing passage of electromagnetic radiation in the NIR spectrum may substantially reduce noise due to flickering or other optical lighting noise. NIR imaging can also reduce the impact of skin tone on image processing.

In some embodiments, the imaging assembly 112 may include a plurality of imagers. For example, the imaging assembly 112 may include a first electronic imager, and a second electronic imager fixed in position with respect to the first electronic imager. Having two imagers that are a fixed and known distance apart may enable stereo vision or depth sensing through a calculation of a disparity or difference map. This can enable generation of a 3D model of the structure (e.g., the neck) of the patient being imaged. In some embodiments, the first electronic imager may be an NIR spectrum imager, and the second electronic imager may be a visible light spectrum imager. In some such embodiments, the NIR spectrum imager captures images in greyscale, whereas the visible light spectrum imager captures images in color. Thus, the two imagers provide different information that can be helpful for image processing, segmentation and feature identification. The color information in combination with the NIR information can assist with feature identification and/or segmenting different objects from one another (e.g., clothing from skin, or the outline of the body from the backgrounds).

In some embodiments, where the JVP of the patient is being monitored, the reference element that may be generated by an illumination mechanism (e.g., a visible or NIR electromagnetic radiation source) included in the imaging assembly 112 or included in another part of the sensing device (e.g., in a positioning element or locator object), may have predetermined dimensions that render a height of the column of blood in a jugular vein of the patient with respect to at least one of the patient's sternal angle and/or another grossly immobile anatomic feature of the patient's torso determinable by the processor 124, e.g., from the captured image(s) or video of the neck or portion of the neck of the patient and a locator object (e.g., positioning element 118). In some such embodiments, another grossly immobile anatomic feature of the patient's torso is one of a patient's clavicular head, suprasternal notch, and sternum.

In some embodiments, the height of the column of blood in the jugular vein of the patient with respect to at least one of the patient's sternal angle and another grossly immobile anatomic feature of the patient's upper body is determinable by the processor 124 from the captured electronic video without having reference to a different image of the neck of the patient and/or without requiring the imager having been fixed in a precise position with respect to the neck of the patient at the time that the electronic video was captured. For example, the reference element being of a known size can facilitate the measurement of JVP. For example, the known size of the reference can enables the conversion between pixels (e.g., of the video captured by the imager) and a physical distance. In some embodiments, a clinician may be able to review the video and determine the location of the top of the pulsation in the IJV. Alternatively or additionally, the processor 124 via processing the video data can be configured to identify the location of the top of the pulsation of the IJV. The distance (e.g., vertical distance) can be calculated using the number of pixels and the angle of the patient (e.g., as measured by the accelerometer or gyroscope 114).

The accelerometer or gyroscope 114 may include, for example, a microelectromechanical (MEMS) accelerometer, a piezoelectric accelerometer, a piezoresistive accelerometer, a capacitive accelerometer, a rotating gyroscope, a vibrating gyroscope, an optical gyroscope, any other suitable accelerometer or acceleration sensing device, or a combination thereof. In some embodiment, the accelerometer or gyroscope 114 may be used to determine whether the imaging assembly 112 is moving, for example, due to the sensing device 110 (e.g., the positioning element 118 of the sensing device 110) not stably positioned on the body of the patient as described herein. In some embodiments, the processor 124 included in the base 120 may be configured to receive a signal from the accelerometer or gyroscope 112, and based on the accelerometer or gyroscope signal, activate the imaging assembly 112 based on determining that the sensing device 110 is sufficiently stably disposed on the patient's body (e.g., is stationary or is moving less than a predefined amount or rate) for the imaging assembly 112 to capture clear image(s) or video(s) of the portion of the patient's body.

Figure 1:
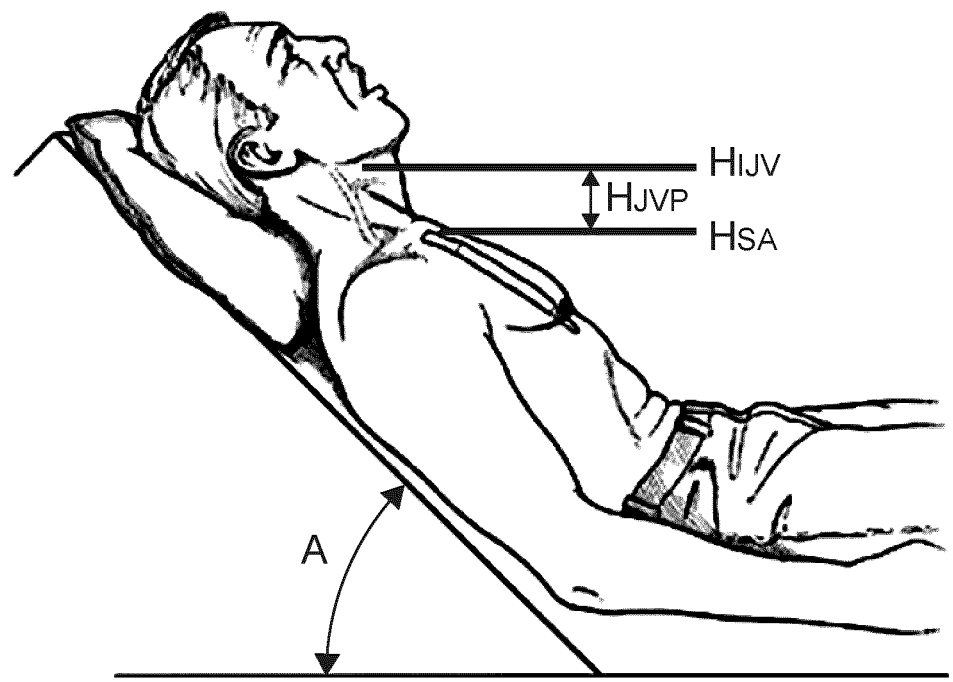
FIG. 1 shows an illustration of a patient lying on a bed at an angle and illustrates the vertical distance relative to the sternal angle on the IJV of the patient that can be used to determine the JVP height of the patient.

In another example, the accelerometer or gyroscope 114 can also be used to determine the angle of the patient with respect to a horizontal axis. For example, when measuring a patient's JVP, the angle at which the patient's torso and neck are inclined to the horizontal may be between about 30 degrees to about 60 degrees. Depending on the specific angle that the patient is inclined, the vertical height or distance between the sternal angle and the top of the pulsation point of the IJV may change, e.g., as described above with reference to FIG. 1. Thus, the accelerometer or gyroscope 114 may be configured to measure and communicate the angle of inclination to the processor 124 of the base 120. In some embodiments, the processor 124 may be configured to activate the imaging assembly 112 when the patient is inclined at an angle between about 30 degrees and about 60 degrees, and the sensing device 110 is stably disposed on the patient's body. In some embodiments, the processor 124 can use the angle data acquired by the accelerometer or gyroscope 114 in determining a vertical distance between the sternal angle and top of the pulsation point of the IJV, e.g., to determine the JVP.

The sensing device 110 may also include one or more sensors 116 that may be configured to sense at least one physiological parameter of the patient. In some embodiments, at least a portion of the sensor(s) 116 may project outward from housing of the sensing device 110, or be generally accessible through the housing so as to able to contact a portion of the body of the patient (e.g., sternum or chest of the patient, or a hand of a patient) and measure one or more physiological parameters of the patient. In some embodiments, the sensor(s) 116 may include a contact sensor, an ECG electrode, a PPG sensor, any other suitable sensor, or a combination thereof. In some embodiments, the sensor(s) 116 may be configured to contact the patient's skin, for example, a skin of a sternum or torso of the patient, or provided on grips defined on the housing of the sensing device 110 so as to contact skin of a hand or one or more fingers of the patient when the patient grips the sensing device to measure the patient's JVP (or any other physiological parameter described herein). In some embodiments, the sensor(s) 116 may include at least two electrodes for contacting the skin of the patient to capture an ECG signal. In some embodiments, the one or more of the electrodes may be in contact with the skin of the patient when the sensing device 110 is properly position on a patient for image capture (e.g., by imaging assembly 112). For example, in some embodiments it may be that one of the electrodes is on a locator object (e.g., positioning element 118) and is positioned on the locator object such that when the locator object is correctly positioned on the patient's body, the electrode is in contact with the patient's skin.

In some embodiments, the sensor(s) 116 may be used to send a signal that the sensing device 110 has been positioned on the patient's body. In some embodiments, a signal from the sensor(s) 116 in combination with the signal from the accelerometer 112 whose signal can be used to determine whether the sensing device 110 is moving at rate beyond a predetermined threshold (e.g., at rate of greater than 0.01 mm/second or about 1 mm/second, including all sub-ranges and values therebetween) and thus not yet stably positioned on the body of the patient. In some embodiments, the processor 124 may be configured to automatically start capturing video based on having received the appropriate signals from the sensor(s) 116 and/or the accelerometer or gyroscope 114, e.g., that the sensing device 110 is stably positioned and that the inclination of the patient's torso and neck are within range for determining the patient's JVP.

In some embodiments, the sensor(s) 116 is synchronizable with imaging data from the imaging assembly 112, for example, by the processor 124 included in the base 120 or some other processor that is operatively coupled to the system 100 (e.g., via communication interface(s) 126). Thus, in some embodiments, the captured video and the data from the sensor(s) 116 are coordinated or synchronized. In a non-limiting example, when the sensor(s) 116 include an ECG electrode or a pulse oximeter, the imaging assembly 112 may collect data in synchroneity with the signals from the sensor(s) 116. For example, the time at which the sensor(s) 116 data is recorded and the time at which image (video) data from the imager is recorded can be known or determinable by the processor 124 in absolute and/or relative time. For example, in some embodiments, the clock of the sensor(s) 116 and/or the accelerometer 114 can be used to gate the imager (or vice versa). In some embodiments, the processor 124 generates a clock signal that gates both the imaging assembly 112 and the sensor(s) 116. In some embodiments, both the image data and the sensor data are timestamped using the same clock signal and the data is temporally aligned in a post-processing step, for example, by the processor 124 or a remote processor (e.g., a user device such as a mobile phone, a tablet, a laptop computer, or a desktop computer, or a remote server).

In some embodiments the sampling rate of the sensor(s) 116 may be a multiple of the sampling rate of the imaging assembly 112. For example, the ratio of the sensor(s) 116 data sampling rate to the imaging assembly 112 data sampling rate in some embodiments can be between about 0.5:1 to about 10:1, including all values and sub-ranges therebetween, including about 2:1. When the ratio is 2:1, the sensor(s) 116 data can be sampled at $T_1$, $T_2$, $T_3$, $T_4$, $T_5$, etc. whereas the imaging assembly 112 data can be sampled only at $T_1$, $T_3$, $T_5$, etc. (with the interval between each $T_n$ and $T_{n+1}$ being a constant). In such an example, the sensor(s) 116 data may be used to assist in interpreting the imaging assembly 112 data.

In some embodiments, the sensor(s) 116 can include a microphone or other audio capture device. The audio capture device may, for example, be used to capture the sound of the patient's voice while the patient is speaking, or to capture other sounds generated by a patient (e.g., breathing, heart sounds, etc.). For example, the audio capture device can be in contact with the skin of the patient and used to capture sounds generated by the patient's body, for example, heart sounds (e.g., from the cardiac valves opening and closing); respiratory sounds (e.g., from air moving into and out of the lungs); and/or blood flow sounds from blood following in the blood vessels and/or through the valves.

The positioning element(s) 118 may be configured or structured to facilitate a correct or desired positioning of the sensing device 110 on the body (e.g., a torso or sternum) of the patient, e.g., so as to position the imaging assembly 112 in the correct or desired position relative to the portion of the body of the patient (e.g., the neck of the patient) for measurement or monitoring of a condition of the patient. For example, in some embodiments, the positioning element(s) 118 can be configured to facilitate positioning of the sensing device 110 such that the portion of the body of the patient (e.g., the neck of the patient) is within the field of view of the imager of the imaging assembly 112 when the sensing device 110 is positioning on the patient as guided by the positioning element(s) 118. This may be desirable to enable the imaging assembly to perform appropriate monitoring of the JVP or any other condition or physiological parameter of the patient as described herein.

In some embodiments, the positioning element(s) 118 can include or be implemented as a locator object. For example, the positioning element(s) 118 implemented as a locator object may be structured to be positionable on the body of the patient with respect to an anatomic location on a patient. In some implementations, this may be accomplished by having at least a portion of the positioning element(s) 118 be sized and shaped to be able to register with the size and shape of a particular anatomic location of a patient's body. Examples of such anatomic locations are the patient's sternum, sternal angle, manubrium, clavicular heads, and suprasternal notch. For example, in implementations where the anatomic location is the patient's suprasternal notch, the positioning element(s) 118 may have a spherical portion (e.g., a hemispherical shaped projection coupled to a base of the housing of the sensing device 110 or monolithically formed in the base of the housing) dimensioned to snugly fit within the notch. In some embodiments, the position element(s) 118 may include an interchangeable or adjustable patient-contacting element, thus allowing positioning element to be customized to the patient (e.g., to accommodate a change in size, a change in anatomic location, etc. between patients) to aid in positioning the positioning element(s) 118 on the patient's torso, and thereby correctly positioning the imaging assembly 112 relative to the portion (e.g., the neck) of the patient's body. The positioning element 118 implemented as a locator object can aid the imaging assembly (or an imager of the imaging assembly) in determining a fixed reference point (e.g., sternal angle) via processing and analysis (e.g., mathematical calculations). Such can be accomplished via imaging processing or mechanical measurement given a mechanical linkage between the imager and the locator object. As such, the locator object aids in positioning the device by also enables the determination of an anatomic landmark.

In addition, or in the alterative, in some embodiments the positioning element(s) 118 has at least one adjustable patient-contacting element. Where present, an adjustable patient-contacting element also may assist in positioning the positioning element(s) 118 on the patient's torso. In other embodiments, in addition or in the alternative to the foregoing, the positioning element(s) 118 may be an interchangeable element, for example, to serve a similar purpose. In some embodiments, the sensing device 110 may include a first positioning element configured to be positioned on a first portion of the patient's body (e.g., a spherical element or portion configured to be positioned on the suprasternal notch) and a second positioning element spaced apart from the first positioning element and configured to be positioned on a separate part of the patient's body (e.g., on a pectoral muscle or chest). Providing multiple positioning elements 118 may allow more substantially stable and correct positioning of the sensing device 110 on the torso of the patient.

The sensing device 110 is operatively coupled to the base 120. In some embodiments, the base 120 may include a base housing (not shown) that includes grooves, notches, cavities, platforms, etc. or is otherwise, generally shaped to allow a portion of the housing of the sensing device 110 to be disposed thereon in a first configuration (e.g., a storage configuration, or charging configuration, in which the sensing device 110 is not being used). In some embodiments, the base housing of the base 120 may include a platform projecting, protruding, coupled to, or otherwise, formed in the base housing on which the sensing device 110 may be disposed in the first configuration.

In some embodiments, the base housing may include or define one or more grooves or cavities within which the positioning element(s) 118 may be disposed in the first configuration. For example, the base housing may define a first groove or cavity configured to receive a first position element 118 of the sensing device (e.g., the spherical portion included in a sternum alignment tool), and a second groove or cavity configured to receive a second positioning element (e.g., a second protrusion or arm coupled to or monolithically formed in the sensing device housing) in the first configuration. In some embodiments, the base housing may also include an arm that may define one or more grooves, and that may be configured to receive and/or support a portion of the sensing device housing in the first configuration. In use, the sensing device 110 can be removed from the base 120 and be placed on a patient, e.g., in a second configuration. In the second configuration, the sensing device 110 can be configured to make the desired measurements of the one or more physiological parameters of the patient.

In some embodiments, the sensing device 110 may also be physically coupled to the base 120 via a linkage assembly (not shown). For example, the linkage assembly may include one or more arms (e.g., an articulating arm) physically coupling the sensing device 110 to the base 120. In some embodiments, the linkage assembly may include a first arm hingedly, pivotally, or otherwise, rotatably coupled to the base housing, and a second arm hingedly, pivotally, or otherwise, rotatably coupled to the first arm at a distal end thereof, and also hingedly, pivotally, or otherwise, rotatably coupled to the sensing device body of the sensing device 110 at proximate end thereof. Such a linkage assembly may provide a wide range of motion (e.g., 360 degrees freedom of motion) to the sensing device 110 to facilitate correct or desired positioning of the sensing device 110 on the body of the patient, while assisting the patient in maintaining the sensing device 110 in a stable position on the torso of the patient. Moreover, communication leads (e.g., electrical lead)s may be routed through the one or more arms to communicatively couple the sensing device 110 to the base 120 (e.g., the processor 124 via the communication interface 126), and/or to allow the sensing device 110 to receive electrical power from the base 120.

In some embodiments, the linkage assembly may include one or more conductors, such as, an electrical lead, an electrical wire, a flat cord, a coiled cord, or any other suitable electrical lead physically as well as communicatively coupling the sensing device 110 to the base 120 (e.g., to the processor 124 of the base 120 via the communication interface 126 of the base 120). The electrical lead may be permanently connected to the sensing device 110 and/or the base 120 or removably coupled thereto. Such an electrical lead may allow complete freedom of motion of sensing device 120 by the patient, thereby facilitating correct positioning of the sensing device 110 on the body (e.g. torso) of the patient as well as increasing portability by reducing weight and mobility of the system 100.

In some embodiments, the sensing device 110 may only be communicatively coupled to the base 120 but not physically coupled to the base 120. For example, the sensing device 110 may include a wireless transceiver (e.g., a half-transceiver, a full-duplex transceiver, an RF transceiver, an optical transceiver, BLUETOOTH® transceiver, a WI-FIR transceiver, a near field communication (NFC) transceiver, any other suitable wireless transceiver or a combination thereof) to send to and/or receive signals from the base 120 (e.g., activation signals, deactivation signals, image or video data signals, accelerometer 114 data signals, sensor(s) 116 data signals, or any other signals pertaining to the operation of the system 100). In some embodiments, the sensing device 110 may include a power source (not shown) and a wireless charging mechanism (e.g., wireless charging coils) configured to receive an electromagnetic charging signal from corresponding wireless charging mechanism (e.g., corresponding wireless charging coils) that may be included in the communication interface(s) 126 of the base 120.

As previously described, the base 120 includes the memory 122, the processor 124, the communication interface(s) 126, and the I/O device(s) 128, and may also include additional components to facilitate operation of the sensing device 110. The memory 122 can be any suitable memory device(s) configured to store data, information, computer code or instructions (such as those described herein), and/or the like. In some embodiments, the memory 122 can be and/or can include one or more of a random access memory (RAM), static RAM (SRAM), dynamic RAM (DRAM), a memory buffer, an erasable programmable read-only memory (EPROM), an electrically erasable read-only memory (EEPROM), a read-only memory (ROM), flash memory, volatile memory, non-volatile memory, combinations thereof, and the like. In some embodiments, the memory 122 can store instructions to cause the processor 124 to execute modules, processes, and/or functions associated with the system 100, such as models, calculations, or other algorithms to analyze image(s) or video(s) captured by the imaging assembly 112, accelerometer 114 data sensor(s) 116 data, etc. In some embodiments, the memory 122 may also be configured to at least temporarily store image and/or video data, accelerometer 114 data, and/or sensor(s) 116 data, for example, until the data is transmitted to a user device or a remote server.

The processor 124 can be any suitable processing device(s) configured to run and/or execute a set of instructions or code. For example, the processor 124 can be and/or can include one or more data processors, image processors, graphics processing units (GPU), physics processing units, digital signal processors (DSP), analog signal processors, mixed-signal processors, machine learning processors, deep learning processors, finite state machines (FSM), compression processors (e.g., data compression to reduce data rate and/or memory requirements), encryption processors (e.g., for secure wireless data and/or power transfer), and/or the like. The processor 124 can be, for example, a general-purpose processor, central processing unit (CPU), microprocessor, microcontroller, Field Programmable Gate Array (FPGA), an Application Specific Integrated Circuit (ASIC), a processor board, a virtual processor, and/or the like. The processor 124 can be configured to run and/or execute application processes and/or other modules, processes and/or functions associated with the system 100. The underlying device technologies may be provided in a variety of component types, for example, metal-oxide semiconductor field-effect transistor (MOSFET) technologies like complementary metal-oxide semiconductor (CMOS), bipolar technologies like generative adversarial network (GAN), polymer technologies (e.g., silicon-conjugated polymer and metal-conjugated polymer-metal structures), mixed analog and digital, and/or the like. In some embodiments, the processor 124 can be configured to receive data from one or more sensors, the imaging assembly, or other components of the sensing device 110 and to process that data, e.g., to determine the JVP height or other physiological parameters of a patient. Alternatively or additionally, the processor 124 can be configured to send the data from one or more sensors, the imaging assembly, or other components of the sensing device 110 to one or more remote devices (e.g., via a network or the cloud) for further processing and/or analysis.

The communication interface(s) 126 can be any suitable device(s) and/or interface(s) that can communicate with the sensing device 110 (e.g., any or the devices, sensors, and/or data sources described above with respect to the sensing device 110, and/or any combination or part thereof), a network (e.g., a local area network (LAN), a wide area network (WAN), or the cloud), or an external device (e.g., a user device such as cell phone, tablet, a laptop, or a desktop computer, etc.). Moreover, the communication interface(s) 126 can include one or more wired and/or wireless interfaces, such as, for example, Ethernet interfaces, optical carrier (OC) interfaces, and/or asynchronous transfer mode (ATM) interfaces. In some embodiments, the communication interface(s) 126 can be, for example, a network interface card and/or the like that can include at least an Ethernet port and/or a wireless radio (e.g., a WI-FIR) radio, a BLUETOOTH®) radio, cellular such as 3G, 4G, 5G, etc., 802.11X Zigbee, etc.). In some embodiments, the communication interface(s) 126 can include one or more satellite, WI-FI, BLUETOOTH, or cellular antenna. In some embodiments, the communication interface(s) 126 can be communicably coupled to an external device (e.g., an external processor) that includes one or more satellite, WI-FI, BLUETOOTH, or cellular antenna, or a power source such as a battery or a solar panel. In some embodiments, the communication interface(s) 126 can be configured to receive imaging or video signals from the imaging assembly 112, the movement or positioning signals from the accelerometer or gyroscope 114, and/or sensor data from the sensor(s) 116. In some embodiments, the communication interface(s) 126 may also be configured to communicate signals to the sensing device 110, for example, an activation signal to activate the imaging assembly 112 (e.g., one or more imagers and/or electromagnetic radiation sources included in the imaging assembly 112), the accelerometer or gyroscope 114, and/or the sensor(s) 116.

The I/O device(s) 128 may include any suitable device to receive input from a user or communicate an output to the patient or user. In some embodiments, the I/O device(s) 128 may include an activation mechanism or otherwise, a user actuated element (e.g., a touch button, a push button, a switch, a touchpad, etc.) to turn on or otherwise, activate the sensing device 110, or to allow the user to enter information, request information, or set various parameters of the sensing device 110 (e.g., image capture rate, video bit rate, light intensity, etc.). In some embodiments, the I/O device(s) 128 may include a visual indicator (e.g., LED lights, a display, etc.) to display information to the patient or the user. Such information may include, but is not limited to the patient's JVP, other patient physiological parameters such as patient blood oxygen, heart rate, blood pressure, temperature, etc., time of day, communication interface(s) status (e.g., WI-FIR) connectivity status), or any other suitable information or a combination thereof.

In some embodiments, the I/O device(s) 128 may include a microphone. The microphone may, for example, be used to capture the sound of the patient's voice while the patent is speaking. This may be the case where, for example, the base 120 may include appropriate hardware and software to enable a call with another person (e.g., a clinician) at a distance. In addition, or in the alternative, the base 120 may include appropriate hardware and software to provide computer-controlled voice instructions to the patient and to record or otherwise process information spoken back by the patient. In addition, or in the alternative, the microphone (or one of the microphones if the I/O device(s) 128 has multiple microphones) can be in contact with the skin of the patient and used to capture sounds generated by the patient's body, for example, heart sounds (e.g., from the cardiac valves opening and closing); respiratory sounds (e.g., from air moving into and out of the lungs); and/or blood flow sounds from blood following in the blood vessels and/or through the valves. In such embodiments, the microphone may be provided in the sensing device 110 (e.g., be included in the sensor(s) 116 of the sensing device 110). The microphone may be in electronic communication with the processor 126, e.g., in order to store the captured sounds and/or transmit them via a communications link.

In some embodiments, the I/O device(s) 128 may include a speaker. In some embodiments this may be the case where, for example, the base 120 includes appropriate hardware and software to enable a call with another person (e.g., a clinician) at a distance. In addition, or in the alternative, the base 120 or the sensing device 110 may include appropriate hardware and software to provide computer-controlled voice and/or otherwise audible instructions to the patient. In addition, or in the alternative, the speaker (or speakers, if more than one) can be used to allow the patient to hear their bodily sounds being captured by the microphone. In some embodiments, the speakers can be used to provide instructions to a user, e.g., for positioning the sensing device 110 on the patient for measuring JVP. In some embodiments, depending on signals received from the accelerometer or gyroscope 114, the sensor(s) 116, and/or the imaging assembly 112, the processor 124 of the base 120 can be configured to generate instructions for the user (e.g., patient) to help the user correct an incorrect positioning or usage of the sensing device 110. For example, if the accelerometer or gyroscope 114 provides data to the processor 124, whereby the processor 124 detects that the patient is not at an appropriate angle for measuring JVP, the processor 124 via the speaker or another I/O device 124 can inform the user of such incorrect positioning (e.g., generate a sound, turn on or flash a light, etc.) and/or instruct the user on how to correct his positioning.

The processor 124 may be configured to perform any suitable operations for measuring one or more physiological parameters of a patient and/or communicating such parameters to other remote devices, as previously described in detail with respect to the sensing device 110. In some embodiments, the processor 124 may be configured to communicate an activation signal to the sensing device 110 to activate the sensing device 110, for example, provide electrical power to the various components included in the sensing device 110 in response to the activation mechanism being engaged by the user. In some embodiments, the processor 124 may be configured to receive signals from the accelerometer to determine an angle of inclination or reclining angle of the patient's torso, the location of the imaging assembly 112 relative to the target portion of the body of the patient (e.g., the patient's neck), and/or a rate of displacement or otherwise velocity of the sensing device 110.

In response to determining that the angle of the inclination of the patient's torso is within a predetermined range (e.g., in the range of about 30 degrees to about 60 degrees, inclusive), the target portion of the patient's body (e.g., the patient's neck) is within the field of vision of the imager of the imaging assembly 112, and/or the sensing device is not moving or being displaced at rate that is less than a threshold rate (e.g., less than 0.5 mm/second), the processor 124 may be configured to instruct the imaging assembly to initiate image or video capture of the target portion of the patient's body. In some embodiments, the processor 124 may also be configured to activate the electromagnetic radiation source that may be included in the imaging assembly 112 as previously described herein, to illuminate the target portion of the patient's body, and/or project the reference element(s) on the target portion, as previously described.

Figure 2B:
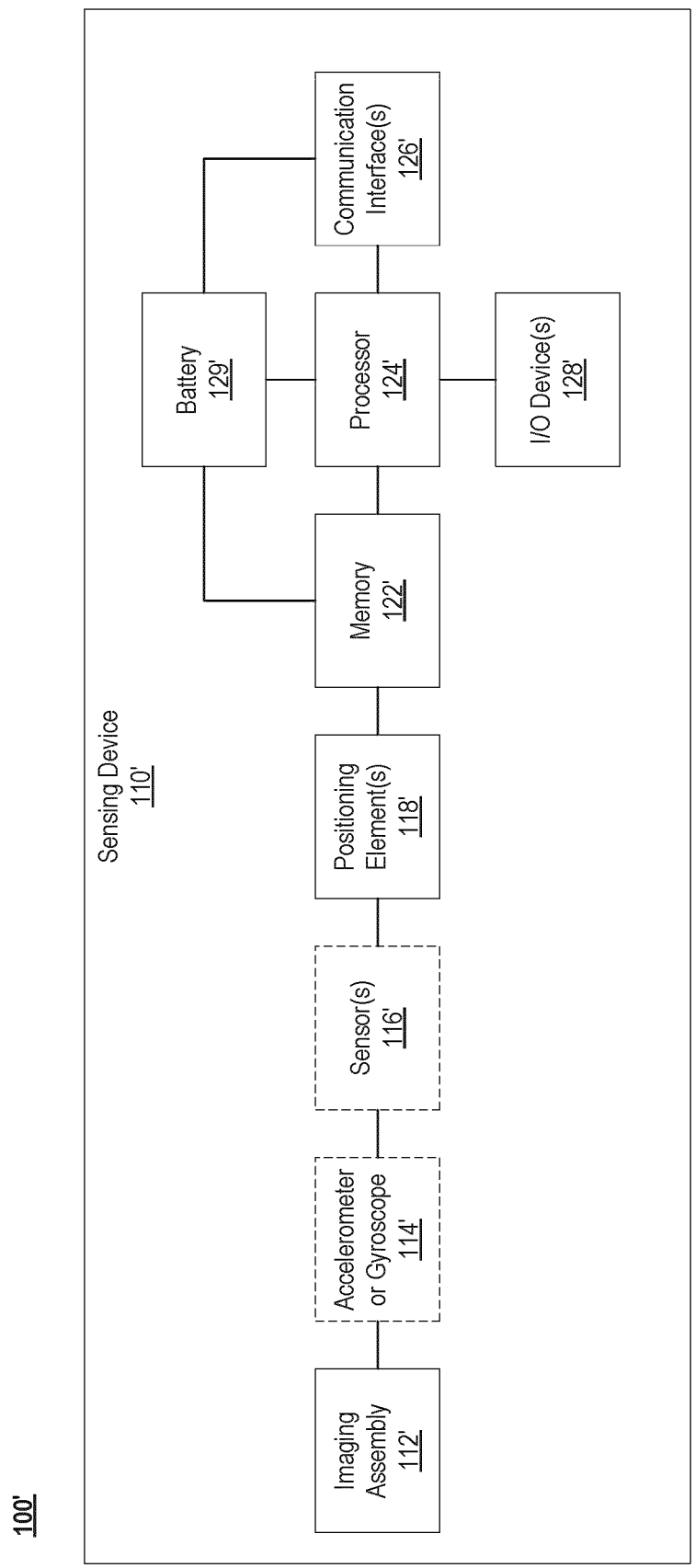
FIG. 2B is a schematic block diagram of a system for measuring a patient's JVP, according to an embodiment.

In some embodiments, a system for measuring one or more physiological parameters of a patient can be a portable unit that does not have a base. For example, FIG. 2B is schematic block diagram of an alternative system 100' for measuring a patient's JVP and/or other physiological parameters, according to an embodiment. The system 100' includes a sensing device 110' that may include an imaging assembly 112', and a position element(s) 118", and optionally, an accelerometer or gyroscope 114' and/or one or more sensor(s) 116'. The imaging assembly 112', the accelerometer or gyroscope 114', the sensor(s) 116', and the positioning element(s) 118' may be substantially similar to the imaging assembly 112, the accelerometer or gyroscope 114, the sensor(s) 116, and the positioning element 118, respectively described with respect to FIG. 2A and therefore, not described in further detail herein.

Different from the system 100, the system 100' does not include a base. Instead, the sensing device 110' further includes a memory 122', a processor 124', a communication interface(s) 126', a I/O device(s) 128', and a battery 129', which may be disposed within a housing of the sensing device 110', and communicatively coupled to the imaging assembly 112', the accelerometer 114', and/or the sensor(s) 116'. The memory 122', the processor 124', the communication interface(s) 126', and the I/O device(s) 128' may be substantially similar to the memory 122, the processor 124, the communication interface(s) 126, and the I/O device(s) 128 described in FIG. 2A. The battery 129' may include a rechargeable battery (e.g., Li-ion, NiCad, etc.) or a disposable battery, and configured to provide electrical power to the imaging assembly 112', the accelerometer 114', the sensor(s) 116', the memory 122", the processor 124', the communication interface(s) 126', and/or the I/O device(s) 128'. In some embodiments, in which the battery 129' is a rechargeable battery, the system 100' may include an electrical socket or jack configured to be plugged into an external power source, for example, a wall outlet via the electrical lead, to recharge the battery 129'. Integrating the memory 122', the processor 124', the communication interface(s) 126', and the I/O device 128' into the sensing device 110' increases the portability of the system 100', for example, allowing the system 100' to fit in a small package for the patient to carry with the patient while traveling, providing flexibility for the patient in using the system 100' at a location of the patient's choice, and making it easier for the patient to position the sensing device 110' on the body of the patient.

Figure 3C:
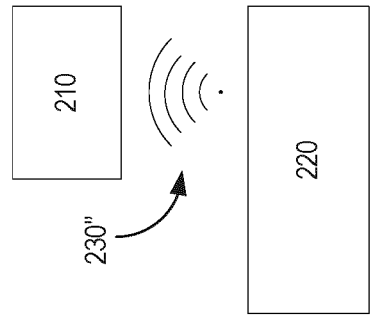
FIGS. 3A, 3B, and 3C are schematic illustrations of various configurations of a sensing device and a base of system for measuring JVP, according to embodiments.
Figure 3B:
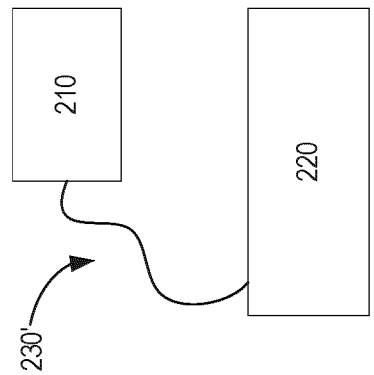
Figure 3A:
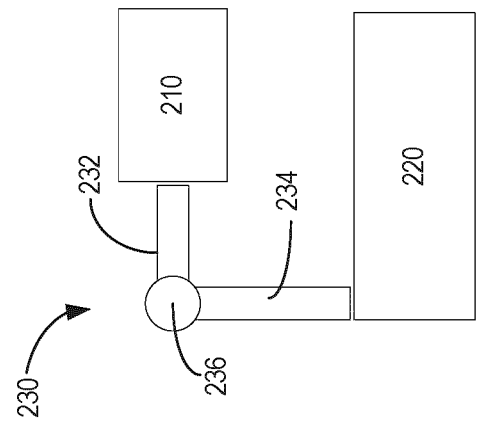

FIGS. 3A, 3B, and 3C are schematic illustrations of various configurations for operatively coupling a sensing device to a base of system for measuring JVP or other physiological parameters of a patient, according to various embodiments. For example, FIG. 3A is a schematic block diagram of a coupling mechanism 230 configured to couple a sensing device 210 to the base 220. The sensing device 210 and the base 220 may be substantially similar to the sensing device 110 and base 120 previously described and therefore, not described in further detail herein. In some embodiments, the coupling mechanism 230 may include a linkage arm that is capable of articulation and may provide greater than about 180 degrees (e.g., up to about 360 degrees) freedom of motion or rotation about the X, Y, and/or Z axis. For example, the coupling mechanism 230 may include a first arm 232 coupled at its proximate end to the sensing device 210. In some embodiments, the proximate end of the first arm 232 may be pivotally, hingedly, and/or rotationally coupled to the sensing device 210 (e.g., via a ball-socket joint, a hinge, a rotary joint, etc.) to allow rotation of the sensing device 220 relative to the first arm 232 about at least one axis (e.g., the X axis).

A distal end of the first arm 232 is coupled to a proximate end of a second arm 234 included in the coupling mechanism 230 via a joint 236. The joint 236 may include any suitable joint (e.g., a rotary joint, a ball-socket joint, etc.) allowing, for example, the first arm to rotate about at least two axes (e.g., the X and Y axes) so as to allow at least 180 degrees freedom of motion about at least the two axes. The proximate end of the second arm 234 is coupled to the base 220. In some embodiments, the distal end of the first arm 234 may be rotatably coupled to the base (e.g., via ball-socket coupling, rotary joint, etc.), allowing the second arm 234 to rotate about at least one axis (e.g., the Y-axis). Thus, the coupling mechanism may provide various degrees or directions of motion of the sensing device 210 by allowing the sensing device to rotate about at least one axis relative to the first arm 232, rotation of the first arm 232 about the second arm 234 about at least two axis, and rotation of the second arm 234 about the base 230 about at least one axis (e.g., rotation by an angle of at least 180 degrees about of X, Y, and/or Z-axis as well as displacement of the sensing device 210 proximate to, and distal from the base 220 to allow the sensing device to be disposed on the patient for measuring the patient's JVP, and returned to the base 220 once measurements are complete).

FIG. 3B is a schematic block diagram of a coupling mechanism 230' configured to communicatively couple the sensing device 210 to the base 220, according to an embodiment. The coupling mechanism 230' may include an electrical lead, an electrical wire, a flat cord, a coiled cord, or any other suitable wire configured to physically as well as communicatively couple the sensing device 210 to the base 220. Thus, the coupling mechanism 230' may be highly flexible allowing the patient to freely move the sensing device 210 relative to the base 220 (e.g., similar to moving a handset of a landline phone from a base thereof). Such a configuration may reduce the weight of a system including the sensing device 210 and the base 220, thereby increasing portability as well as ease of use by the patient.

FIG. 3C is a schematic block diagram of a coupling mechanism 230" configured to communicatively couple the sensing device 210 to the base 220, according to an embodiment. Different from the coupling mechanisms 230 and 230', the coupling mechanism includes wireless coupling that communicatively couples the sensing device 210 to the base 220 (e.g., similar to a wireless handset of a landline phone communicatively coupled to base of the phone), but is not physically coupled thereto. In some embodiments, the coupling mechanism 230" may include wireless transceiver (e.g., a half-transceiver, a full-duplex transceiver, an RF transceiver, an optical transceiver, ethernet transceiver, a WI-FIR transceiver, a NFC transceiver, any other suitable wireless transceiver or a combination thereof) to send to and/or receive signals from the base 220 (e.g., activation signals, deactivation signals, image data, accelerometer 114 data, sensor(s) data, or any other data). In some embodiments, the sensing device 220 may include a power source (not shown) and a wireless charging mechanism (e.g., wireless charging coils) configured to receive an electromagnetic charging signal from a corresponding wireless charging mechanism (e.g., corresponding wireless charging coils) that may be included in the base 220. Wireless coupling may further increase portability, for example, allowing a patient to carry the sensing device 210 during travel without having to carry the base 220 with the patient.

Figure 4:
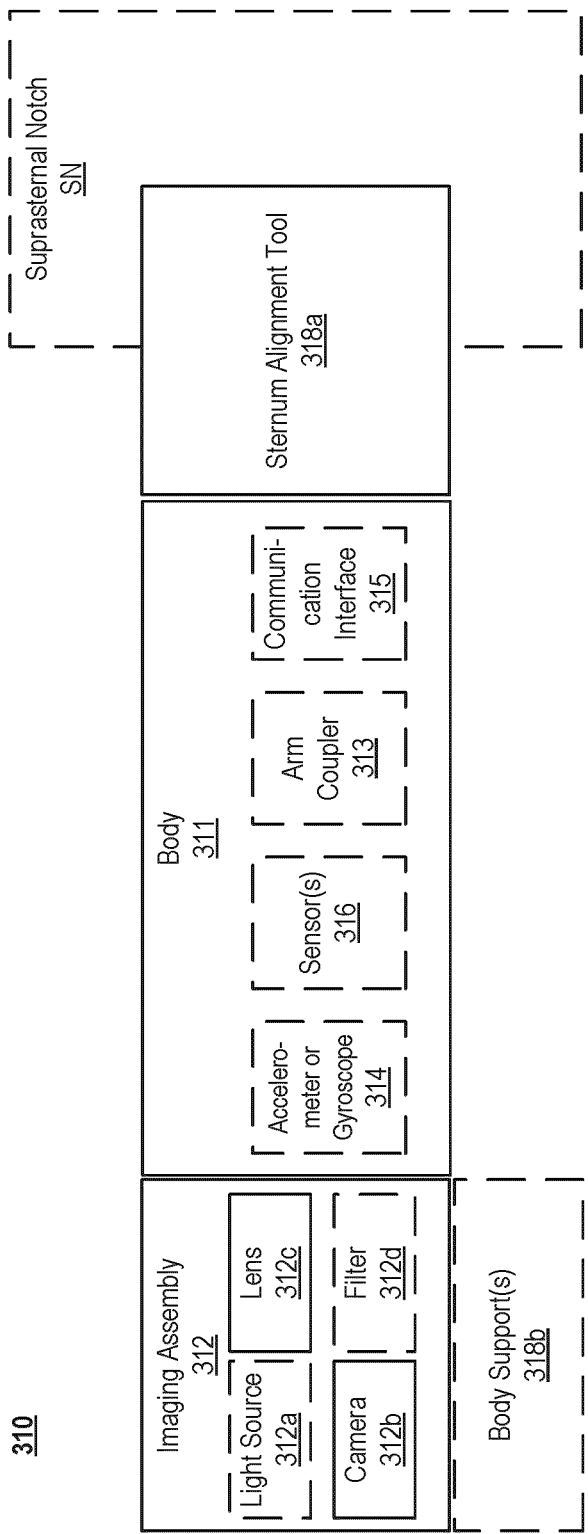
FIG. 4 is a schematic block diagram of a sensing device for measuring a patient's JVP disposed on a suprasternal notch (SN) of a patient, according to an embodiment.

FIG. 4 is a schematic block diagram of a sensing device 310 for measuring a patient's JVP disposed on a suprasternal notch SN of a patient, according to an embodiment. In some embodiments, the sensing device 310 may be physically and/or communicatively coupled to a base (e.g., any of the bases described herein) using a coupling mechanism (e.g., any coupling mechanism described herein). As shown in FIG. 4, the sensing device 310 include a body, an imaging assembly 311, a sternum alignment tool 318a, and optionally, a body support 318b.

Expanding further the body 311 may be ergonomically shaped to facilitate gripping of the body by a patient for manipulating the sensing device 310. For examine, the body 311 may include an elongated member defining one or more curvatures, grooves, notches, indents, etc., to provide an ergonomic grip for the patient to engage or otherwise, grip the body 311 and thus, the sensing device 310. The body 311 may define an interval volume within which at least some components of the sensing device 310 may be disposed. For example, as shown in FIG. 4, the sensing device may include an accelerometer or gyroscope 314, sensor(s) 316, and a communication interface 315 disposed within the internal volume. In some embodiments, the body 311 may, optionally, include, define, or have coupled thereto an arm coupler 313.

The accelerometer or gyroscope 314 and the sensor(s) 316 may be substantially similar to the accelerometer or gyroscope 114 and the sensor 116, respectively described with respect to the sensing device 110 and therefore, not described in further detail herein. The communication interface 315 can be any suitable device(s) and/or interface(s) that can communicate with a base (e.g., any of the bases described herein), a network (e.g., a LAN, a WAN, or the cloud), or an external device (e.g., a user device such as cell phone, tablet, a laptop or a desktop computer, etc.). Moreover, the communication interface 315 can include one or more wired and/or wireless interfaces, such as, for example, Ethernet interfaces, optical carrier (OC) interfaces, and/or asynchronous transfer mode (ATM) interfaces.

In some embodiments, the communication interface 315 can be, for example, a network interface card and/or the like that can include at least an Ethernet port and/or a wireless radio (e.g., a WI-FI® radio, a BLUETOOTH® radio, cellular such as 3G, 4G, 5G, etc., 802.11X Zigbee, etc.). In some embodiments, the communications interface 315 can include one or more satellite, WI-FI, BLUETOOTH, or cellular antenna. In some embodiments, the communications interface 315 can be communicably coupled to an external device that includes one or more satellite, WI-FI, BLUETOOTH, or cellular antenna, or a power source such as a battery or a solar panel. In some embodiments, the communications interface 315 can be configured to receive imaging or video signals from the imaging assembly 312, the movement or positioning signals from the accelerometer 314, and/or sensor data from the sensor(s) 316. In some embodiments, the communication interface 315 may also be configured to communicate signals to the imaging assembly 312, for example, an activation signal to activate the imaging assembly 112 (e.g., activate one or more light source(s) 312a or camera(s) 312b included in the imaging assembly 312), the accelerometer 314, and/or the sensor(s) 316.

The imaging assembly 312 is coupled to, installed in, or otherwise located at a distal end of the body 311 (e.g., an end for positioning in a notch SN of a patient). The imaging assembly 312 includes a camera(s) 312b, one or more lens 312c, and optionally, a light source 312a and/or a filter(s) 312(d). The light source 312a may include any source that projects electromagnetic radiation, for example, on to a target portion of the patient's body (e.g., the patient's neck), for example, visible light, infrared, NIR light, ultraviolet (UV) light, or any suitable combination thereof. The light source 312a may be configured to illuminate the target portion of the patient's body, and/or project a reference image onto the target portion, as previously described herein.

The camera 312b may include any suitable image capture device, for example, a CCD camera configured to capture the image(s) and/or video of the portion of the body of the patient. In some embodiments, the lens(es) 312c may include one or more concave and/or convex lenses configured to allow optical focusing of the target portion of the user's body by the camera(s) 312b to capture a clearer image of the target portion. The filter(s) 312d may include one or more physical filters, for example, optical filters (e.g., absorptive or interference filters) coated on the lens(es) 312c and/or software filters, and may include high pass filter(s), low pass filter(s), bandpass filter(s), etc., to allow capturing of a clear image(s) or video of the portion of the patient's body and filter out noise.

In some embodiments, the sensing device 310 may optionally include the body support(s) 318b. In some embodiments, the body support(s) 318b may optionally be coupled to the imaging assembly 312. Alternatively, one or more body support(s) 318b may be coupled at one or more locations along a length of the body 311 of the sensing device 310. In some embodiments, the body support 318b can include a support structure that can be placed in contact with a body of the patient, e.g., to facilitate supporting and/or positioning the sensing device 310 on a body of the patient. For example, the body support(s) 318b can include a patient chest rest that can be sized and/or shaped to rest on the patient's chest when the sensing device 310 (and therefore the imaging assembly and other components of the sensing device 310) are properly positioned on a patient, e.g., for operation. In some embodiments, the body support 318b can include one or more sensor(s) (e.g., sensor(s) 316 for measuring one or more physiological parameters or other conditions of a patient). In some embodiments, the body support 318b may include a ring-shaped structure coupled to the distal end of the body 311 (e.g., screwed, snap-fit, or friction fit therein). The body support 31b may be formed from any suitable strong and rigid material, for example, metal, plastics, polymers, etc.

The sternum alignment tool 318a is coupled to or formed on a proximate end of the body 311 and configured to facilitate positioning of the sensing device 318 on a suprasternal notch SN of the patient. In some embodiments, the sternum alignment tool 318a may include, have, or define a spherical portion (e.g., a hemispherical shaped projection coupled to the body 311 or monolithically formed in the body 311) dimensioned to fit within the notch. In some embodiments, the sternum alignment tool 318a may include an interchangeable or adjustable patient-contacting element, e.g., allowing it to be customized to the patient (e.g., to accommodate a change in size, a change in anatomic location, etc. between patients) to aid in positioning the sternum alignment tool 318a on the patient's suprasternal notch SN. When the sensing device 310 is properly positioned on the patient, with the sternum alignment tool 318a positioned within the suprasternal notch SN, the imaging assembly 312 can be suitably positioned relative to the portion of the patient's body (e.g., the neck), e.g., for capturing video that can be used to determine the patient's JVP.

In addition, or in the alterative, in some embodiments the sternum alignment tool 318a has at least one adjustable patient-contacting element. Where present, an adjustable patient-contacting element also may assist in positioning the locator object on the patient's torso. In other embodiments, in addition or in the alternative to the foregoing, the entire sternum alignment tool 318a may be an interchangeable element, for example, to serve a similar purpose.

Positioning the sternum alignment tool 318a on the suprasternal notch SN of the patient positions the imaging assembly 312 in a desired position or orientation with respect to the target portion (e.g., the neck) of the patient, e.g., to allow the imaging assembly 312 to capture image(s) and/or video of the patient so as to be able to capture distention of the patient's IJV and thereby, the patient's JVP. The imaging assembly 312 can capture images and may communicate the images to a base (e.g., the base 120), for example, via the communication interface 315.

In some embodiments, the body 311, body support(s) 318b, and/or the sternum alignment tool 318a may also include a reference element coupled thereto (e.g., any reference element as previously described herein). For example, the body 311, body support(s) 318b, and/or the sternum alignment tool 318a may include a portion that is positioned (or positionable) within a field of view of the imaging assembly 312 when the imaging assembly 312 is positioned for image capture of the patient's IVJ. In some embodiments, the sternum alignment tool 318a can function as the reference element. In some embodiments, one of the body 311, body support(s) 318b, and/or the sternum alignment tool 318a can include an extendable or adjustable element (e.g., an arm). The adjustable element may be adjustable so that when the sensing device 310 is disposed on the patient's torso, a length of the adjustable element may be adjusted to position at least a portion of it proximate to the patient's neck and within a field of view of the imaging assembly 312.

Figure 5:
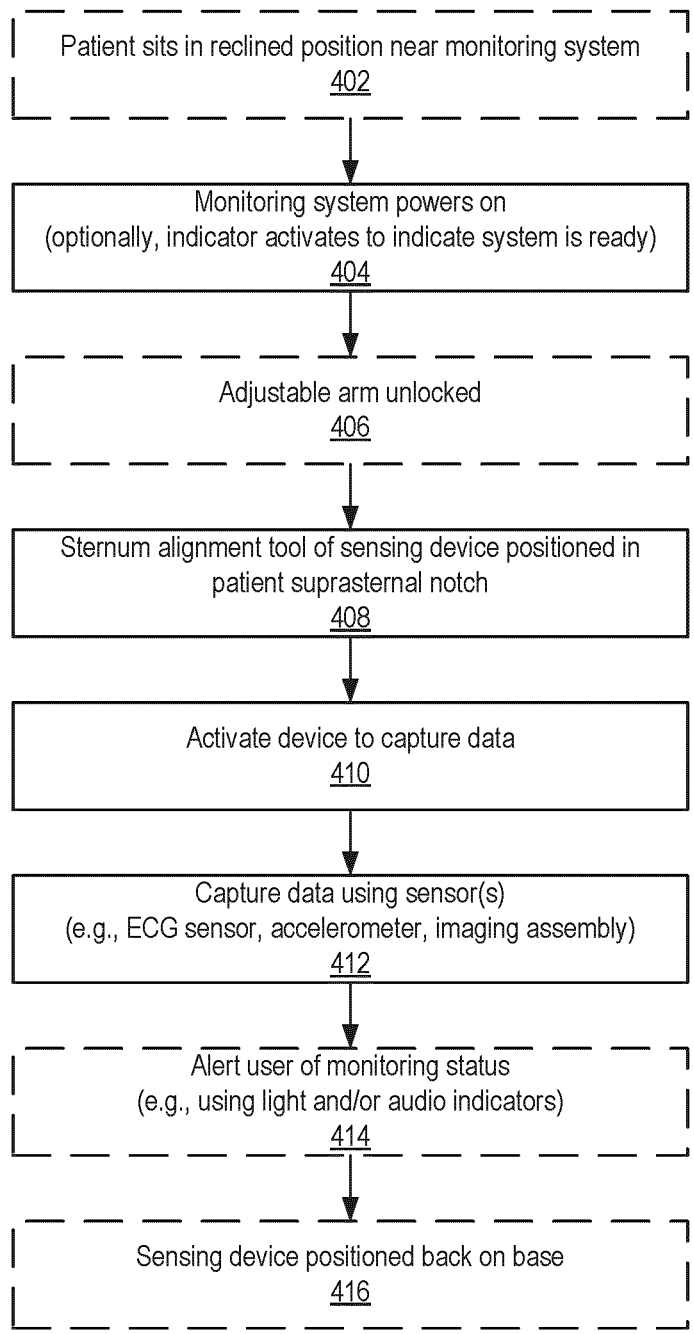
FIG. 5 is a schematic flow chart of a method for measuring JVP of a patient using a system that includes a sensing device and a base, according to an embodiment.
Figure 6:
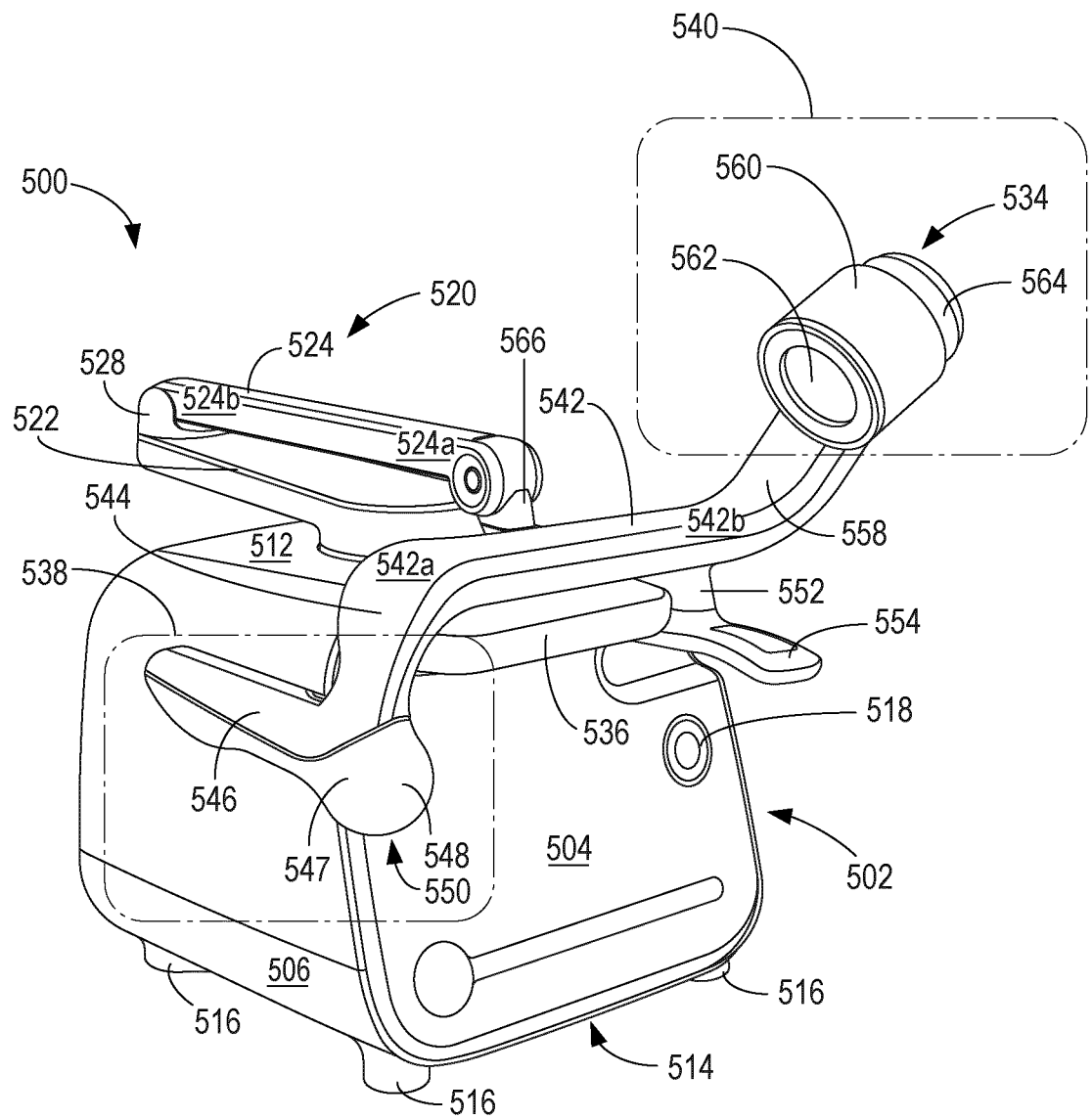
FIG. 6 shows an isometric view of a device for capturing video of the neck of a human patient suitable for monitoring the JVP of the patient, according to an embodiment. The device is shown in its stored configuration. The isometric view is taken of the top, front and right sides of the device.
Figure 7:
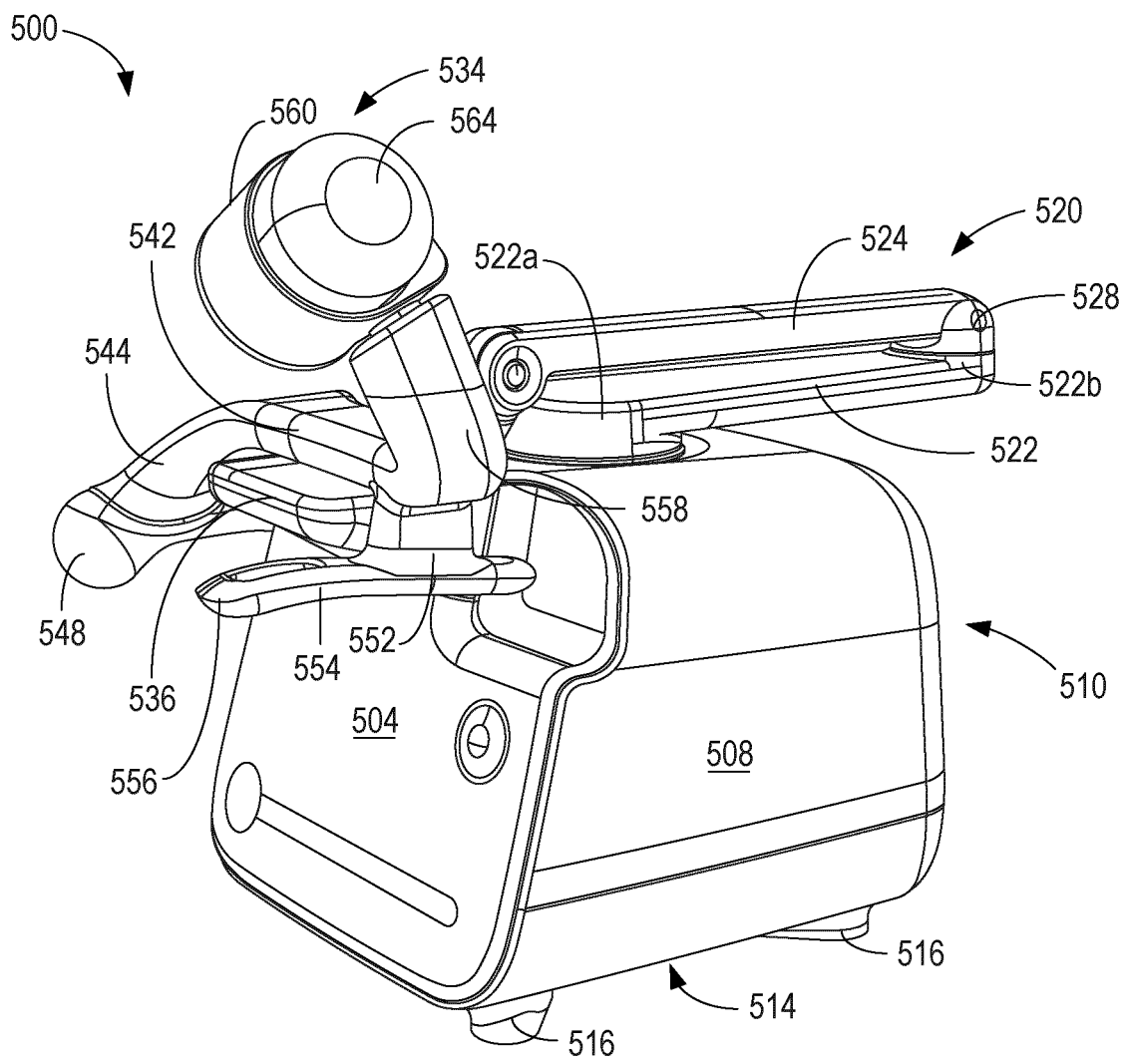
FIG. 7 shows an isometric view of the device shown in FIG. 6, taken of the top, front and left sides of the device.
Figure 8:
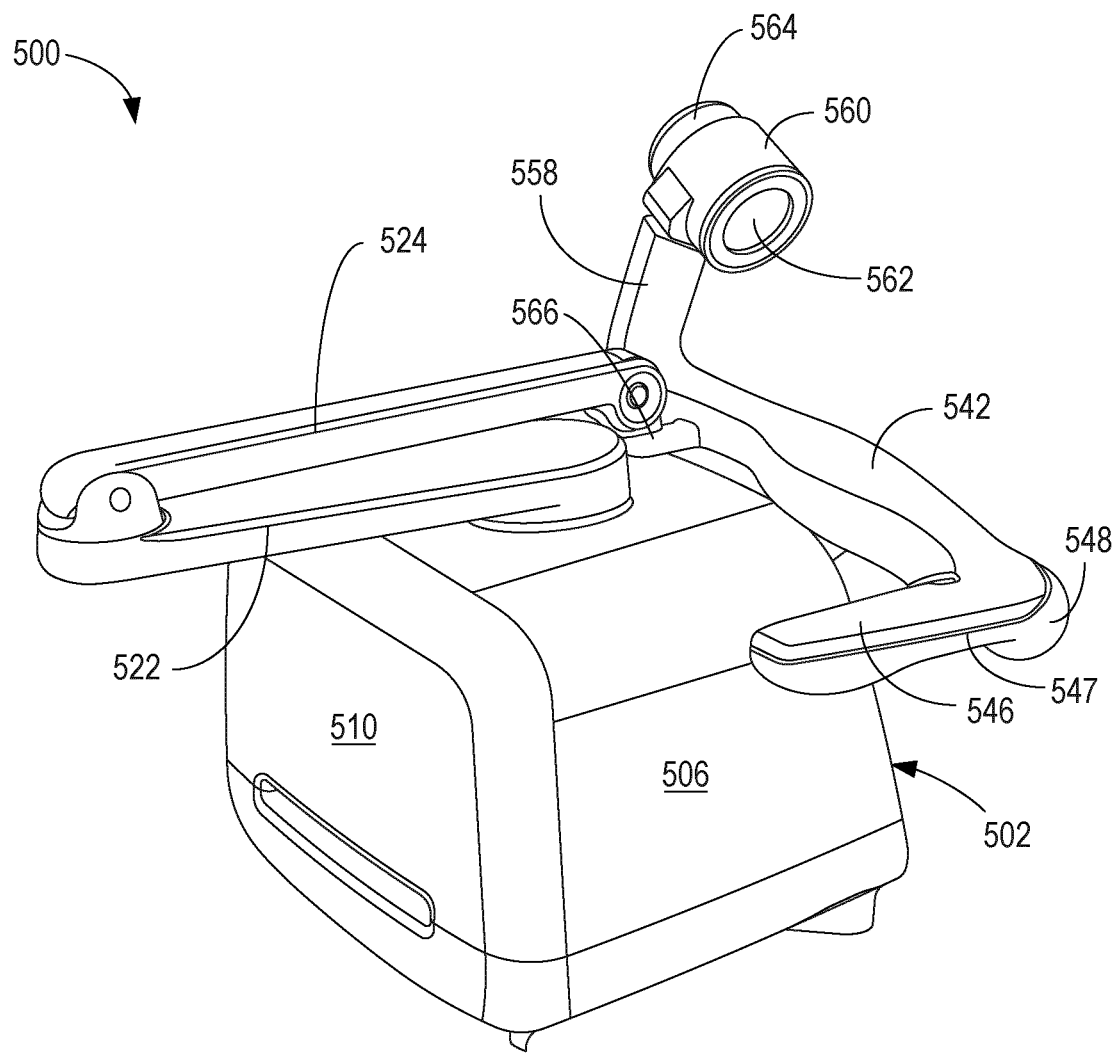
FIG. 8 shows an isometric view of the device shown in FIG. 6, taken of the top, rear and right sides of the device.

FIG. 5 is a schematic flow chart of a method 400 for measuring JVP of a patient using a monitoring system (e.g., the system 100, 100', or any other system described herein), that includes a sensing device (e.g., the sensing device 110, 110', 210, 310, or any other sensing device described herein) and/or a base (e.g., the base 120, 220, or any other base described herein), according to an embodiment. While the method 400 is described with respect to a particular configuration of the system 100 including the sensing device 110 and the base 120, they are equally applicable to any other system including any sensing device or base described herein. All such embodiments are contemplated and should be understood to be within the scope of this disclosure.

In some embodiments, monitoring can be performed using the monitoring systems described herein based on a preset schedule. For example, monitoring can be performed once per day, twice per day, three times per day, once per hour, etc. Depending on the specific application, a physician or other healthcare professional can prescribe a schedule for the patient to perform monitoring (e.g., of the JVP).

At 402, a patient can sit in a reclined position near the monitoring system 100. For example, the patient's torso may be reclined at an angle in a range of about 10 degrees to about 90 degrees, including all sub-ranges or values therebetween, such as, for example, between about 30 degrees and about 60 degrees. At 404, the monitoring system 100 powers on. For example, the patient or an operator of the monitoring system may engage an activation button or switch to turn on the system 100. In some embodiments, powering the system ON may also optionally turn on an indicator (e.g., an audio and/or a visual indicator such as an LED light or display) indicating to the patient that the system 100 has powered ON and ready.

Optionally, in some embodiments in which the sensing device 110 is coupled to the base via a linkage assembly that includes an adjustable arm, the method 400 includes unlocking the adjustable arm, at 406. The adjustable arm may include the articulating arm 230, or any other articulating arm as described with respect to the monitoring system 100. The adjustable arm may be unlocked and manipulated to move the sensing device 110 proximate to a torso of the patient, e.g., by the patient, a user, or an operator of the monitoring system. In some embodiments, the adjustable arm can be a robotic arm that can be remotely manipulated by an operator, e.g., a physician, and/or be manipulated by a processor (e.g., autonomously based on pre-programmed instructions). At 408, a sternum alignment tool (e.g., the sternum alignment tool 318*a*) of the sensing device 110 is positioned by the patient or the operator on the suprasternal notch of the patient, as previously described herein. This also aligns the imaging assembly of the system 100 with the neck of the patient such that the IJV of the patient is within a field of view of the imaging assembly 112, as previously described herein. In some embodiments, when the sensing device 110 is held by a patient for placement of the sensing device 110, the hand of the patient that holds the sensing device 110 can be in contact with one or more sensors (e.g., ECG, PPG, etc.). The hand of the patient can maintain the sensing device 110 in position while in contact with such sensors.

At 410, the sensing device 110 is activated to capture video data of the neck of the patient. For example, the processor 124 of the sensing device 110 may be configured to detect, based on data received from the accelerometer 114 and/or the sensor(s) 116, that the sensing device 110 is suitably positioned on the torso of the patient (e.g., stably positioned and/or positioned at a suitable angle) and, therefore, initiate image and/or video capture. In some embodiments, a user can actuate a patient-actuated (or user-actuated) switch, e.g., to activate the sensing device to capture data. At 412, the sensing device 110 captures data using the imaging assembly 112, the sensor(s) 116, and/or the accelerometer or gyroscope 114. Such data may include, but is not limited to, ECG data, accelerometer or gyroscope data, imaging data, etc., as previously described herein.

As described above with reference to FIGS. 2-5, in some embodiments, the imaging assembly 112, the sensor(s) 116, and/or the accelerometer or gyroscope 114 can be configured to send the data (e.g., imaging data, ECG data, accelerometer or gyroscope data) to a processor, such as, for example, an onboard processor (e.g., a processor onboard the sensing device, such as processor 124') or a remote processor (e.g., processor in a base or other remote compute device). The processor can be configured to use the data to determine various physiological parameters of the patient. In some embodiments, the processor can be configured to determine the JVP height of the patient, as described above. In particular, the processor in an embodiment can be configured to identify a longitudinal axis or long axis of the patient's neck and to determine (e.g., approximate) an angle of the long axis of the neck, e.g., based on the imaging data. The angle of the long axis of the neck can be determined relative to an angle of the sensing device (e.g., sensing device 110, 110', etc.) or an angle of a portion of the sensing device (e.g., a reference element or positioning element). The angle of the sensing device relative to the vertical can be known or determined, e.g., based on the imaging data and/or the accelerometer or gyroscope data. As such, the angle of the long axis of the neck relative to the vertical can be determined. The processor can also be configured to determine a location of the sternal angle of the patient and a location of a highest point of pulsation of the IJV, e.g., based on imaging data and knowing that the sensing device has been properly positioned. The vertical height of the JVP can then be calculated, e.g., using trigonometry calculations. Further details of determining the angle of the long axis of the neck and the vertical height of the JVP are described with reference to FIG. 23.

In some embodiment, the method 400 may optionally include alerting a user or a patient of monitoring status of the system 100, at 414. The alerts may include any suitable alert, for example, a visual alert using a light source (e.g., a LED lamp) or an audio alert (e.g., using a speaker). The alerts can indicate to a user that a monitoring or measurement session is complete. In some embodiments, the alerts can also indicate to a user that there is an error with the monitoring or measurement session, e.g., thereby prompting a user to adjust the positioning of the sensing device and/or other components of the system to re-start the data capture at 410-412. At 416, the sensing device 110 is positioned back on the base 120. For example, once the processor 124 has determined that sufficient data has been captured to reliably measure the patients JVP, the processor 124 may be configured to generate the alert to inform the patient or the user that the data has been captured and the measurement session has ended so that the user may position the sensing device 110 back on the base 120. In some embodiments, the sensing device may not operate with a base, such as, for example, the sensing device 110' depicted in FIG. 2B, and therefore the sensing device is not placed back on a base by a user can place the sensing device on a secure surface (e.g., a table).

Referring to FIGS. 6-12, there is shown a device 500, e.g., for capturing video of the neck of a human patient suitable for monitoring the JVP of the patient, according to an embodiment. The device 500 can be an example of a monitoring system, such as, for example, any of the monitoring systems described herein (e.g., monitoring systems 100, 100', etc.). As such, the device 500 can include components or elements that are structurally and/or functionally similar to those of other systems described herein, including, for example, system 100, 100', etc.

Device 500 has three general components: a base 502, a positioning arm 520, and a camera and light unit 534. Each of these components is described in turn in detail below.

As depicted in the figures, the base 502 is approximately cube-shaped, and thus has a front side 502, a rear side 510, a right side 506, a left side 508, a top side 512, and a bottom side 514. The base 502 is designed to sit on a flat horizontal surface on legs 516 that extend downwardly from the bottom side 514 of the base 502. Although not shown in the drawings, as a skilled address would understand, the base 502 has sufficient weight so that it will remain in place during normal operation of the device 500 (as is described herein). That is, the base 502 is heavy enough such when the camera and light unit 534 (or imaging assembly) (i) is being moved from a storage position to its appropriate operating position on the torso of the patient to carry out monitoring of the patient's JVP, (ii) is in that appropriate operating position, and (iii) is being moved from that position back to its storage position, the base 502 does not move, become unstable, or tip.

The base 502 has an interior cavity inside, which can be accessible from the rear side 510, e.g., for maintenance and/or repair purposes. During the normal course of operation of the device 500, the interior cavity of the base 502 does not need to be accessed. The interior of the cavity contains the following components: a power supply, a computer processor (e.g., similar to processor 124) and related elements, computer memory (e.g., similar to memory 122), wiring, a wireless communications device(s) (e.g., similar to communication interfaces) 126, including, for example, cellular, WI-FIR), BLUETOOTH®, NFC, etc.), sensors, as well as any other necessary or desirable conventional components currently used in electronic devices (e.g., cellular and/or WI-FI antennas). This list is exemplary, not-limiting, as the skilled addressee understands the details of the design of conventional medical devices. In some embodiments, there may be a recess in the rear side 510 of the base 502 where standard connectors for power and communications can be located, e.g., USB/Thunderbolt™ ports, a socket for receiving the end of a power cord, etc. In some embodiments, the base 502 has plastic exterior with an interior metal frame. Alternatively, the base 502 can include an exterior made from any suitable structure that provide sufficient rigidity for containing the components therein.

Located on the front side 504 of the base 502 is a power button and power indicator 518. The power indicator is a lighted circle that surrounds the power button 518. The lighted circle is lit when the device 500 is powered on. Also located on the front side 504 of the base 502 is a shelf 536 extending from the front side 504. The shelf 536 provides a place to appropriately position and support the camera and light unit 534 when the camera and light unit 534 are in its storage configuration. (The camera and light unit 534 are shown in its storage configuration in FIGS. 6 to 12.).

The right side 506 and the left side 508 of the base 502 of the device 500 are plain and featureless. (Which will not be the case in all embodiments of the present technology).

Attached to and extending from the top side 512 of the base 502 of the device 500, is the moveable pivot arm 520. The moveable pivot arm 520 has two major members, a lower arm member 522 and upper arm member 524. Each of arm members 522, 524 is elongate with a generally rectangular cross-section. The lower arm member 522 has a forward end 522a and rearward end 522b. The upper arm member 524 also has a forward end 524a and a rearward end 524b. (The forward ends 522a, 524a and the rearward ends 522b, 524b of the arm members 522, 524 (respectively) are defined consistently when the pivot arm 520 is its storage configuration, shown in FIGS. 6 to 12).

As can be seen in FIGS. 6 to 12, the forward end 522a of the lower arm member 522 is pivotably attached to the top side 512 of the base 502. This pivotable attachment allows the lower arm member 522 to pivot both clockwise and counter-clockwise about the when the base 502 is viewed from above with the pivot arm 520 in its storage configuration.

The rearward end 522b of the lower arm member 522 is pivotably attached to a pivot member 128. This pivotable attachment allows the pivot member 528 to pivot both clockwise and counter-clockwise about the location 520 when the base is viewed from above with the pivot arm 520 in its storage configuration.

The rearward end 524b of the upper arm member 524 is also pivotably attached to the pivot member 528. This pivotable attachment allows the upper arm member 524 to pivot clockwise and counter-clockwise when the base 502 is viewed from either the left side 508 or the right side 506 with the pivot arm 520 in its storage configuration. Thus, with respect to the rear end 522b of the lower arm member 522, rear end 524b of the upper arm member 522 can pivot about two different pivot axes simultaneously owing to the presence and structure of the pivot member 528.

The forward end 524a of the upper arm member 524 is pivotably attached to connecting member 566 which is part of the camera and light unit 534 at location. This pivotable attachment allows the camera and light unit 534 to pivot clockwise and counterclockwise with respect to the forward end 524a of the upper arm member 524 when the base 502 is viewed from either the left side 508 or the right side 506 with the pivot arm 520 in its storage configuration.

The camera and light unit 534 has a main horizontal member 542 is elongate with two ends, a patient-contacting end 538 and the camera end 540. The patient-connecting end 538 is at the right side 542a of the main horizontal member 542. The camera end 540 is at the left side 542b of the main horizontal member 542. As can be seen in FIGS. 6 to 12, when the pivot arm 520 and the camera and light unit 534 are in their storage configuration, the main horizontal member 542 of the camera and light unit 534 rests on the shelf 536 extending from the front side 504 of the base 502.

Figure 12:
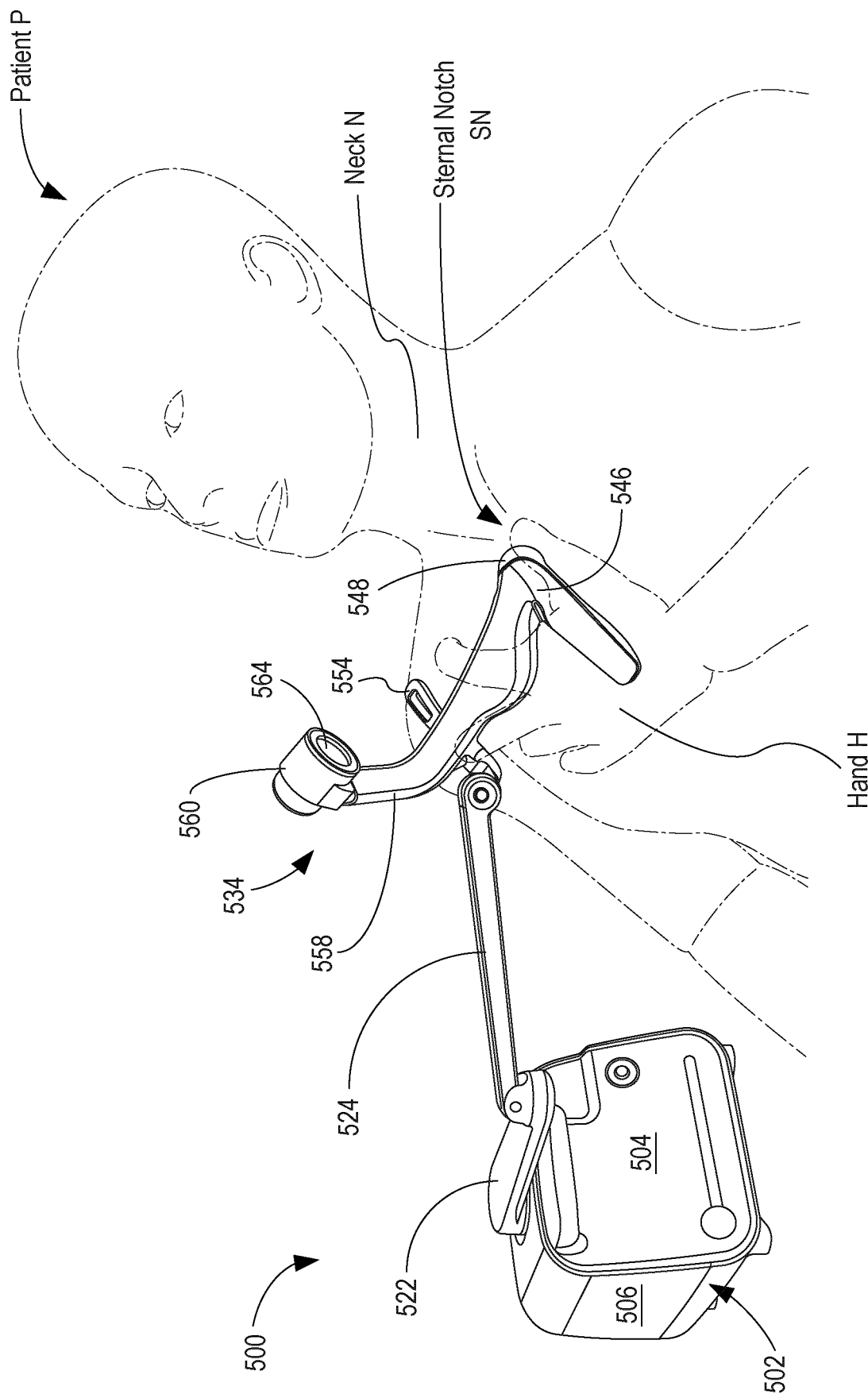
FIG. 12 shows a schematic view of a patient having placed the camera and light unit of the device of FIG. 6 on their torso in an appropriate operational position, taken from a first angle.

The patient-contacting end 538 of the main horizontal member 542 has a sternum alignment tool 546. The sternum alignment tool 546 is connected to main horizontal member 542 via a mounting arm 544 that extends outwardly and downwardly from the right side 542a of the main horizontal member (e.g., see FIG. 10). The sternum alignment tool 546 extends perpendicularly to the mounting arm 544 and the main horizontal member 542. Thus, the sternum alignment tool 546 extends from the front side 504 of the base 502 towards the rear side 506 of the base (e.g., FIG. 3). When the camera and light unit 534 is being moved into its operational configuration, the sternum alignment tool 546 is used to properly position the camera and light unit 534 by using the sternum alignment tool 546. In this respect, the underside of the sternum alignment tool 547 has an interchangeable contoured patient-contacting element 547 that has been selected such the contours of the element fit with the particular patient using the device 500. The forward end 550 of the element 547 has a spherical portion 548 that is sized to snugly fit with the patient's suprasternal notch 594 (FIG. 12). Thus, in this embodiment of the present technology, the spherical portion 548 of the forward end 550 of the contoured patient-contacting element 547 serves as a locator object or positioning element as was described hereinabove. The portion of the contoured element 547 rearward of the forward end 550 is also contoured to fit the patient's sternum, e.g., below the suprasternal notch, when the alignment tool 546 is properly aligned so as to be parallel with the patient's sagittal (longitudinal) plane (with the spherical portion 548 fitting within the patient's suprasternal notch SN).

Figure 10:
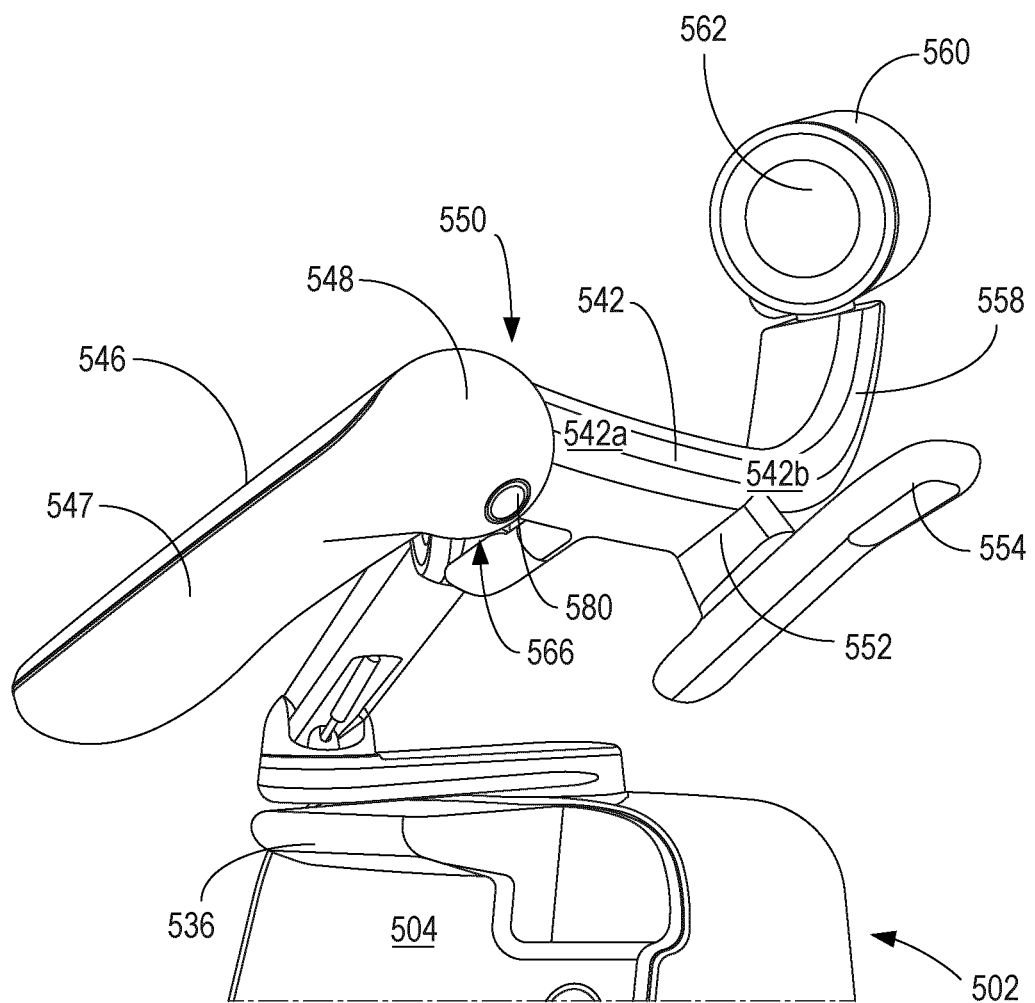
FIG. 10 shows an isometric view of the top, front and left sides of the device of FIG. 6 in the operational configuration shown in FIG. 9.

As can be seen in FIG. 10, the underside of the spherical portion 548 of the forward end 550 of the contoured patient contacting element 547 has a sensor unit 580. The sensor unit 580 has two sensors, an inner circular-shaped PPG sensor, and an outer ring-shaped ECG electrode surrounding the PPG sensor. When the spherical portion 548 is snugly fit within the patient's suprasternal notch SN, the sensors of the sensor unit 580 contact the patient's skin and can measure one or more physiological parameters or conditions of the patient. The sensor unit 580 is in electronic communication with the computer processor within the base 502 of the device 500.

Figure 11:
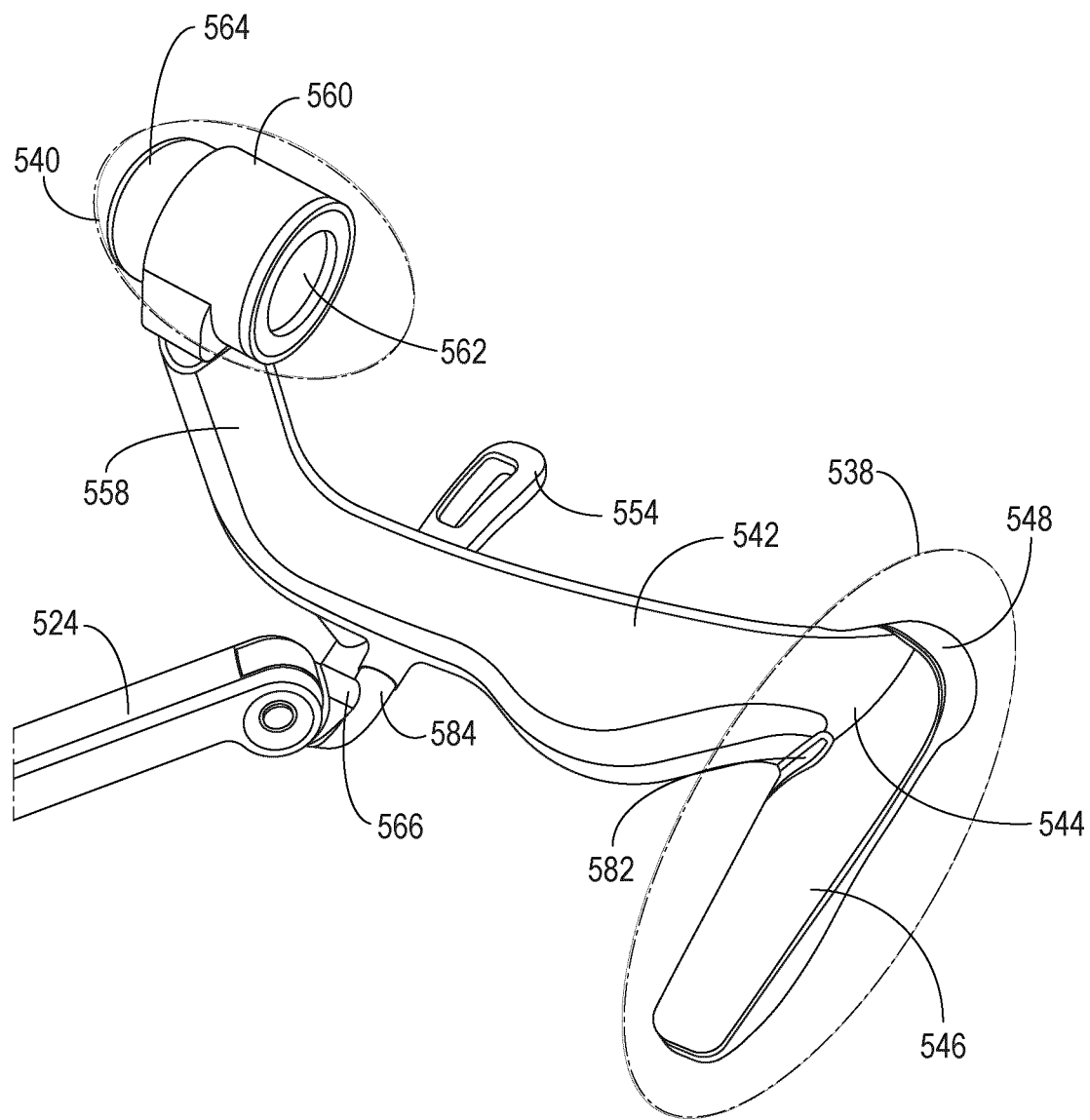
FIG. 11 shows an isometric close-up view of the camera and light unit of the device of FIG. 6, taken from the top, right, rear of the camera and light unit.

As can be seen in FIG. 11, located on the top side of the alignment tool 546 can be a second ECG electrode 582. It is foreseen that when the camera and light unit 534 is properly positioned on the torso of the patient in the operating position (see FIG. 12), the hand H of the patient P will be placed on the sternum alignment tool, with the patient's skin in contact with the ECG electrode 582. Thus, both of the ECG electrode of the sensor unit 580 and the ECG electrode 582 on the top side of the alignment tool 546 are in contact with the patient's skin when the device 500 is operational, allowing for ECG readings to be taken be the device 500. The ECG electrode 582 is in electronic communication with the computer processor within the base 502 of the device 500 (wiring not shown in the figures).

The camera end 540 of the main horizontal member 542 has a patient chest-rest 554 and a camera 560. The patient chest-rest 554 is attached to a mounting member 552 that extends downwardly from the left side 542b of the main horizontal member 542 of the camera and light unit 534. The patient chest-rest 554 is sized and shaped to rest on the patient's chest when the camera and light unit 534 is properly positioned on the patient's torso when the unit 534 is in its operational position (e.g., FIG. 12) to assist in positioning the unit 534 and maintaining its stability. Thus, the patient chest-rest 554 may serve as a second positioning element.

The camera 560 is connected to the main horizontal member 542 via a mounting arm 558 that extends outwardly and upwardly from the left side 542b of the main horizontal member 542 member of the camera and light unit 560. The camera 560 is pivotably mounted to the end of the mounting arm 558. The camera 560 has an aperture 562 through which images are taken. The camera 560 may be equipped with a light or NIR emitter in the form of a ring surrounding the aperture 562. In some embodiments, where a NIR emitter is used, a visible light emitter (e.g., in the form of a ring) can be included to provide an indication to a user that the NIR is on or active while not being visible to the user. The camera 160 (and the light/NIR emitter, if present), are in electronic communication with the computer processor within the base 502 of the device 500.

Extending rearward from the main horizontal member 542 is the connecting member 566, referred to above. The connecting member 566 is pivotable with respect to the main horizontal member 542, allowing the camera and light unit 534 to pivot clockwise and counter-clockwise when viewed from above.

An accelerometer and/or gyroscope (not shown) is located within the camera and light unit 534 and is in electronic communication with the computer processor within the base 502 of the device 500. Signals from the accelerometer and/or gyroscope are used to determine the angle of the camera and light unit 534 (and thus the angle of the patient) with respect to a horizontal reference axis or plane.

The device 500 can be set-up prior to its use for the first time by a clinician or other trained healthcare professional. As part of the set-up process, the clinician can select an appropriate interchangeable contoured patient-contacting element 547 that is properly sized and shaped to the particular anatomy of the patient P (e.g., the spherical portion 548 is properly sized to fit snugly within the patient's suprasternal notch SN (see FIG. 12). The clinician also pivots the camera 560 (e.g., about a pivot location) as needed to ensure that both the patient's neck N and the forward end 650 (including the spherical portion 548) of the sternum alignment tool 546 are within the camera's frame (e.g., such that images/video taken by the camera 560 show both). The clinician then locks the camera's position into place so that it cannot be inadvertently altered by the patient P.

In the device 500, the spherical portion 548 of the forward end 550 of the sternum alignment tool 546 is of a known size and shape. Thus, in addition to serving as a locator object as described above, the spherical portion 548 also serves as a reference element as described above. Although not shown in the figures, in some embodiments, the spherical portion 548 may have a scale of measurement thereon to assist in making its use as a reference element (e.g., to facilitate calculations of the relative positioning of the patient's anatomical features (suprasternal notch SN and the IJV)).

At home (or any at other location where JVP monitoring using the device 500 will take place), the device 500 is placed on a flat surface (e.g., FIG. 12) and plugged in to a power outlet. The patient P then sits in an inclined position next to the flat surface on which the device 500 has been placed. The patient then pushes the power button 518 and the indicator illuminates to indicate that the device 500 is powered on and ready for use.

Referring to FIG. 12, the camera and light unit 534 can then be gripped by the patient P. Typically, the patient P grips the sternum alignment tool 546 when moving the camera and light unit 534, although other parts of the main horizontal member 542 may be gripped as well. This allows the patient P to move the camera and light unit 534 from its stored configuration (FIGS. 6-8) via the pivoting and repositioning of the pivot arm 520 and the various other pivotable and/or moveable components described hereinabove.

Figure 9:
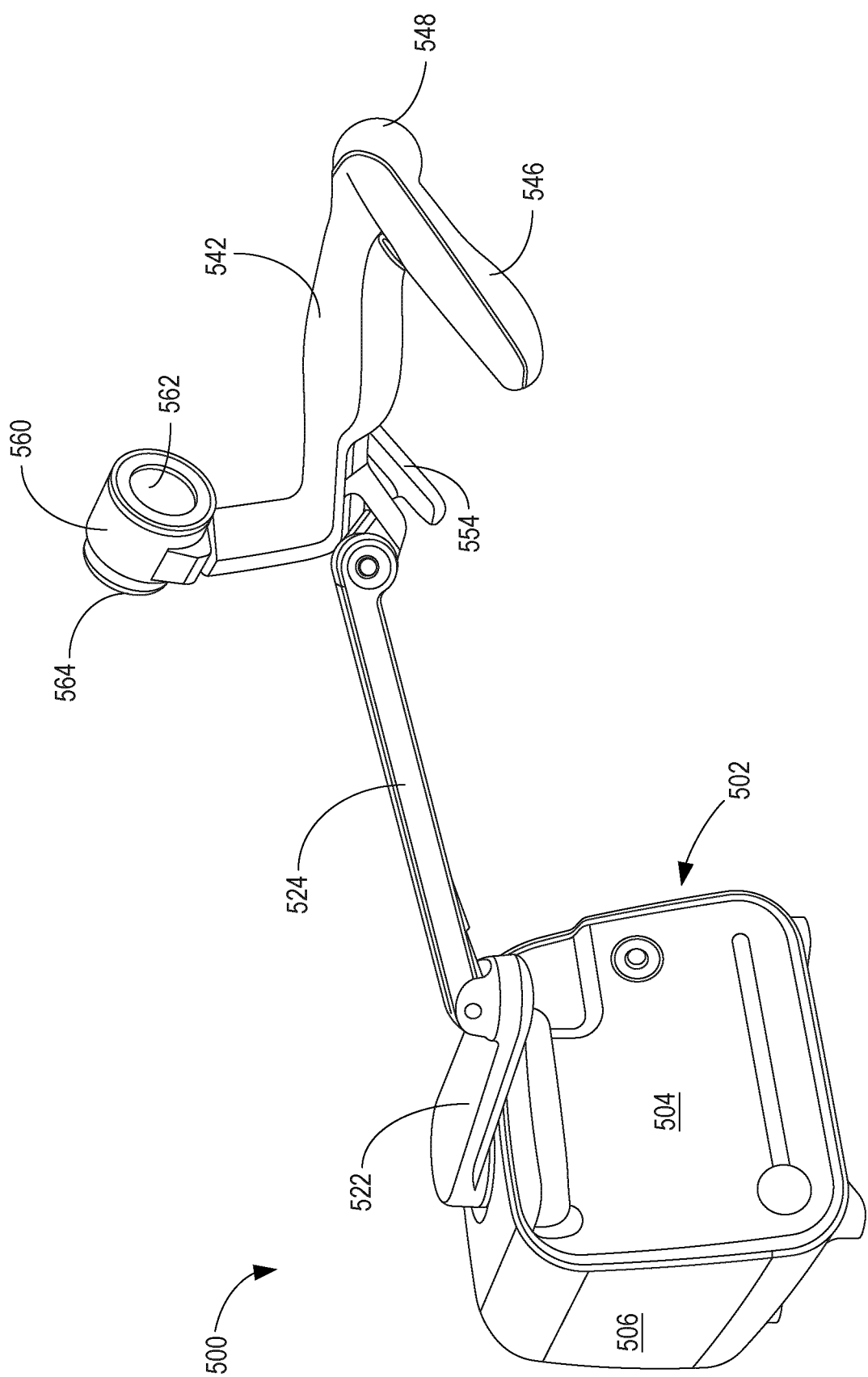
FIG. 9 shows an isometric view of the top, front and right sides of the device of FIG. 6, with the device shown in an operational configuration.

In FIGS. 9 and 12, the pivot arm 520 has been pivoted and repositioned to be in its appropriate operating position/configuration. The patient P does this by moving the camera and light unit 534 in space until the spherical portion 548 of the forward end 550 of the sternum alignment unit 546 fits snuggly within the patient's suprasternal notch SN and the sternum alignment unit 546 is aligned with the sternum 598 of the patient P (as described above). Owing to the correct positioning of the camera and lighting unit 534 during the set-up of the device by the clinician, the camera 560 is appropriately positioned in the correct position to take images/videos of the patient's neck N and the spherical portion 548 when the patient P has correctly positioned the camera and light unit 534 in the appropriate operating position. The patient P does not adjust the camera 560.

Once the patient P has appropriately positioned the camera and light unit 534, the patient P then places their hand H on the ECG electrode 582 in the position shown in FIG. 12. The device 500, being powered on, is monitoring input from the sensor unit 580, ECG electrode 582 and the accelerometer within the camera and light unit 534. Once the device 500 has received input from the accelerometer that the camera and light unit 534 is not moving; and has received appropriate input from the sensor unit 580 and the ECG electrode 582 that it is possible to monitor the PPG and the ECG of the patient P, the device 500 starts the monitoring session and captures video from the camera 560 and stores the video in the device's computer memory. Alternatively, a user (e.g., patient) can actuate a patient or user-actuated switch when the sensing device is appropriately positioned, and the device can wait from a predetermined period of time (e.g., between about 1 second to about 10 seconds) before activating the imager to start recording or measuring using the sensor(s) and/or imager. The device 500 may be configured to emit an audible signal from its speaker when the monitoring session (and the recording) have begun and when the monitoring session (and the recording) have ended, to signal to the patient that the monitoring session has been successfully started and completed. Once the monitoring session has ended, the patient P grips the camera and light unit 534, moves it back to the storage configuration and presses the power button 518 to turn off the device 500.

The stored video may then be sent to a clinician for analysis by any conventional means: e.g., via a communication interface (e.g., communication interface 126), via the Internet if the device 500 is so configured and is connected to the Internet, via the video's extraction from the device 500, via a smartphone (or other device) and then subsequent transmission to the clinician over the Internet, via the video's extraction from the device 500 on a USB key which is then physically given to or sent to the clinician for analysis, etc. Alternatively or additionally, the stored video can be processed and the JVP signals extracted and displayed to a clinician for viewing (e.g., as an image, video, etc.).

The monitoring process is then repeated by the patient, e.g., P according to a schedule prescribed by the clinician.

Figure 13:
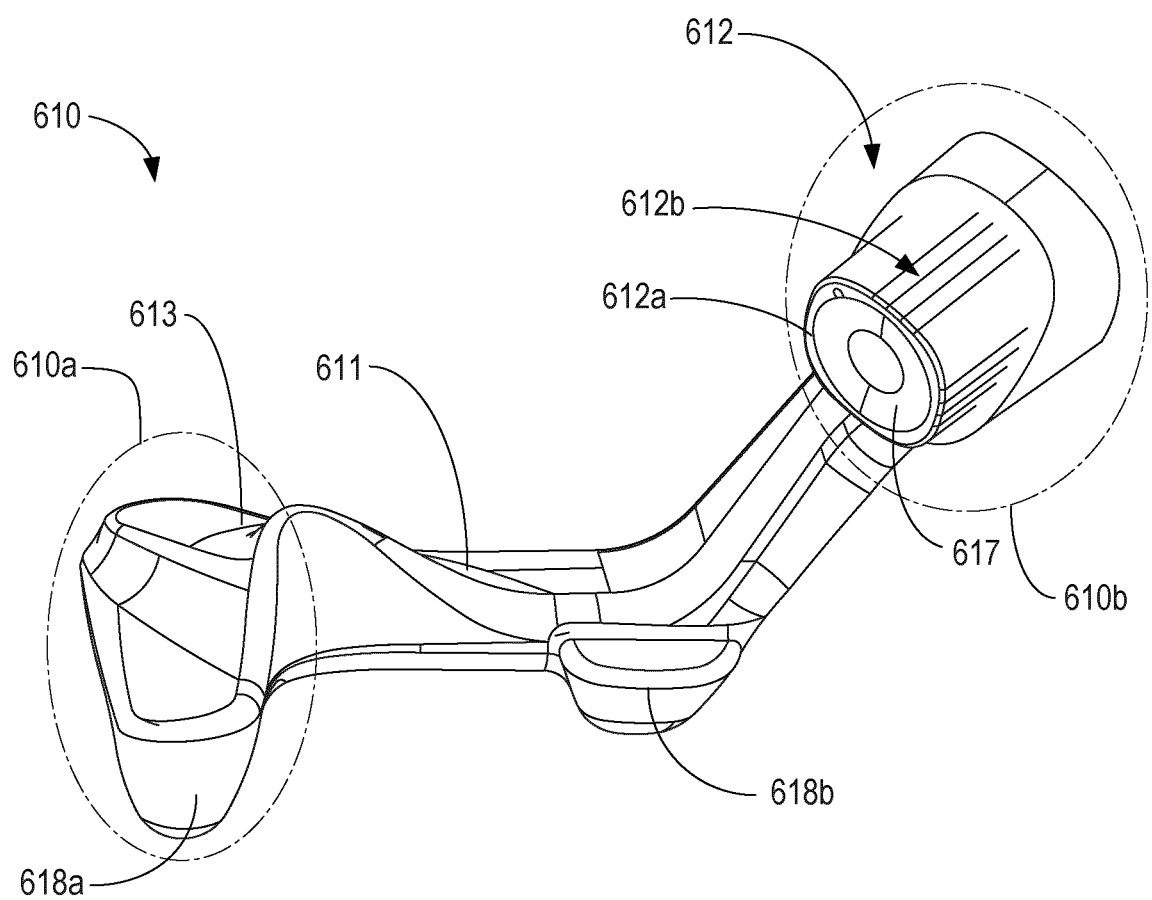
FIG. 13 is a front elevation view of a sensing device for measuring a patient's JVP, according to an embodiment.
Figure 14A:
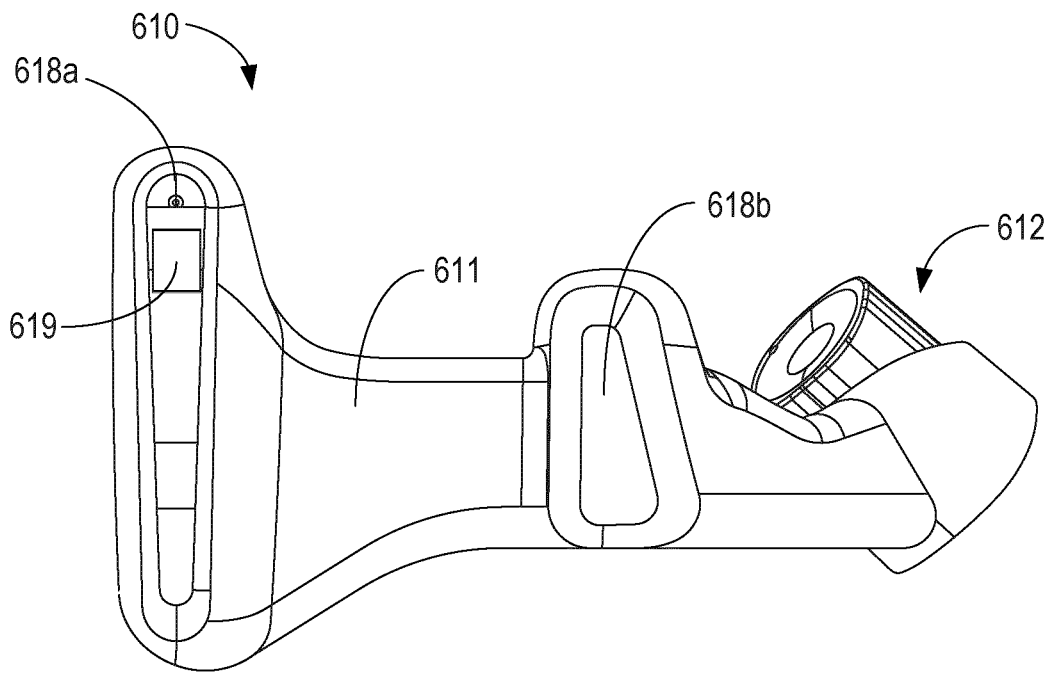
FIG. 14A is a bottom view of the sensing device of FIG. 13.
Figure 14B:
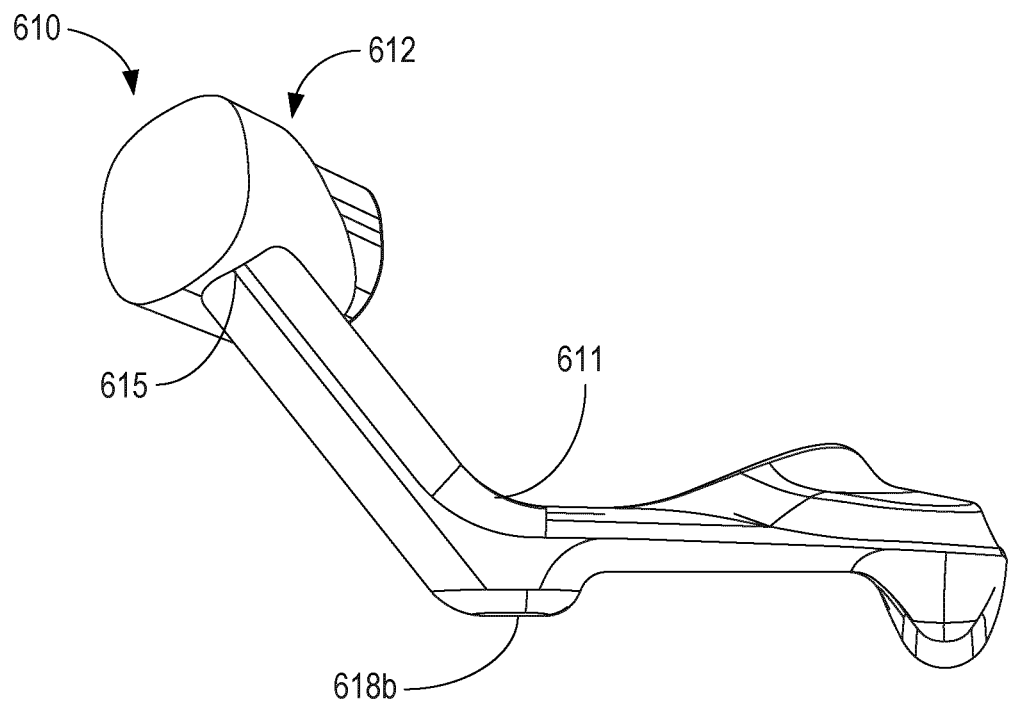
FIG. 14B is a rear elevation view of the sensing device of FIG. 13.

FIGS. 13-14B are various views of another sensing device 610, according to an embodiment. In some embodiments, the sensing device 610 may be usable for capturing video of a neck of a human patient for monitoring JVP of the patient. In some embodiments, the sensing device 610 may at least be communicatively coupled to a base (e.g., any of the bases described herein). The sensing device 610 can be structurally and/or functionally similar to other sensing devices described herein, including, for example, sensing device 110, 210, etc. For example, the sensing device 610 includes a sternum alignment tool 618a located at a first end (e.g., a proximate end) of a body 611 of the sensing device 610, and an imaging assembly 612 located at a second end 610b (e.g., a distal end) of the body 611 of the sensing device 110.

The imaging assembly 612 includes a camera 612b configured to capture one or images or video of a patient's neck once the sensing device 610 is correctly positioned on the torso of the patient, as described herein. The camera 612b may be substantially similar to the camera 312b or any other camera, imager, or imaging device described herein. The imaging assembly 612 also includes a light source 612a disposed at a proximate end of the imaging assembly 612b and is configured to project electromagnetic radiation (e.g., visible light, infrared light, NIR light, UV light, any suitable electromagnetic radiation, or a combination thereof) on the neck of the patient, and may include an LED light source or any other light source. As shown in FIG. 13-14B, the light source 612a may be shaped as a ring, but in other embodiments, the light source 612a may have any suitable shape or size. In some embodiments, the light source 612a may also be configured to project a reference element (e.g., a reference image) on the neck of the user, as described herein. The light source 612a may be substantially similar to the light source 312a, or any other light source as previously described herein.

In some embodiments, an opening 617 may be defined at proximate end of the imaging assembly 612b (e.g., a portion of the body 611 within which the camera 612a is disposed). The opening 617 may allow light to travel therethrough to a sensing surface of the camera 612a. In some embodiments, one or more lens(es) and/or filter(s) (e.g., the lens(es) 312c or filter(s) 312d, respectively, or any other lens(es) and/or filter(s) described herein) may be disposed upstream of the camera 612b and configured to focus the electromagnetic radiation on to the camera 612b, and/or filter noise, as previously described herein. In some embodiments, a filter such as an NIR filter can be molded into the camera housing of the imaging assembly 612, e.g., to allow NIR light to pass through and be captured by the camera while filtering out other light. This can allow only NIR light to pass back to a camera, while reducing the impact of ambient illumination (e.g., from flicker of artificial lights).

In some embodiments, the imaging assembly 612 may be coupled to the body 611 at a joint 615. The joint 615 may include a hinge, a sliding joint, rotary joint, a ball-socket joint, or any other suitable joint configured to allow the imaging assembly 612 to rotate about at least one axis (e.g. the X, Y, and/or Z-axis), and/or be linearly displaced relative to the body 611. In some embodiments, the joint 615 can be used, e.g., by a physician, to calibrate the sensing device 610 to a particular patient, e.g., by setting the angle between the imaging assembly 612 and the rest of the sensing device 610, to facilitate capture of the neck and reference element in use. Once the physician has set the angle of the imaging assembly 612, the physician can lock the angle, e.g., to prevent the patient from changing the calibrated sensing device 610.

The body 611 is configured to be engaged by a hand of a user. A ridge 613 may be defined in the body 611 that is shaped and sized to receive a thumb, an index finger, and/or a webbing between the thumb and index finger of the patient around at least a portion thereof. The body 611 (e.g., a top surface of the body 611 or an elongated portion of the body 611 to which the imaging assembly 612 is coupled) may also provide one or more curvatures configured to conform to or be gripped by the hand of the patient. Thus, the ridge, and/or one or more curvature may serve as ergonomic handling features to allow the patient to grip the body 611, or position the patient's hand on a desired location or in a desired orientation on the body 611.

The sternum alignment tool 618a is configured to allow correct positioning of the sensing device 610 on a torso of the patient. For example, the sternum alignment tool 618a may include a spherical or hemispherical portion extending from, coupled to, or otherwise integrally formed on a bottom surface the body 611 at the proximate end 618a thereof that is configured to be located in a suprasternal notch of the patient, as previously described herein. In some embodiments, the sternum alignment tool 618a may also include a position sensor 619 (e.g., an electrode) provided on the bottom surface of the body 611 proximate to the spherical portion. The position sensor 619 may be configured to contact a skin of the user when the spherical portion is disposed in the suprasternal notch and generate a signal indicating to the sensing device 610 or the patient that the sensing device 610 is correctly positioned. In some embodiments, the sternum alignment tool 618a can function as a reference element, as described above.

In some embodiments, the sensing device 610 may also include a second positioning tool 618b extending from, coupled to, or otherwise integrally formed in a bottom surface of the body 611. The second positioning tool 618b is spaced apart from the sternum alignment tool 618a so as to be located proximate to the imaging assembly 612. The second positioning element 618b may be configured to be positioned on a chest (e.g., a right pectoral muscle) of the patient so as to facilitate correct positioning of the sensing device 610 on the patient's torso.

While not depicted, in some embodiments, multiple light sources and multiple cameras can be used, e.g., to capture image data in different regions (e.g., optical, NIR, and/or other frequencies). As such, in some embodiments, two or more light sources may be used, e.g., to project light at a target area (e.g., a neck of the patient), and two or more cameras can be disposed within the imaging assembly to capture reflected light from the target area. In such embodiments, the different light sources and cameras can facilitate capture of different types of image data, which can be useful for capturing 3D data and/or richer data of anatomical features.

Figure 15A:
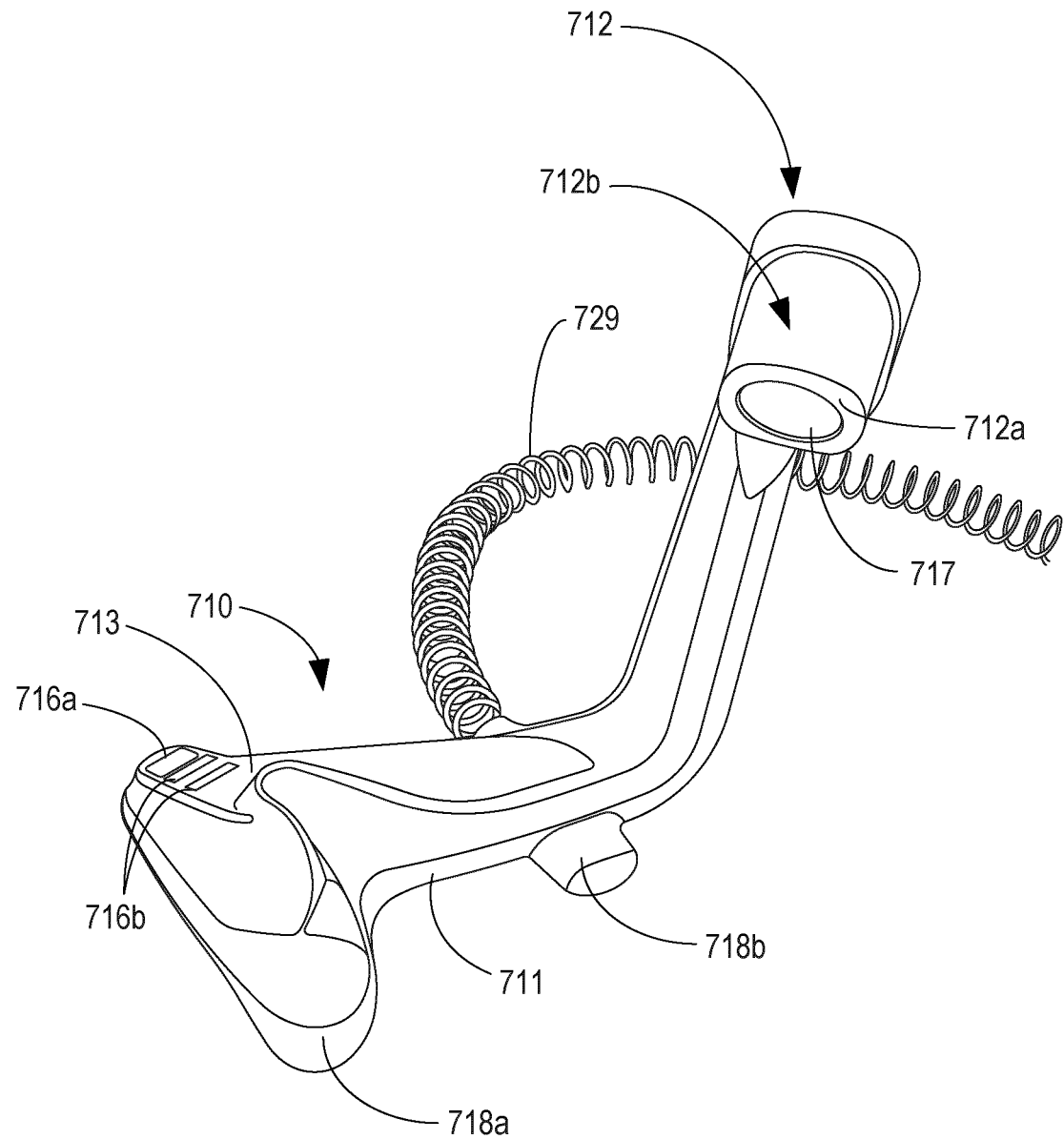
FIG. 15A is a front isometric view of a sensing device for measuring a patient's JVP, according to an embodiment.
Figure 15B:
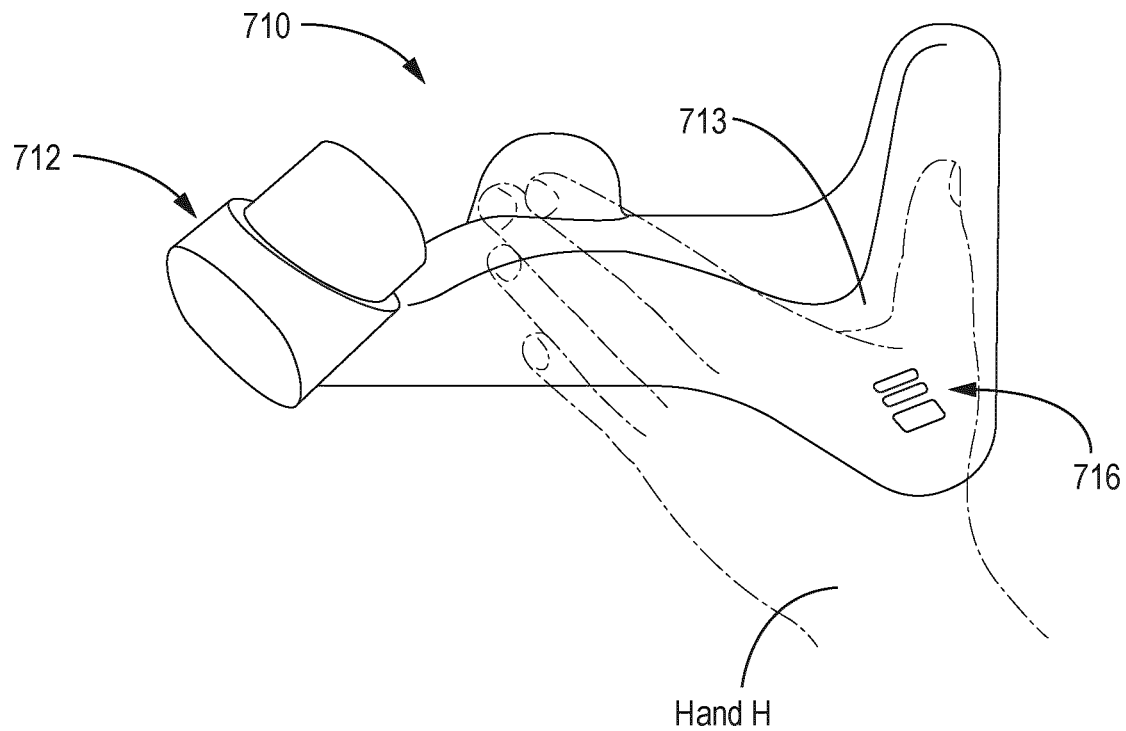
FIG. 15B is a top view of the sensing device of FIG. 15A being engaged by a hand of a patient, according to an embodiment.

FIGS. 15A and 15B depict another example of a sensing device 710, e.g., for measuring JVP, according to embodiments. FIG. 15A is a front isometric view of the sensing device 710, and FIG. 15B is a top view of the sensing device 710 of FIG. 15A being engaged by a hand H of patient, according to an embodiment. The sensing device 710 can be structurally and/or functionally similar to other sensing devices described herein, including, for example, sensing device 110, 210, 610, etc.

The sensing device 710 includes an imaging assembly 712 located on a distal end of a body 711 of the sensing device 710. The imaging assembly 712 may also include a light source 712a, a camera 712b, and an opening 717 defined at a proximate end of the imaging assembly 712. The sensing device 712 also includes a sternum alignment tool 718a disposed on a proximate end of the body 711, and a second positioning element 718b spaced apart from the sternum alignment tool 718a. The body 711 also defines a ridge 713 that is substantially similar to the ridge 613 defined with respect to the sensing device 610. The body 711, the imaging assembly 712, the sternum alignment tool 718a, and the second positioning element 718b, may be substantially similar to the body 611, the imaging assembly 612, the sternum alignment tool 618a, and the second positioning tool 618b described with respect to the sensing device 610, and therefore, not described in further detail herein. In some embodiments, the sensing device 710 may also include a communication lead 729 (e.g., a coiled cord) configured to at least communicatively couple the sensing device 710 to a base (e.g., any of the bases described herein).

Different from the sensing device 610, the sensing device 710 also includes a first sensor 716a and a pair of second sensors 716b disposed on, or located on, an upper surface of the body 711 disposed proximate to ridge 713. In some embodiments, the first sensor 716a may include a PPG sensor configured to measure PPG data of the patient. The pair of second sensors 716b (hereinafter "second sensors 716b") may be located adjacent to the first sensor 716a. The second sensors 716b may include parallel electrodes that are spaced apart from each other and configured to measure an ECG of the patient. In some embodiments, additional sensors may also be included, including, for example, a blood oxygen sensor configured to measure a blood oxygen level of the patient, a temperature sensor configured to measure a skin temperature of the patient, an electrodermal activity sensor configured to measure electrodermal activity data of the patient, etc.

FIG. 15B shows a hand H of patient disposed on the upper surface of the body 711 such that patient's thumb is positioned around at least a portion of the ridge 713 and a portion of a palm of the patient's hand H is disposed on, and in contact with the first sensor 716a and the second sensors 716b. The ridge 713 can be sized and shaped to facilitate positioning of the patient's hand H on the sensing device 710 while gripping the sensing device 710 for suitable positioning for performing a JVP measurement. In particular, the patient may grip the sensing device 710, as shown in FIG. 15B and dispose the sensing device 710 in the correct position on the patient's torso, thereby allowing the sensing device 710 to measure the patient's JVP, as well as simultaneously measure the patient's pulse, ECG, blood oxygen, etc.

Figure 16:
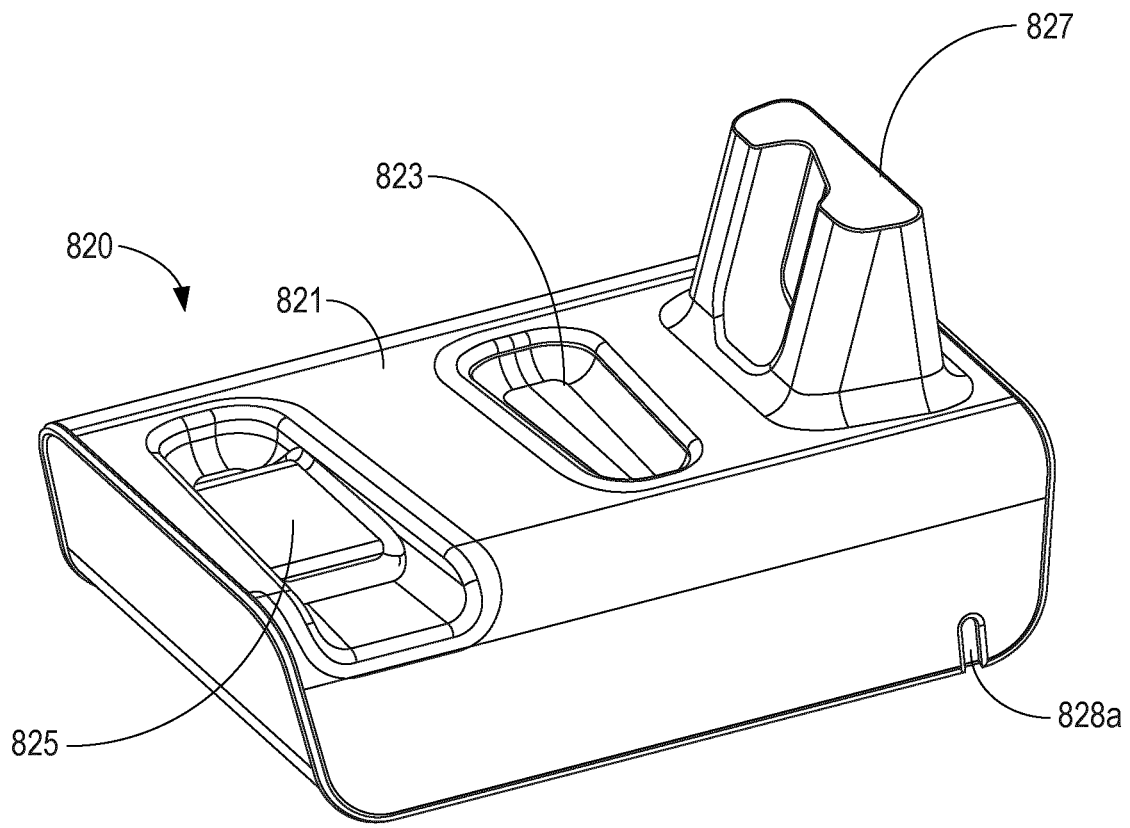
FIG. 16 is a front isometric view of a base for receiving a sensing device that is used for measuring a patient's JVP, according to an embodiment.
Figure 17A:
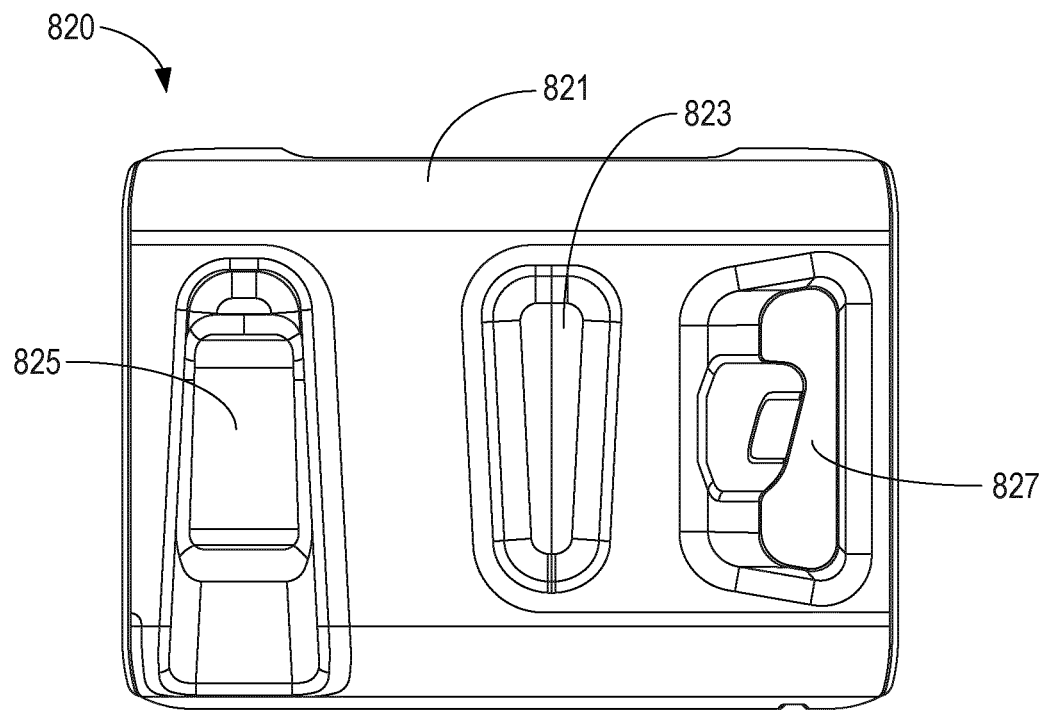
FIG. 17A is a top view of the base of FIG. 16.
Figure 17B:
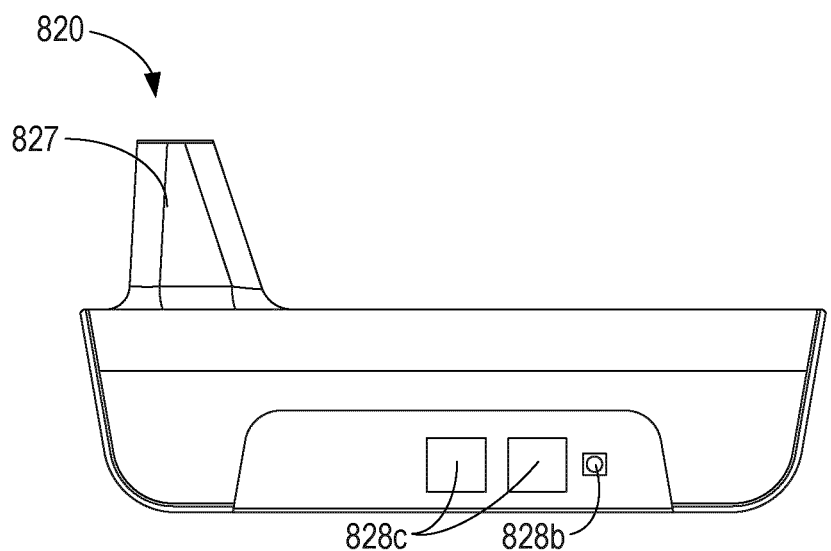
FIG. 17B is rear elevation view of the base of FIG. 16.
Figure 18:
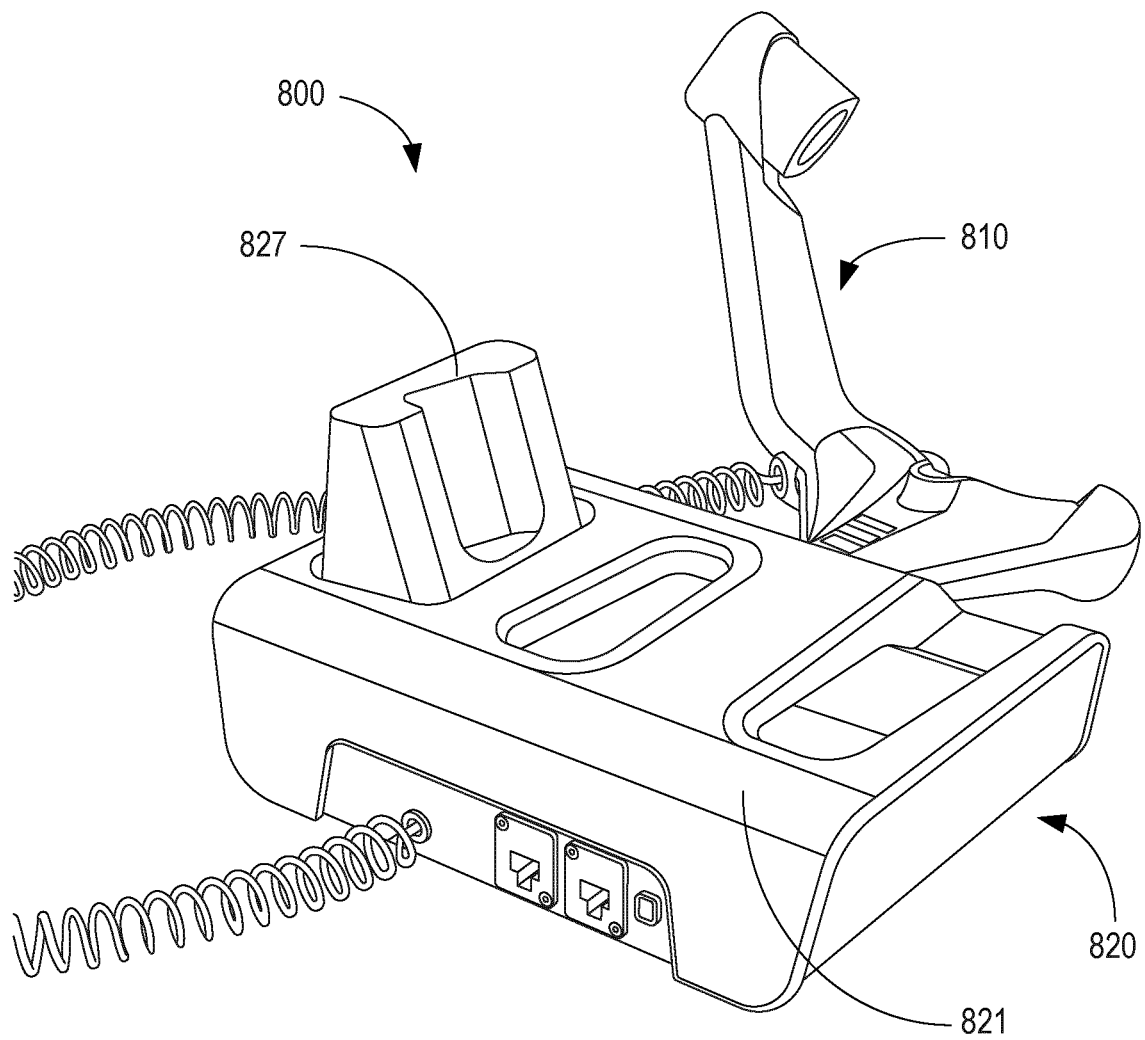
FIG. 18 is an isometric view of the system of FIGS. 17A-17B with a sensing device communicatively coupled thereto.

FIGS. 16-17B are various views of a base 820, and FIG. 18 is an isometric view of a system 800 that includes the base 820 and a sensing device 810 communicatively coupled to the base 820, according to an embodiment. The sensing device 810 may be substantially similar to the sensing device 610 or 710 (or other sensing devices described herein) and, therefore, is not described in further detail herein. The base 820 includes a housing 821 structured to receive the sensing device 810 thereon (e.g., for storage, charging, etc.). In some embodiments, the housing 821 may include an upper portion that may be coupled to a lower portion so as to define an internal volume within which various components of the base 820 may be disposed.

An upper surface of the housing 821 defines a first cavity 823 that is sized and shaped to receive a second positioning tool of the sensing device 810 (e.g., the second positioning tool 618b, 718b, or any other second positioning tool described herein), and a second cavity 825 sized and shaped to receive a sternum alignment tool of the sensing device 810 (e.g., the sternum alignment tool 618a, 718a, or any other sternum alignment tool described herein) when the sensing device 810 is disposed on the base 820. The base 820 also includes a support arm 827 extending upwards form the housing 821, which is configured to support at least a portion of a body of the sensing device 810, for example, a portion of the body of the sensing device 810 to which an imaging assembly of the sensing device 810 is coupled. (e.g., an elongated neck portion of the body of the sensing device 810). The support arm 827 may define a groove that is shaped and sized to receive at least a portion of the body of the sensing device 810. The elongate portion of the body of the sensing device 810 may offset the center of gravity of the sensing device 810 making the sensing device 810 vulnerable to toppling over. Thus, the support arm 827 may provide support to the body of the sensing device 810, thereby enabling the sensing device 810 to stably sit on the base 820 when the sensing device 810 is disposed on the base 820.

The base 820 may include an indicator lamp 828a disposed or provided on a first sidewall of the housing 821 (e.g., a front sidewall of the housing 821. The indicator lamp 828a may include a light source (e.g., an LED light) that may be configured activate (e.g., light up or illuminate) to indicate to the patient that the base 820 is coupled to a power source or activated, and/or the imaging assembly of the sensing device 820 is capturing image or video data. The base 820 may include a power socket 828b disposed on or through a second sidewall of the housing 821 opposite the first sidewall. The power socket 828b may be configured to receive a power cord so as to receive electrical power from the power cord, and use the electrical power to power the various components included in the base 820 and/or the sensing device 810, and/or recharge a power source (e.g., a rechargeable battery) included in the base 820 and/or the sensing device 810.

The base 820 can include a first communication interface or port 828b and a second communication interface or port 828c. The communication interfaces 828b, 828c may include or be coupled to suitable device(s) and/or interface(s) that can communicate with the sensing device 810 (e.g., any or the devices, sensors, and/or data sources described above with respect to the sensing device 810, and/or any combination or part thereof), a network (e.g., a LAN, a (WAN, or the cloud), or an external device (e.g., a user device such as cell phone, tablet, a laptop or a desktop computer, etc.). Moreover, the communication interfaces 828b, 828c can include or be coupled to one or more wired and/or wireless interfaces, such as, for example, Ethernet interfaces, optical carrier (OC) interfaces, and/or asynchronous transfer mode (ATM) interfaces. In some embodiments, the communication interfaces 828b, 828c can be, for example, a network interface card and/or the like that can include at least an Ethernet port and/or a wireless radio (e.g., a WI-FI® radio, a BLUETOOTH®) radio, cellular, 802.11X, Zigbee, etc.). In some embodiments, the base 820 may also include one or more communication devices, for example, satellite, WI-FI, BLUETOOTH, or cellular antennae. In some embodiments, the base 820 can be communicably coupled to an external device (e.g., via the communication interfaces 828b, 828c) that includes one or more satellite, WI-FI, BLUETOOTH, or cellular antenna, or a power source such as a battery or a solar panel.

As depicted in FIG. 18, unlike the embodiment of the device 500 described with reference to FIGS. 12, where the sensing device and the base are coupled to one another via an adjustable arm, the sensing system 810 and base 820 are coupled to one another via a wired connection. With such a connection, greater adjustability in the positioning of the sensing device 810 relative to the base 820 can be achieved, as described with reference to FIG. 3B above. The flexible wired connection can also place less weight and/or forces upon the base 820, e.g., during positioning and/or adjustment of the sensing device 810, thereby reducing the risk of undesirable movement of the base 820 (e.g., tilting, sliding, etc.). As such, the weight and/or form factor of the base 820 can also be reduced. In some embodiments, the sensing device 810 can also be detached from the wired connection, e.g., by unplugging the wired connection from the sensing device 810. In such configurations, the sensing device 810 may include an onboard power source (e.g., a battery), a communication interface for sending and/or receiving signals and data from the base 820, and/or a charging connection (e.g., contact electrodes, wireless, port, plug, etc.), e.g., similar to that described with reference to FIG. 3C above. The flexible wired connection can facilitate greater portability of the system 800, e.g., as compared to the device 500.

Figure 19A:
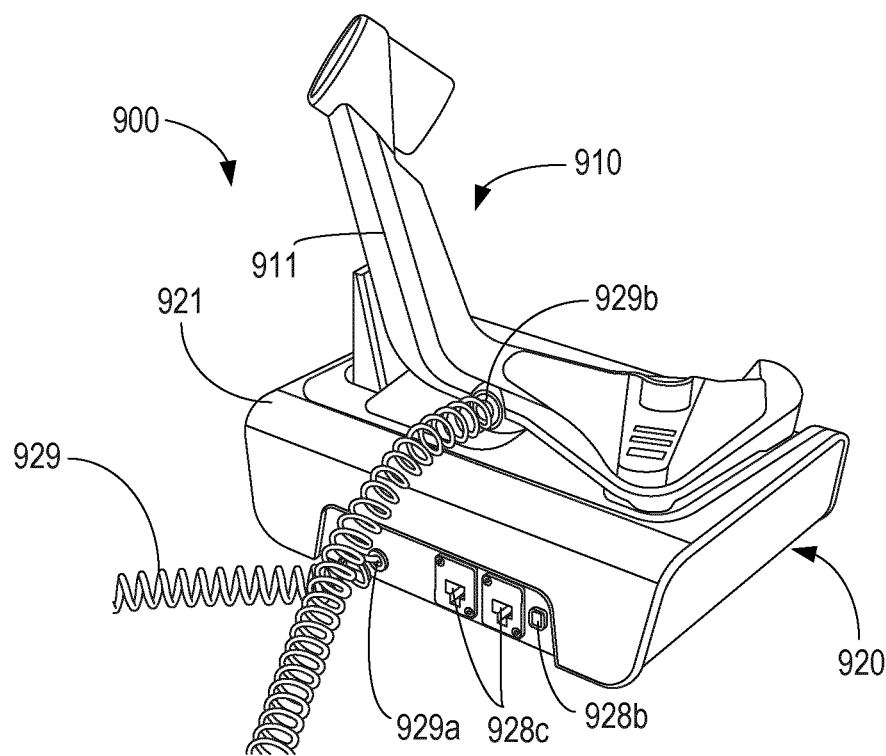
FIGS. 19A and 19B are front and rear isometric views, respectively of a system for measuring a patient's JVP that includes a sensing device operatively coupled to a base and resting on the base, according to an embodiment.
Figure 19B:
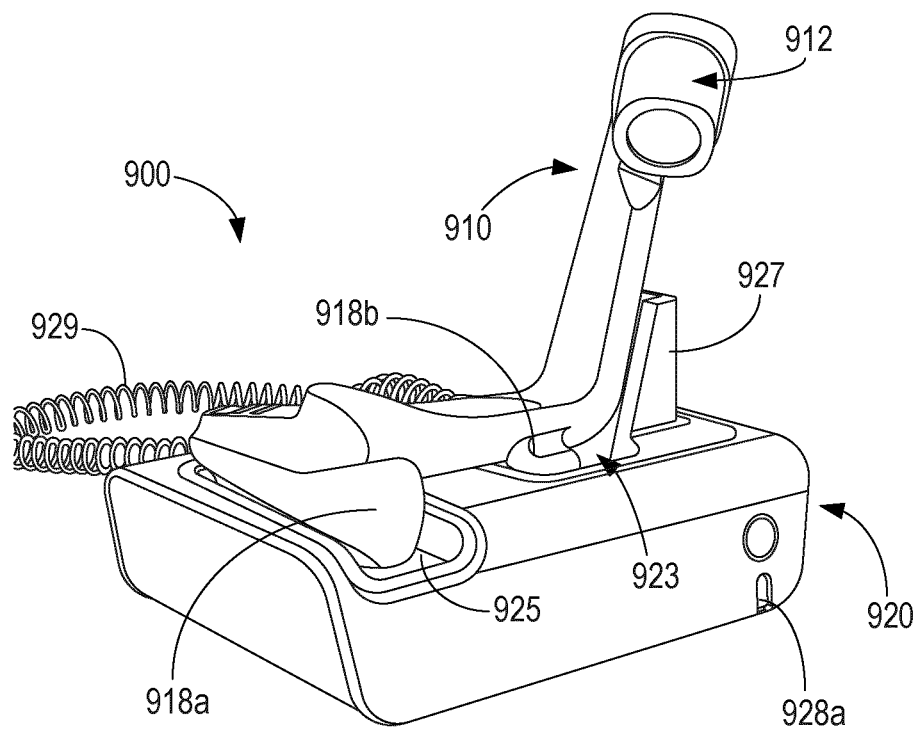

FIGS. 19A and 19B are front and rear isometric views, respectively of a system 900 for measuring a patient's JVP that includes a sensing device 910 operatively coupled to a base 920 and resting on the base 920, according to an embodiment. The system 900 can be similar to other monitoring systems described herein, including, for example, the monitoring system 800 described above. The sensing device 910 incudes a body 911 that is configured to rest on the base 920. The sensing device 910 includes an imaging assembly 910 disposed on a first end (e.g., a distal end) of the body 911, and a sternum alignment tool 918a disposed a second end of the body 911 (e.g., a proximate end). The sensing device 910 also includes a second positioning tool 918b spaced apart from the sternum alignment tool 918a. The sternum alignment tool 918a and the second positioning tool 918b may be disposed on a lower or bottom surface of the sensing device 910. The body 911, the imaging assembly 912, the sternum alignment tool 918a, and the second positioning tool 918b may be substantially similar to the body 611/711, the imaging assembly 612/712, the sternum alignment tool 618a/718a, and the second positioning tool 618b/718b and therefore, not described in further detail herein. The sensing device 910 is communicatively coupled to the base 920 via a communication lead 929 (e.g., a coiled cord). For example, as shown in FIG. 19A, a first end 929a of the communication lead 929 is coupled to the base 920, and a second end 929b of the communication lead 929 is coupled to the sensing device 910.

Figure 20:
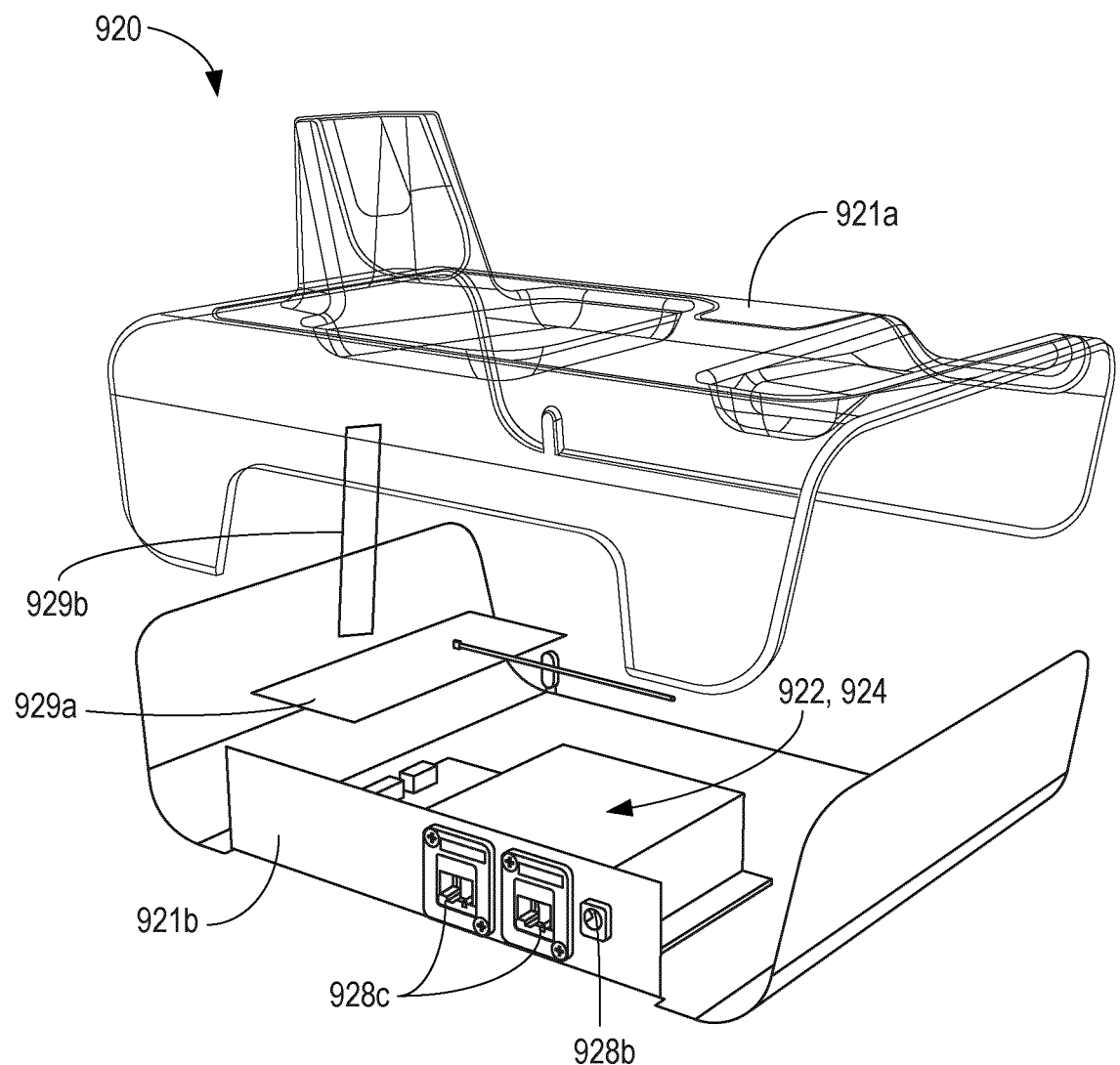
FIG. 20 is an exploded view of the base of FIGS. 19A-19B.

Referring also now to FIG. 20 that shows an exploded view of the base 920, the base 920 includes a housing 921 structured to receive the sensing device 910 thereon in a configuration in which the sensing device 910 is not being used or otherwise, is stowed for later use. As shown in FIG. 20, the housing 921 includes a housing upper portion 921a configured to be removably coupled to a housing lower portion 921b (e.g., via friction fit, via snap-fit thereto, or via coupling members such as screws, nuts, bolts, rivets, etc.) or fixedly coupled thereto (e.g., via an adhesive, or fusion bonding) so as to define an internal volume within which various components of the base 920 are disposed.

An upper surface of the housing 921 defines a first cavity 923 that is sized and shaped to receive the second positioning tool 918b of the sensing device 910, and a second cavity 925 sized and shaped to receive the sternum alignment tool 918a of the sensing device 910 when the sensing device 910 is disposed on the base 920. The base 920 also includes a support arm 927 extending upwards form the housing 921, which is configured to support at least a portion of a body 911 of the sensing device 910, as previously described herein The support arm 927 may define a groove that is shaped and sized to receive at least a portion of the body 911 of the sensing device 910, so as to provide support to the body 911 of the sensing device 910.

The first cavity 923 and the support arm 927 can be different in shape and configuration from the cavity 823 and the support arm 827 of the base 820. In particular, the first cavity 923 can be larger (e.g., wider and/or deeper) than the first cavity 823. This can allow the sensing device 910 to sit more security within the cavity 923. The support arm 927 can be smaller (e.g., narrower and shorter) than the support arm 827. In some embodiments, the support arm 927 can be made smaller given the larger configuration of the cavity 923, e.g., the support arm 927 can be smaller because the cavity 923 provides greater support to the sensing device 910. In some embodiments, the larger sized first cavity 923 may provide a larger insertion area for the second positioning tool 918b to be positioned therein, thereby facilitating placement of the sensing device 910 on the base 920 in a desired orientation.

The base 920 may also include an indicator lamp 928a disposed on or provided on a first sidewall of the housing 921a. The indicator lamp 928a may include a light source (e.g., an LED light) that may be configured activate (e.g., light up or illuminate) to indicate to the patient that the base 920 is coupled to a power source or activated, and/or the imaging assembly of the sensing device 820 is capturing image or video data. The base 920 may also include a power socket 828b disposed on or through a second sidewall of the housing 921 opposite the first sidewall. The power socket 928b may be configured to receive a power cord so as to receive electrical power from the power cord, and provide electrical power to the various components included in the base 920 or the sensing device 910.

The base 920 may include a memory 922, and a processor 924 disposed in the housing 921, and that may be substantially similar to the memory 122 and the processor 124, as previously described herein. Additionally, the base 920 may also include communication interfaces 928c provided or disposed on the second sidewall included in the housing second portion 921b. The communication interfaces 928c may include suitable device(s) and/or interface(s) that can communicate with the sensing device 910 (e.g., any or the devices, sensors, and/or data sources described above with respect to the sensing device 910, and/or any combination or part thereof), a network (e.g., a LAN, a (WAN, or the cloud), or an external device (e.g., a user device such as cell phone, tablet, a laptop or a desktop computer, etc.). Moreover, the communication interfaces 928c can include one or more wired and/or wireless interfaces, such as, for example, Ethernet interfaces, optical carrier (OC) interfaces, and/or asynchronous transfer mode (ATM) interfaces. In some embodiments, the communication interfaces 928c can be, for example, a network interface card and/or the like that can include at least an Ethernet port and/or a wireless radio (e.g., a WIFI® radio, a BLUETOOTH® radio, cellular, 802.11X Zigbee, etc.). In some embodiments, the base 920 may also include one or more communication devices, for example, satellite, WI-FI, BLUETOOTH, or cellular antennae. For example, as shown in FIG. 20, the base 920 may include a first antenna 929a (e.g., a horizontal antenna), and a second antenna 929b (e.g., a vertical antenna) for providing communication between the base 920 and external devices (e.g., a user device, a local server, a remote server, the cloud, etc.). In some embodiments, the base 820 can be communicably coupled to an external device (e.g., via the communication interfaces 928c) that includes one or more satellite, WI-FI, BLUETOOTH, or cellular antenna, or a power source such as a battery or a solar panel.

Figure 21:
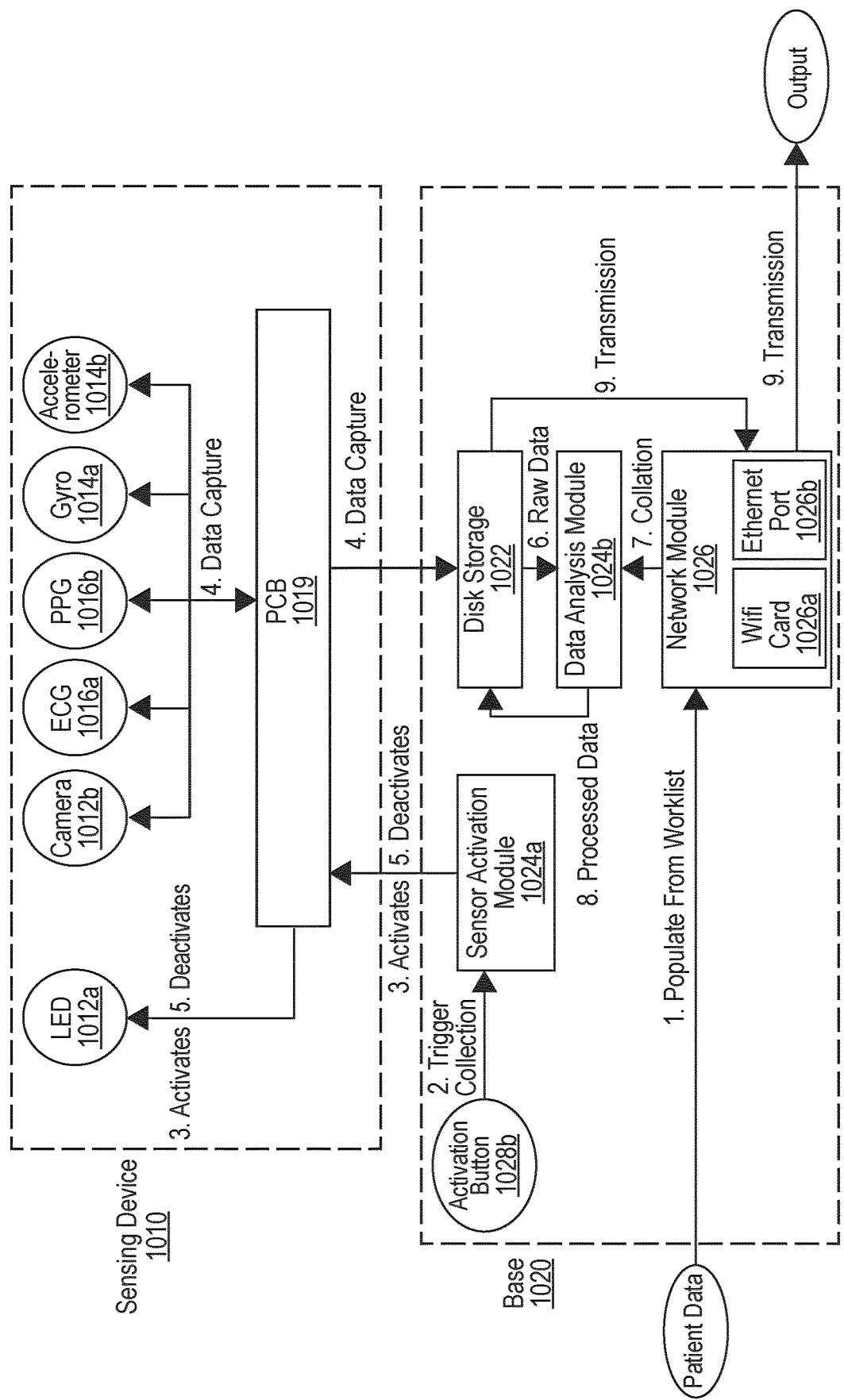
FIG. 21 is a schematic block diagram of a system for measuring a patient's JVP that includes a sensing device and a base, according to an embodiment.

Different configurations of elements within the sensing devices and bases of monitoring systems described herein are possible. For example, FIG. 21 schematically depicts one configuration of a system that includes a sensing device 1010 communicatively coupled to a base 1020, according to an embodiment. The sensing device 1010 and the base 1020 can be structurally and/or functionally similar to other sensing devices and bases described herein, including, for example, sensing device 110, 210, 310, 610, 710, etc. and bases 120, 220, 720, etc. The sensing device 1010 may be configured to measure a JVP of a user as previously described herein. The sensing device 1010 includes a PCB 1019 that may include a memory and/or processor (and other associated circuitry). The sensing device also includes a light source implemented as an LED 1012a and a camera 1012b that may be substantially similar to the light source 312a and 312b, respectively, or any other light source or camera described herein. For example, the LED 1012a can include one or more illumination LEDs, and can be implemented as a light ring or other structure in the sensing device 1010. The LED 1012a and the camera 1012b are communicatively coupled to the PCB 1019, and configured to receive an activation/deactivation signal from the base 1020 via the PCB 1019 to turn ON/turn OFF the LED 1012a, and/or initiate or stop image and/or video capture via the camera 1012b.

The sensing device 1010 may also include one or more sensors. In some embodiments, the sensing device 1010 includes an ECG sensor 1016a, a PPG sensor 1016b, and at least one of a gyroscope 1014a or an accelerometer 1014b. The ECG sensor 1016a may include a two or more electrodes spaced apart from each other and configured to capture an ECG of a patient when the sensors come in contact with a skin of the patient. The PPG sensor 1016b may be configured to measure PPG data of a patient (e.g., a pulse, heartrate, oxygen saturation, blood pressure or blood pressure trends, respiratory rate, SpO2, respiratory effort, etc.). The gyroscope 1014a and the accelerometer 1014b may be configured to sense a position or displacement of the sensing device 1010 and generate data that may be used to determine if the patient is reclined in a suitable orientation, the sensing device 1010 is positioned on the correct location of a torso of the patient, and/or the sensing device 1010 is relatively immobile after being placed on the patient's torso. The data from the gyroscope 1014a and the accelerometer 1014b can be sent, e.g., to PCB 1019 and/or a processor of the base 1020, which can then initiate and/or stop activation of the lights source 1012a and/or the camera 1012b. The ECG sensor 1016a, the pulse oximeter sensor 1016b, the gyroscope 1014a, and the accelerometer 1014b may be communicatively coupled to the base 1020 via the PCB 1019. In some embodiments, the PCB 1019 can perform pre-processing of the data from the sensors, e.g., to time-align the data and/or clean the data, before passing the data from the sensors onto the base 1020.

The base 1020 includes a disk storage 1022, a sensor activation module 1024a, a data analysis module 1024b, and a network module 1026. The disk storage 1022 may include a memory (e.g., the memory 122 described with respect to the base 120 or any other memory described herein), and is configured to receive and at least temporarily store raw data or partially processed data from the camera 1012b, the gyroscope 1014a, the accelerometer 1014b, the ECG sensor 1016a, and the PPG sensor 1016b. The disk storage 1022 is configured to communicate the raw data to the data analysis module 1024b (e.g., a processor such as the processor 124 described with respect to the base 120 or any other processor described herein) that may be configured to process the data, and communicate the processed data to the data storage 1022 for at least temporary storage.

In some embodiments, the data analysis module 1024b may also be configured to receive data (e.g., patient data, historical data, or other data) from the network module 1026, and use the data to process the data received from the sensing device 1010 via the PCB 1019. The network module 1026 may include a WI-FI® card 1026a and/or an ethernet port 1026b configured to communicate with external devices (e.g., user devices, remote servers, health databases, the cloud, etc.). In some embodiments, the base 1020 may be configured to receive patient data (e.g., populated from a worklist such as a health database) via the network module 1026. The patient data may come from a remote compute device, e.g., a database, server, or other compute device that is connected via a network to the base 1020. In some embodiments, the connection for receiving the patient data can be a wired connection, while in other embodiments, the connection for receiving the patient data can be a wireless connection. The network module 1026 may generate collated data based on the patient data, or transmit patient data to the data analysis module 1024b that may be configured to use the patient data to process and/or analyze the data received from the sensing device 1010. In some embodiments, the network module 1026 may also be configured to receive a transmission from the disk storage module 1022. The transmission may include the processed data, raw data, and/or any other data, and the network module 1026 may be configured to generate an output (e.g., an output signal) that is indicative of the transmission, and is communicated by the network module 1026 to an external device (e.g., a compute device that is external to the base 1020). For example, the network module 1026 can include an antenna or other communication element for transmitting the output to an external server or database.

In some embodiments, the base 1020 may also include an activation button 1028b (e.g., similar to the patient-actuated switch as described above). The activation button 1028b may be configured to be engaged (e.g., a pressed) by the patient, a user, or a caregiver to activate/deactivate the base 1020 and thereby, the sensing device 1010. In response to the activation button 1028b being engaged, a trigger collection signal or otherwise, an activation/deactivation signal is transmitted to the sensor activation module 1024a. In some embodiments, the sensor activation module 1024a may include a processor, or a controller configured to send an activation/deactivation signal to the LED 1012a to turn ON/turn OFF, and to camera 1012b to initiate/stop image or video capture.

Figure 22:
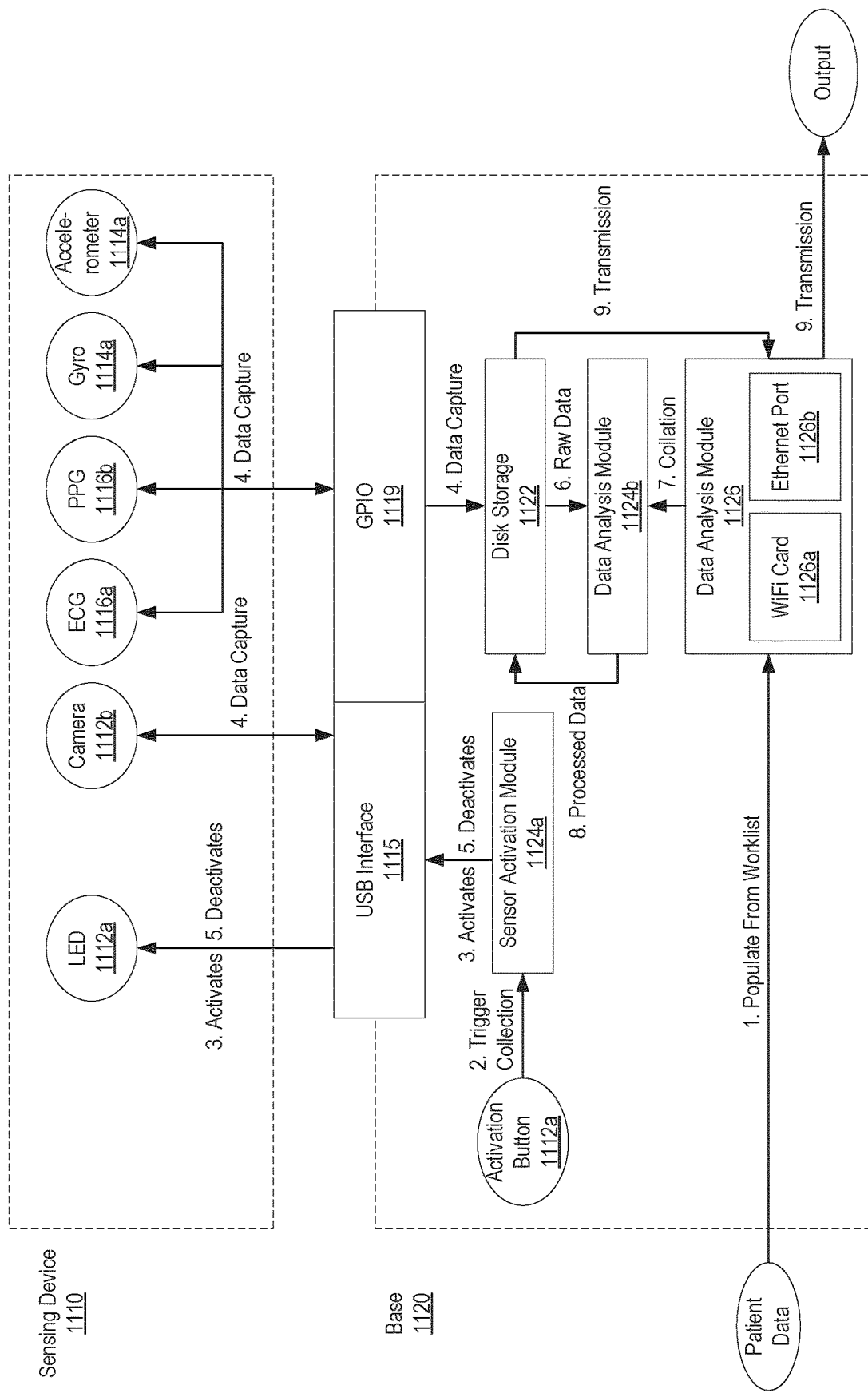
FIG. 22 schematic block diagram of a system for measuring a patient's JVP that includes a sensing device and a base, according to an embodiment.

FIG. 22 schematically depicts another configuration of a monitoring system that includes a sensing device 1110 communicatively coupled to a base 1120, according to an embodiment. The sensing device 1110 and the base 1120 can be structurally and/or functionally similar to other sensing devices and bases described herein. For example, the sensing device 1110 and the base 1120 can be similar to the sensing device 1010 and the base 1020, except that in place of a PCB in the sensing device (such as depicted in FIG. 21), there is a USB interface 1115 and/or an input/output or GPIO 1119 that couples various elements of the sensing device 1110 to the relevant processing modules and elements in the base 1120. In particular, one or more of the sensor(s) (e.g., camera 1112b, ECG sensor 1116a, PPG sensor 1116b, gyroscope 1114a, accelerometer 1114a) can be coupled to the base 1120 via the USB interface 1115 and/or GPIO 1119. The LED 1112a can also be coupled to the base 1120 via the USB interface 1115 and/or GPIO 1119. Other aspects of the system configuration depicted in FIG. 22 are similar to those described with respect to the system configuration depicted in FIG. 21, and therefore are not repeated herein again.

Figure 23:
FIG. 23 depicts a static image generated by an imaging assembly of a system for measuring a patient's JVP, schematically depicting relationship between variable rotation of neck and lines in static image plane, according to an embodiment.

In some embodiments, any of the imaging devices described herein (e.g., cameras, imagers, etc.) can be used to capture one or more static images of a patient's neck with a sensing device (or at least a portion of the sensing device) positioned thereon. FIG. 23 depicts an example of such a static image, according to embodiments. As shown FIG. 23, a portion of a sensing device 1210 can be captured, that includes a positioning element 1218. The positioning element 1218 can be implemented as a locator object with a portion that is positioned in a suprasternal notch of the patient. In the static image, the end of the positioning element 1218 that is positioned in the supra sternal notch is known, i.e., at a fixed point (X,Y). The long axis of the patient neck can rotate about this fixed point (X,Y). Therefore, the long axis of the patient neck can be determined, and then its relationship with the fixed point (X,Y) can be used to determine an angle of the neck relative to the angle of the sensing device 1210. The angle of the sensing device 1210 can be known relative to vertical such that the angle of the long axis of the neck relative to the vertical can be determined, and the vertical height of the JVP can be determined using trigonometrical calculations. In FIG. 23, the static image can be segmented, as schematically depicted using lines 1202-1208. The long axis of the neck can be best approximated using one of these lines 1202-1208. While four lines are shown, it can be appreciated that any number of lines can be used to segment the image, and the line that best approximates the long axis of the neck can be determined. It can also be appreciated that other methods of segmenting the image can be used, e.g., in accordance with standard image processing techniques, to identify the long axis of the neck and/or other anatomical features in the image. The long axis of the neck can be aligned with a line that is closest to it, and the angle associated with that line can be used to approximate the angle of the long axis of the neck, which can subsequently be used to determine the vertical height of the JVP, as described above.

The present technology is not limited in its application to the details of construction and the arrangement of components set forth in the preceding description or illustrated in the drawings. The present technology is capable of other embodiments and of being practiced or of being carried out in various ways. Also, the phraseology and terminology used herein is for the purpose of description and should not be regarded as limiting.

Certain systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The use of "including", "comprising", or "having", "containing", "involving" and variations thereof herein, is meant to encompass the items listed thereafter as well as, optionally, additional items. In the description the same numerical references refer to similar elements.

It must be noted that, as used in this specification and the appended claims, the singular form "a", "an" and "the" include plural referents unless the context clearly dictates otherwise.

As used herein, the term "about" or "generally" or the like in the context of a given value or range (whether direct or indirect, e.g., "generally in line", "generally aligned", "generally parallel", etc.) refers to a value or range that is within 20%, preferably within 10%, and more preferably within 5% of the given value or range.

As used herein, the term "and/or" is to be taken as specific disclosure of each of the two 10 specified features or components with or without the other. For example, "A and/or B" is to be taken as specific disclosure of each of (i) A, (ii) B and (iii) A and B, just as if each is set out individually herein.

Modifications and improvements to the above-described implementations of the present technology may become apparent to those skilled in the art. The foregoing description is intended to be exemplary rather than limiting. The scope of the present technology is therefore intended to be limited solely by the scope of the appended claims.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that the use of the terms "first unit" and "third unit" is not intended to imply any particular type, hierarchy or ranking (for example) of/between the units. Nor is their use (by itself) intended to imply that any "second unit" must necessarily exist in any given situation.

In the context of the present specification, the word "embodiment(s)" is generally used when referring to physical realizations of the present technology and the word "implementations" is generally used when referring to methods that are encompassed within the present technology (which generally involve also physical realizations of the present technology). The use of these different terms is not intended to be limiting of or definitive of the scope of the present technology. These different terms have simply been used to allow the reader to better situate themselves when reading the present lengthy specification.

As utilized herein, the terms "substantially' and similar terms are intended to have a broad meaning in harmony with the common and accepted usage by those of ordinary skill in the art to which the subject matter of this disclosure pertains. For example, the term "substantially flat" would mean that there may be de minimis amount of surface variations or undulations present due to manufacturing variations present on an otherwise flat surface. It should be understood by those of skill in the art who review this disclosure that these terms are intended to allow a description of certain features described and claimed without restricting the scope of these features to the precise arrangements and/or numerical ranges provided. Accordingly, these terms should be interpreted as indicating that insubstantial or inconsequential modifications or alterations of the subject matter described and claimed are considered to be within the scope of the inventions as recited in the appended claims.

The terms "coupled," and the like as used herein mean the joining of two members directly or indirectly to one another. Such joining may be stationary (e.g., permanent) or moveable (e.g., removable, or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes, and omissions may also be made in the design, operating conditions, and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Thus, particular implementations of the invention have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. An apparatus, comprising:
a positioning element sized and shaped to be capable of registering with the size and shape of a particular anatomic location on a chest of a patient, such that the positioning element can be repeatedly and stably positionable on the body of the patient with respect to the anatomic location;
a reference structure connected to or integrated with the positioning element, the reference structure having known spatial characteristics and being positionable with respect to the neck of the patient by positioning of the positioning element;
an imaging assembly coupled to and spaced from the positioning element, the imaging assembly configured to capture imaging data of at least a portion of a neck of the patient and at least a portion of the reference structure; and
a processor operatively coupled to the imaging assembly, the processor configured to determine a jugular venous pressure (JVP) height relative to an anatomical feature of the patient based on the imaging data and the known spatial characteristics of the reference structure.

2. The apparatus of claim 1, wherein the positioning element includes the reference structure.

3. The apparatus of claim 1, wherein the positioning element includes a spherical portion that is configured to fit within a suprasternal notch of the patient.

4. The apparatus of claim 1, wherein the positioning element is a first positioning element, the apparatus further comprising a second positioning element configured to rest against a portion of the chest of the patient.

5. The apparatus of claim 1, wherein the positioning element, the reference structure, and the imaging assembly are disposed on a sensing device, and the processor is disposed within a base,
the base including a surface including a set of structures configured to receive a portion of the sensing device and to stably support the sensing device on the surface of the base.

6. The apparatus of claim 1, wherein the imaging assembly is coupled to the positioning element such that, when the positioning element is positioned within the anatomic location, the imaging assembly can be positioned to capture the imaging data of the at least the portion of the neck of the patient and the portion of the reference structure.

7. The apparatus of claim 1, wherein the imaging assembly includes a near infrared (NIR) light source configured to emit NIR light toward the neck of the patient and a NIR camera configured to capture NIR light reflected by the neck of the patient.

8. The apparatus of claim 1, wherein the imaging assembly includes first and second cameras, each of the first and second cameras configured to capture light in different wavelength ranges.

9. The apparatus of claim 8, wherein the first camera is configured to capture optical light, and the second camera is configured to capture NIR light.

10. The apparatus of claim 1, wherein the imaging assembly includes first and second cameras configured to capture light in the same wavelength ranges to provide stereovision.

11. The apparatus of claim 1, wherein the processor is configured to determine the JVP height relative to the anatomical feature of the patient by: determining, based on the portion of the reference structure captured in the image data, a conversion between pixels of the imaging data and a physical measure of distance.

12. The apparatus of claim 1, wherein the processor is configured to determine the JVP height relative to the anatomical feature of the patient by:
determining, based on the portion of the reference structure captured in the image data, a conversion between pixels of the imaging data and a physical measure of distance;

determining, from the imaging data, a highest point of a pulsation of an internal jugular vein (IJV) of the patient; and determining, based on at least the conversion between the pixels of the imaging data and the physical measure of distance, a vertical height between a sternal angle and the highest point of the pulsation of the IJV of the patient.

13. The apparatus of claim 12, further comprising at least one of an accelerometer or a gyroscope configured to measure an orientation of the neck of the patient relative to a horizontal plane, wherein the determination of the vertical height is further based on an angle of inclination of the neck of the patient as determined based on the measured orientation of the neck.

14. The apparatus of claim 1, wherein the processor is configured to determine the JVP of the patient by:

determining, based on a static image of the portion of the neck of the patient and a portion of the apparatus, an angle of a longitudinal axis of the neck relative to an angle of the apparatus;

determining, from the imaging data, a highest point of pulsation of an internal jugular vein (IJV) of the patient; and determining, based on the angle of the longitudinal axis of the neck and highest point of pulsation of the IJV, a vertical height between a sternal angle and the highest point of the pulsation of the IJV of the patient.

15. The apparatus of claim 1, further comprising an actuator configured to be actuated by the patient to cause the processor to activate the imaging assembly to capture the imaging data.

16. The apparatus of claim 1, further comprising one or more sensors including at least one of: an electrocardiogram sensor, a photoplethysmography sensor, an electrodermal activity sensor, or a temperature sensor.

17. The apparatus of claim 16, wherein the one or more sensors are disposed on a body coupled to the imaging assembly and the positioning element such that, when the patient grips the body for positioning of the positioning element relative to the anatomic location, a portion of a hand of the patient is in contact with the one or more sensors to facilitate measurement by the one or more sensors.

18. The apparatus of claim 16, wherein the one or more sensors are disposed on a body coupled to the imaging assembly and the positioning element such that, when the positioning element is positioned relative to the anatomic location, the one or more sensors are in contact with a skin of the patient to facilitate measurement by the one or more sensors.

19. The apparatus of claim 1 further comprising a second reference element that is physically separate from the positioning element, wherein the second reference element is positionable such that the imaging data captured by the imaging assembly includes at least a portion of the second reference element.

20. The apparatus of claim 19 wherein the second reference element is positionable on the neck of the patient.

* * * * *